US012653954B2

(12) United States Patent
Judson

(10) Patent No.: US 12,653,954 B2
(45) Date of Patent: Jun. 16, 2026

(54) MEDICATION DELIVERY DEVICE WITH NEEDLE CARRIER

(71) Applicant: Eli Lilly and Company, Indianapolis, IN (US)

(72) Inventor: Jared Alden Judson, Medford, MA (US)

(73) Assignee: Eli Lilly and Company, Indianapolis, IN (US)

( * ) Notice: Subject to any disclaimer, the term of this patent is extended or adjusted under 35 U.S.C. 154(b) by 1134 days.

(21) Appl. No.: 17/641,857

(22) PCT Filed: Sep. 4, 2020

(86) PCT No.: PCT/US2020/049434
§ 371 (c)(1),
(2) Date: Mar. 10, 2022

(87) PCT Pub. No.: WO2021/050384
PCT Pub. Date: Mar. 18, 2021

(65) Prior Publication Data
US 2022/0355035 A1 Nov. 10, 2022

Related U.S. Application Data

(60) Provisional application No. 62/898,744, filed on Sep. 11, 2019.

(51) Int. Cl.
*A61M 5/24* (2006.01)
*A61M 5/20* (2006.01)
(Continued)

(52) U.S. Cl.
CPC ........ *A61M 5/2429* (2013.01); *A61M 5/2033* (2013.01); *A61M 5/281* (2013.01);
(Continued)

(58) Field of Classification Search
CPC .............. A61M 5/2429; A61M 5/2033; A61M 2005/206
See application file for complete search history.

(56) References Cited

U.S. PATENT DOCUMENTS 5,762,634 A 6/1998 Davis
5,779,683 A 7/1998 Meyer
(Continued)

FOREIGN PATENT DOCUMENTS

JP 2016519976 A 7/2016
JP 2017538511 A 12/2017
(Continued)

OTHER PUBLICATIONS

"BD AutoShield Duo™ pen needle," BD, Retrieved Feb. 12, 2019, from https://www.bd-com/en-ca/offering/capabilites/diabetes-care/pen-needles/bd-autoshield-duo-pen-needle.
(Continued)

*Primary Examiner* — Bradley J Osinski
(74) *Attorney, Agent, or Firm* — M. Daniel Spillman

(57) ABSTRACT

Drug delivery devices are provided having a needle assembly portion and a drug device portion, where the needle assembly portion is removably coupleable to the drug device portion. In some embodiments, the needle of the needle assembly may be moveable from a retracted position to an extended position for piercing into a subjects skin. In some embodiments, the needle may also be moveable back to a retracted position.

19 Claims, 40 Drawing Sheets

(51) Int. Cl.
    *A61M 5/28*       (2006.01)
    *A61M 5/315*     (2006.01)
    *A61M 5/32*      (2006.01)

(52) U.S. Cl.
    CPC ...... *A61M 5/31511* (2013.01); *A61M 5/3293*
          (2013.01); *A61M 2202/0007* (2013.01)

(56) References Cited

U.S. PATENT DOCUMENTS

| | | | |
|---|---|---|---|
| 6,342,045 | B1 | 1/2002 | Somers |
| 7,056,306 | B1 | 6/2006 | Halseth et al. |
| 2001/0053886 | A1 | 12/2001 | Caizza |
| 2002/0007103 | A1 | 1/2002 | Fontayne |
| 2003/0032927 | A1 | 2/2003 | Halseth et al. |
| 2003/0045838 | A1 | 3/2003 | Woodard, Jr. et al. |
| 2004/0236284 | A1 | 11/2004 | Hoste et al. |
| 2005/0027255 | A1 | 2/2005 | Lavi et al. |
| 2005/0124940 | A1 | 6/2005 | Martin et al. |
| 2006/0287630 | A1 | 12/2006 | Hommann |
| 2007/0088268 | A1 | 4/2007 | Edwards |
| 2007/0106225 | A1 | 5/2007 | Millerd |
| 2007/0255221 | A1 | 11/2007 | Nakajima |
| 2008/0039795 | A1 | 2/2008 | Slate et al. |
| 2008/0177235 | A1 | 7/2008 | DiBiasi |
| 2008/0215001 | A1 | 9/2008 | Cowe |
| 2011/0022001 | A1* | 1/2011 | Wei ..................... A61M 5/3287 |
| | | | 604/198 |
| 2011/0071492 | A1 | 3/2011 | Horvath et al. |
| 2011/0106008 | A1 | 5/2011 | Kronestedt |
| 2011/0118667 | A1 | 5/2011 | Zaiken et al. |
| 2011/0270188 | A1 | 11/2011 | Caffey et al. |
| 2011/0301548 | A1 | 12/2011 | Young |
| 2012/0022499 | A1 | 1/2012 | Anderson et al. |
| 2012/0041373 | A1 | 2/2012 | Bruehwiler et al. |
| 2012/0130318 | A1 | 5/2012 | Young |
| 2012/0143144 | A1 | 6/2012 | Young |
| 2012/0265136 | A1 | 10/2012 | Lawlis et al. |
| 2013/0006179 | A1 | 1/2013 | Iwase et al. |
| 2013/0018313 | A1 | 1/2013 | Kramer et al. |
| 2013/0060196 | A1 | 3/2013 | O'Connor et al. |
| 2013/0060233 | A1 | 3/2013 | O'Connor et al. |
| 2013/0123710 | A1 | 5/2013 | Ekman et al. |
| 2013/0218128 | A1 | 8/2013 | Cowe |
| 2013/0253472 | A1 | 9/2013 | Cabiri |
| 2013/0289490 | A1 | 10/2013 | Kemp et al. |
| 2014/0207106 | A1 | 7/2014 | Bechmann et al. |
| 2014/0213975 | A1 | 7/2014 | Clemente et al. |
| 2014/0221936 | A1 | 8/2014 | Edhouse et al. |
| 2014/0343507 | A1 | 11/2014 | Karlsson et al. |
| 2015/0051553 | A1 | 2/2015 | Bjork et al. |
| 2015/0100029 | A1 | 4/2015 | Cowe et al. |
| 2015/0174335 | A1 | 6/2015 | Roervig et al. |
| 2015/0202366 | A1 | 7/2015 | Henderson et al. |
| 2015/0283323 | A1* | 10/2015 | Young ................. A61M 5/3287 |
| | | | 604/182 |
| 2016/0045680 | A1 | 2/2016 | Morris |
| 2016/0175524 | A1 | 6/2016 | Henderson et al. |
| 2016/0271319 | A1 | 9/2016 | Bengtsson et al. |
| 2017/0173304 | A1 | 6/2017 | Teoh |
| 2017/0259011 | A1 | 9/2017 | Nielsen |
| 2018/0021508 | A1 | 1/2018 | Destefano et al. |
| 2018/0064883 | A1 | 3/2018 | Calvert |
| 2018/0185582 | A1 | 7/2018 | Mikkelsen |
| 2018/0339098 | A1 | 11/2018 | Larsen et al. |
| 2018/0353693 | A1 | 12/2018 | Wendland et al. |
| 2018/0353708 | A1 | 12/2018 | Schader et al. |
| 2018/0361069 | A1 | 12/2018 | Schader et al. |
| 2019/0117880 | A1 | 4/2019 | Hirschel et al. |
| 2019/0328968 | A1 | 10/2019 | Giambattista |
| 2020/0297580 | A1 | 9/2020 | Liscio |
| 2020/0405950 | A1 | 12/2020 | Burren et al. |
| 2021/0128817 | A1 | 5/2021 | Bengtsson et al. |

FOREIGN PATENT DOCUMENTS

| | | |
|---|---|---|
| WO | 2010048753 A1 | 5/2010 |
| WO | 2014195183 | 12/2014 |
| WO | 2016/100781 | 6/2016 |
| WO | 2017016986 A1 | 2/2017 |
| WO | 2019112886 A1 | 6/2019 |
| WO | 2021050380 A1 | 3/2021 |

OTHER PUBLICATIONS

Patent Cooperation Treaty International Search Report pertaining to International Application No. PCT/US2020/049434; International Filing Date: Sep. 4, 2020; Date of Mailing: Nov. 16, 2020.
Patent Cooperation Treaty Written Opinion of the International Searching Authority pertaining to International Application No. PCT/US2020/049434; International Filing Date: Sep. 4, 2020; Date of Mailing: Nov. 16, 2020.

\* cited by examiner

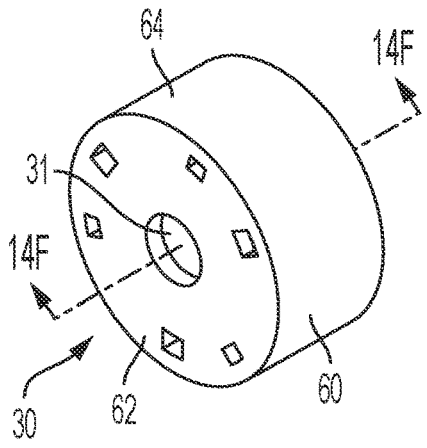
FIG. 14A
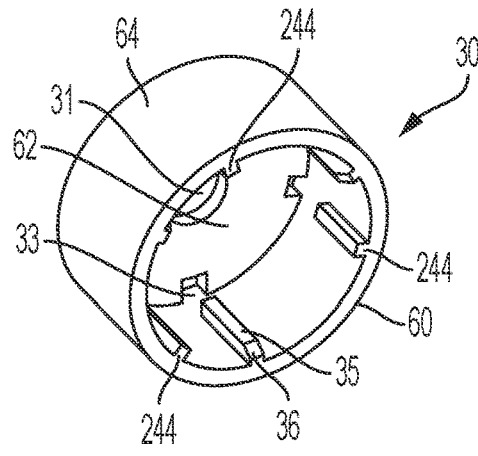
FIG. 14B
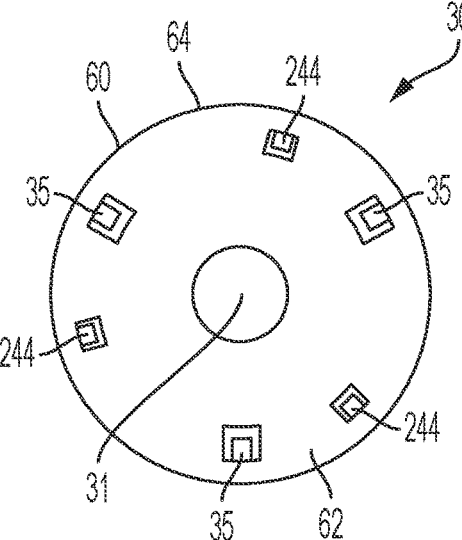
FIG. 14C
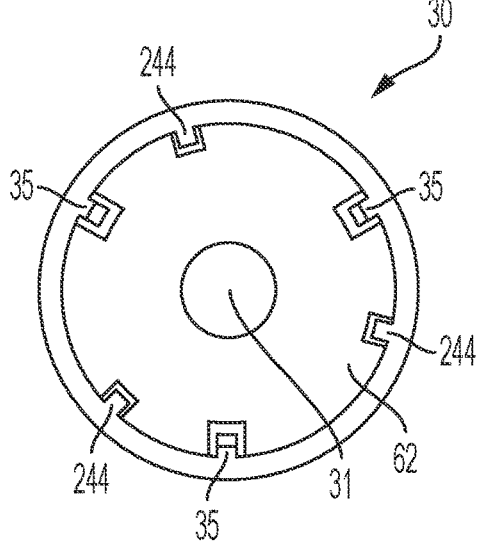
FIG. 14D
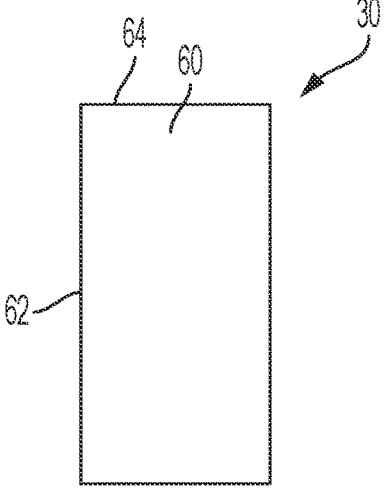
FIG. 14E
FIG. 14F

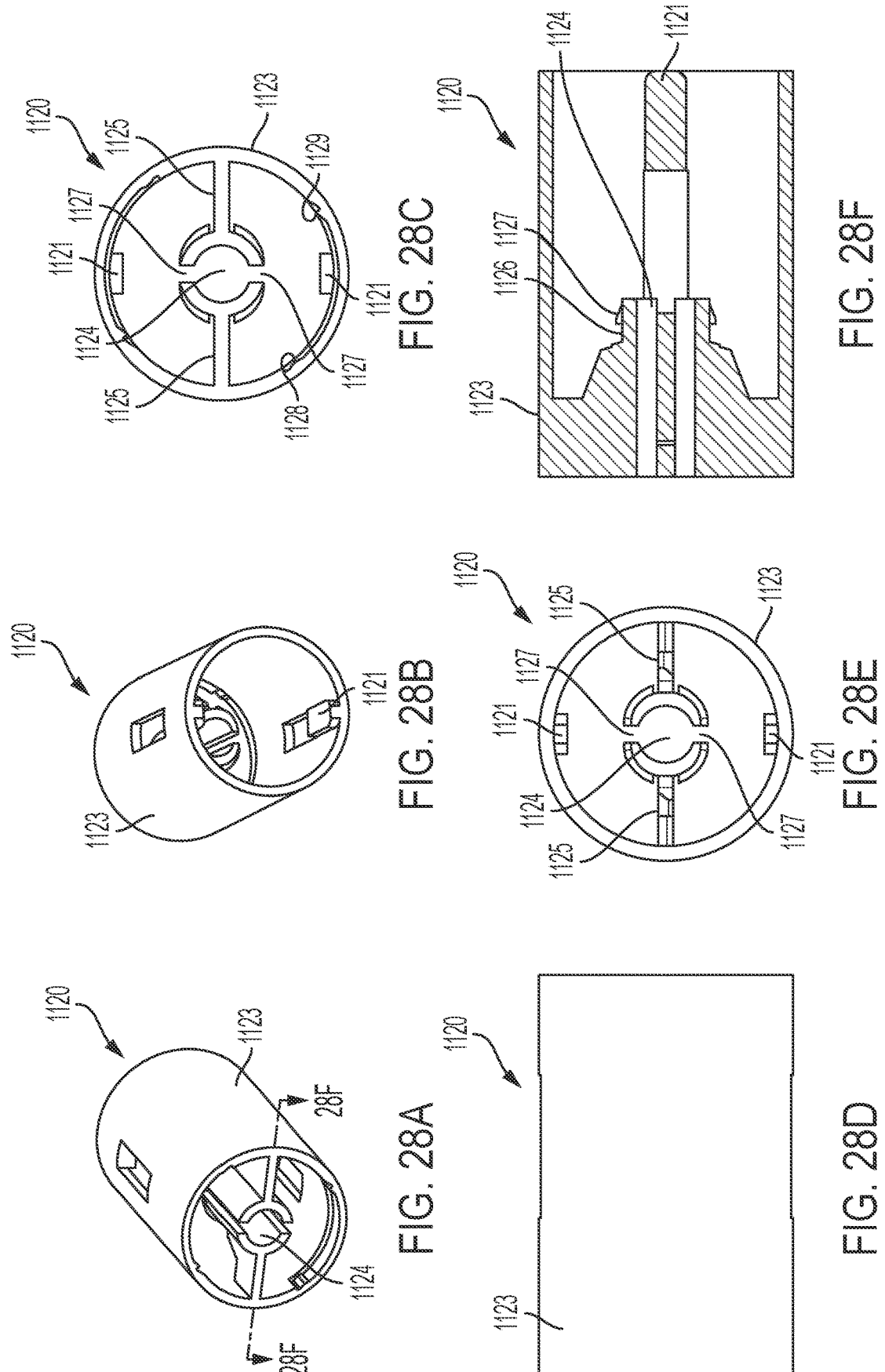

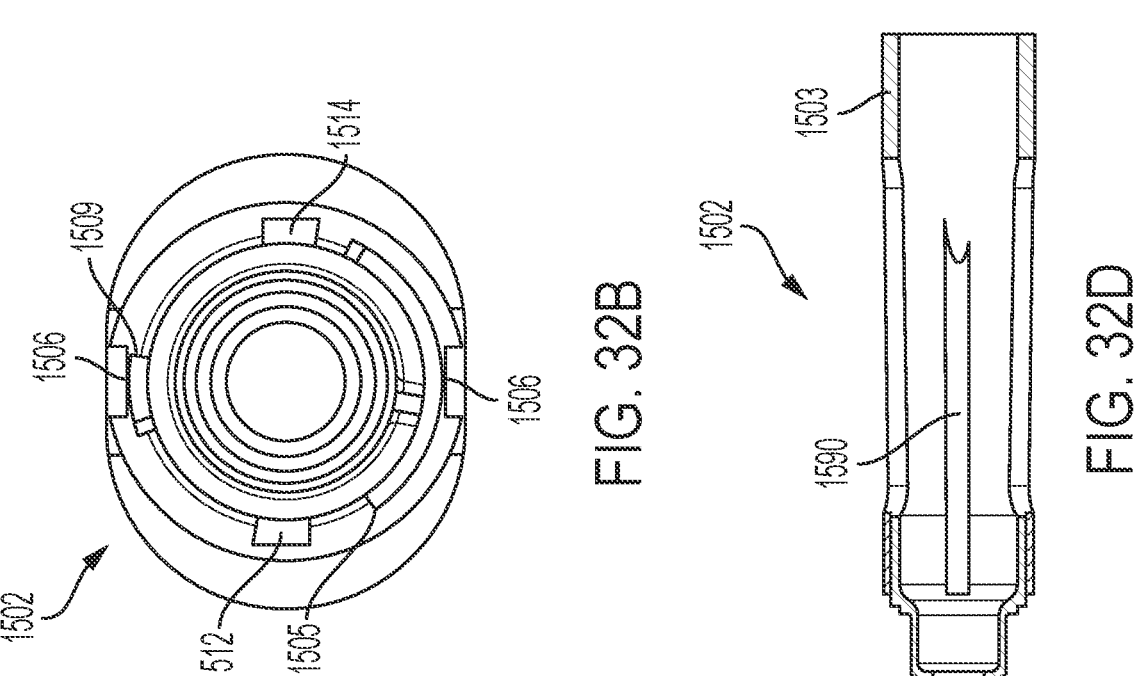
FIG. 32B
FIG. 32D
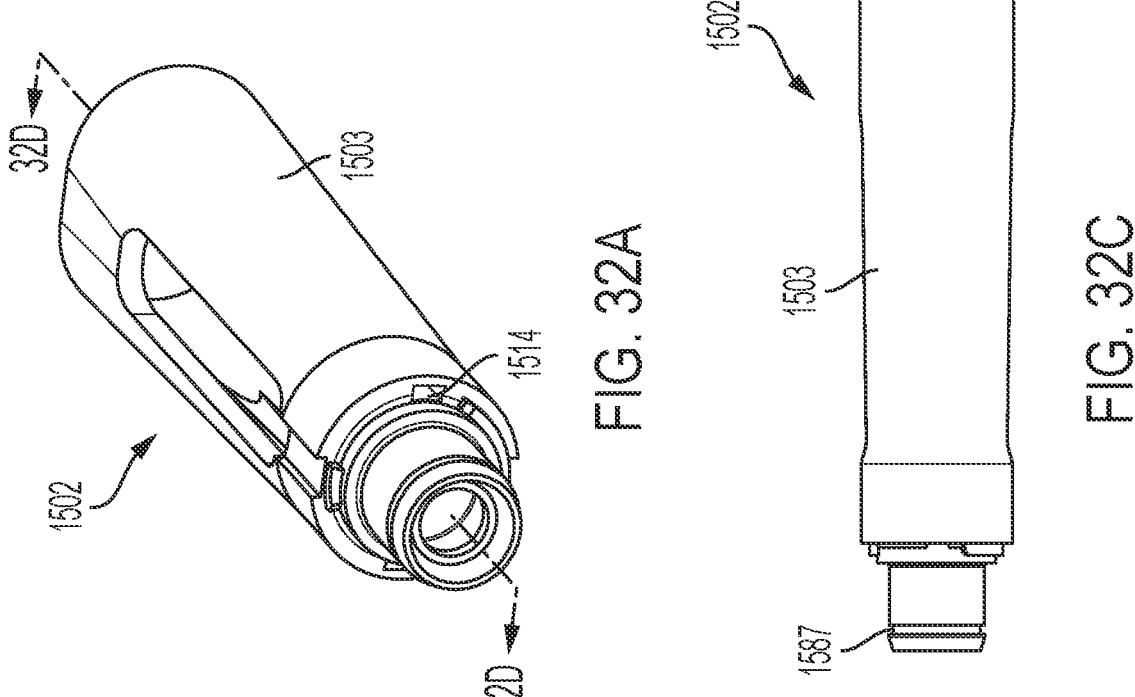
FIG. 32A
FIG. 32C

MEDICATION DELIVERY DEVICE WITH NEEDLE CARRIER

BACKGROUND

Patients suffering from a number of different diseases frequently must inject themselves with medication. To allow a person to conveniently and accurately self-administer medicine, a variety of devices broadly known as injector pens or injection pens have been developed. Generally, these pens are equipped with a medicament container such as a cartridge including a piston and containing a multi-dose quantity of liquid medication. A drive member, extending from within a base of the injector pen and operably connected with mechanisms of the pen that control drive member motion, is movable forward to advance the piston in the cartridge in such a manner to dispense the contained medication from an outlet at the opposite cartridge end, typically through a needle that penetrates a stopper at that opposite end. In disposable or prefilled pens, after a pen has been utilized to exhaust the supply of medication within the cartridge, a user, who then begins using a new replacement pen, discards the entire pen. In reusable pens, after a pen has been utilized to exhaust the supply of medication within the cartridge, the pen is disassembled to allow replacement of the spent cartridge with a fresh cartridge, and then the pen is reassembled for its subsequent use.

The inventors have appreciated that, with some drug delivery devices, a user may be required to attach and/or detach a needle from the drug delivery device prior to and/or after use. The inventors have recognized a need for an arrangement that facilitates attachment and detachment of a needle assembly from the drug delivery device.

SUMMARY

According to one aspect, a drug delivery device is provided. The drug delivery device may include, in some embodiments, a needle assembly including a needle carrier, a needle hub moveable relative to the needle carrier, and a needle coupled to the needle hub. The drug delivery device may also include a drug device having a container with a septum disposed at a container end opening and a carrier drive element. The needle carrier may be coupleable to the drug device. A deployment trigger may be configured to activate the carrier drive element to move the needle hub distally from a retracted needle hub position to an extended needle hub position and to move the needle distally relative to a septum from a retracted needle position to an extended needle position.

According to another aspect, a method is provided. The method may include, in some embodiments, providing a drug device having a container with a septum disposed at a container end opening and a carrier drive element and providing a needle assembly including a needle carrier, a needle hub movable relative to the needle carrier, and a needle coupled to the needle hub. When the needle carrier is coupled to the drug device, the method may further include activating a deployment trigger to activate the carrier drive element to move the needle hub distally from a retracted needle hub position to an extended needle hub position and to move the needle relative to the septum from a retracted needle position to an extended needle position.

According to yet another aspect, a needle assembly for coupling to a drug device having a spring and a container with a septum that includes a fluid is provided. The needle assembly may include, in some embodiments, a needle carrier being removably coupleable to the drug device to load the spring, a needle hub movable relative to the needle carrier, and a needle coupled to the needle hub. Coupling of the needle carrier to the drug device facilitates a piercing of said septum of the drug device with the needle. The needle hub is movable in the distal direction relative to the needle carrier to position a distal end of the needle to extend beyond the needle carrier and a proximal end of the needle to remain within the septum in fluid communication with the fluid of the container.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Additional embodiments of the disclosure, as well as features and advantages thereof, will become more apparent by reference to the description herein taken in conjunction with the accompanying drawings. The components in the figures are not necessarily to scale. Moreover, in the figures, like-referenced numerals designate corresponding parts throughout the different views.

FIGS. 14A-14F depict views of a trigger according to one embodiment;

FIGS. 28A-28F depict views of a needle carrier according to one embodiment;

FIGS. 32A-32D depict views of a portion of a portion of a drug device according to one embodiment.

DETAILED DESCRIPTION

Figures 1A, 1B, 1C, 1D, 1E:
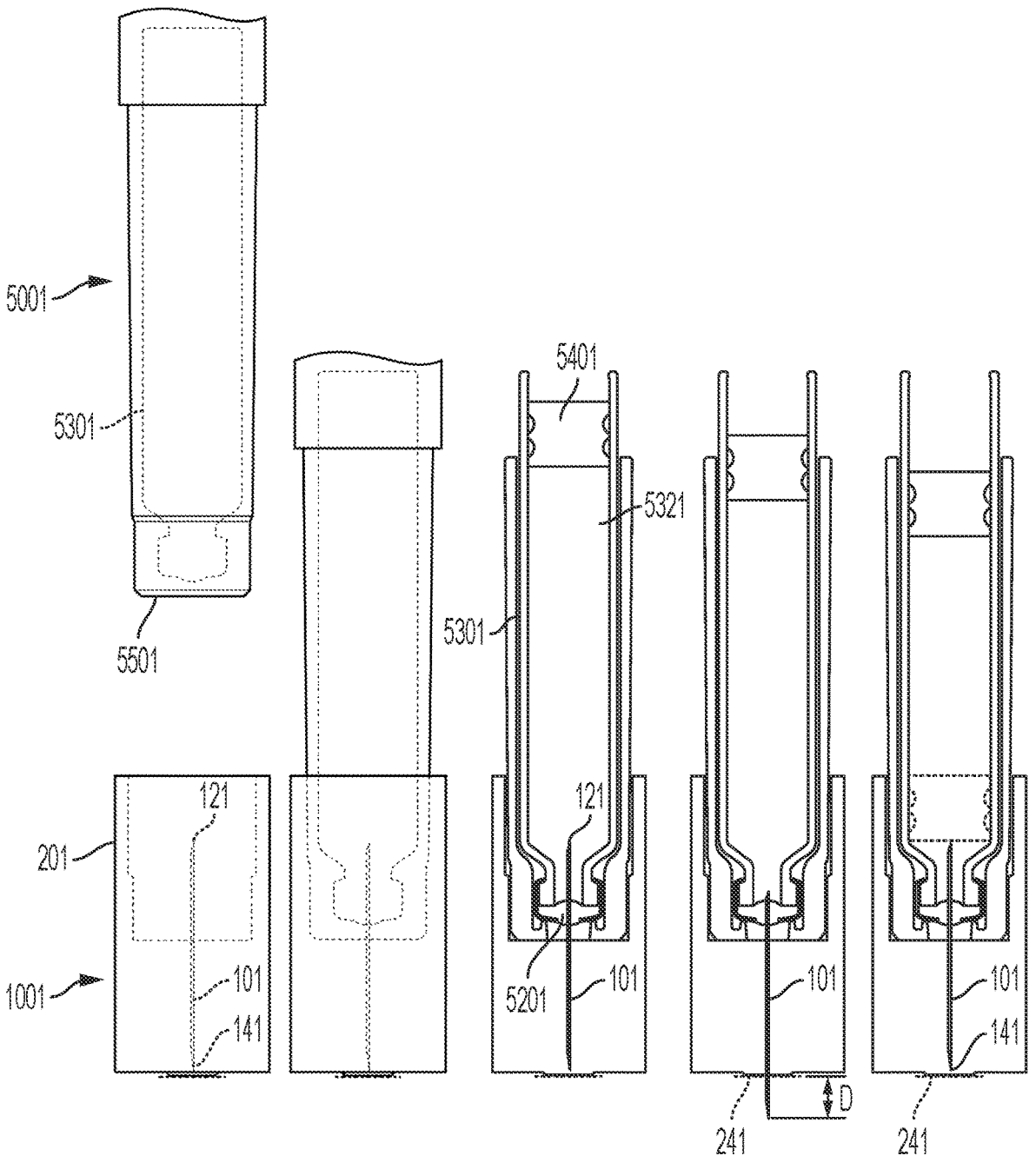
FIGS. 1A-1E depict a series of schematics of a drug delivery device according to one embodiment undergoing a sequence of steps in which a needle assembly is attached to a drug device and a needle is moved in an extension direction.

The present disclosure relates to drug delivery devices having needle assemblies that are removably attachable to another portion of the drug delivery device. This other portion of the drug delivery device will be referred to herein as a drug device, while the combination of the needle assembly with the drug device will be referred to herein as a drug delivery device. A drug device may, in some embodiments, include the portion of the drug delivery device that contains or is configured to contain a medicament.

In one aspect, a needle assembly is configured to be attached to a drug device by a user without requiring the user to contact and/or view the needle of the needle assembly.

In one aspect, a needle assembly includes a needle handling container that can be used to mount the needle assembly to the device, that is subsequently removed from the needle assembly for operation of the device, and then reused as a tool to remove the needle assembly from the device and contain the used needle assembly.

In another aspect, a needle assembly is configured to be removed from a drug device by a user without requiring the user to contact the needle of the needle assembly, and in some embodiments, without requiring the user to view the needle of the needle assembly.

In another aspect, a needle assembly includes a needle handling container that is integrated into the needle assembly, which can be used to mount the needle assembly to the device, that remains with the needle assembly for operation of the device, and then used as a tool to remove the needle assembly from the device and contain the used needle assembly.

As discussed above, in some embodiments, the drug device portion of the drug delivery device may contain a medicament. The term "medicament" refers to one or more therapeutic agents including but not limited to insulins, insulin analogs such as insulin lispro or insulin glargine, insulin derivatives, GLP-1 receptor agonists such as dulaglutide or liraglutide, glucagon, glucagon analogs, glucagon derivatives, gastric inhibitory polypeptide (GIP), GIP analogs, GIP derivatives, oxyntomodulin analogs, oxyntomodulin derivatives, therapeutic antibodies and any therapeutic agent that is capable of delivery by the above device. The medicament as used in the device may be formulated with one or more excipients. The device is operated in a manner generally as described above by a patient, caregiver or healthcare professional to deliver medicament to a person.

For the purposes of promoting an understanding of the principles of the present disclosure, reference will now be made to the embodiments illustrated in the drawings, and specific language will be used to describe the same. It will nevertheless be understood that no limitation of the scope of the invention is thereby intended.

A schematic of a drug delivery device and a sequence of operations of an illustrative embodiment of a drug delivery device is shown in FIGS. 1A-1E. The drug delivery device includes a needle assembly 1001 and a drug device 5001. In this embodiment, the needle assembly includes a needle carrier 201 and a needle 101 having a proximal end 121 and a distal end 141. The drug device 5001 includes a medicament container 5301 and a coupling end 5501 configured to be received by the needle carrier 201 of the needle assembly 1001.

In FIG. 1A, the needle assembly 1001 is in the process of being coupled to the coupling end 5501 of the drug device 5001. The coupling end 5501 of the drug device 5001 is inserted into the needle carrier, resulting in the arrangement shown in FIG. 1B in which the drug device 5001 is coupled to the needle carrier 201. As shown in the cross-sectional view of FIG. 1C, with the drug device 5001 coupled to the needle carrier 201, the proximal end 121 of the needle 101 pierces through a septum 5201 of the medicament container 5301. As also shown in the cross-section of FIG. 1C, the medicament container 5301 also includes an interior 5321 and a piston 5401 that is moveable relative to the interior 5321 and the septum 5201. As appreciated by those skilled in the art, the piston can be moved by various piston-drive device actuators that are conventional in the art.

In the next step in the sequence, shown in FIG. 1D, the needle 101 is moved to an extended position such that a distal end 141 of the needle extends beyond a distal end 241 of the needle carrier 201 by a distance D in order to pierce a subject's skin. As seen in FIG. 1E, the piston 5401 is then driven distally to expel medicament out of the interior 5321 of the medicament container 5301 through the needle 101 and into the subject. In some embodiments, shown in FIG. 1E, the needle 101 may be moveable to a retracted position in which a distal end 141 of the needle is moved to a position proximal to a distal end 241 of the needle carrier 201. In other embodiments, however, the needle remains in an extended position.

FIGS. 2A-2J depict a series of schematics of a drug delivery device according to one embodiment undergoing a sequence of operational steps.

Figures 2A, 2B, 2C, 2D, 2E:
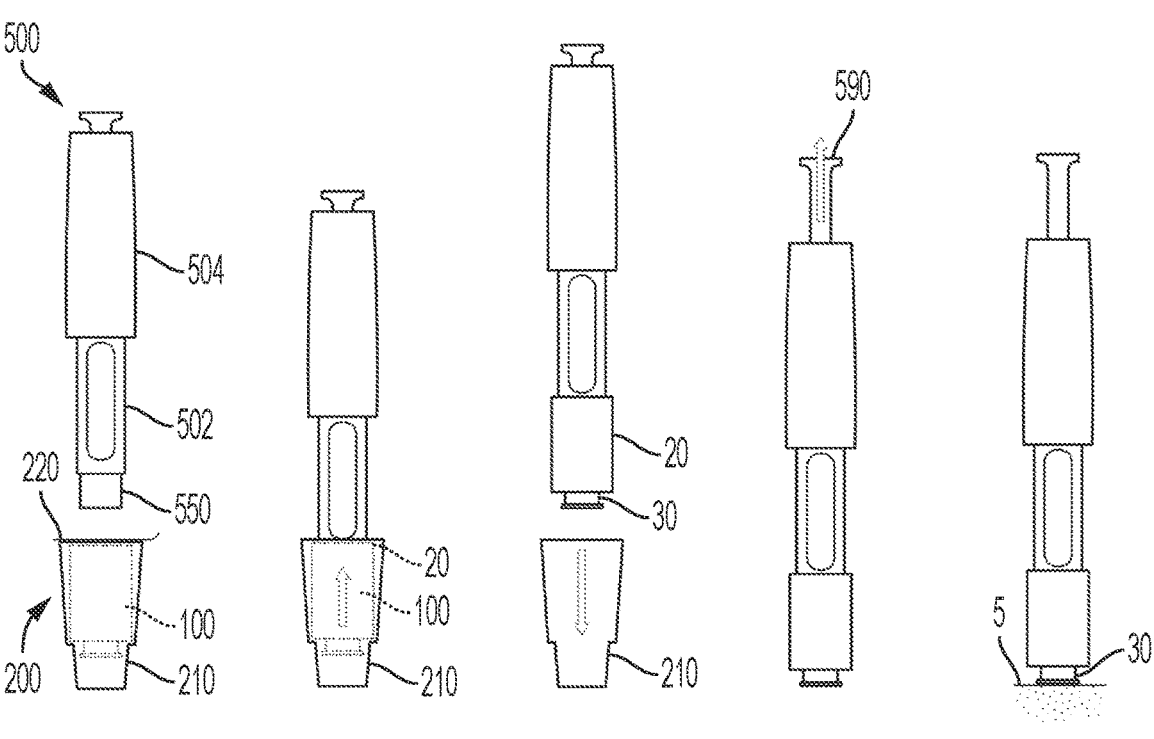
FIGS. 2A-2J depict a series of schematics of a drug delivery device according to one embodiment undergoing a sequence of steps in which a needle assembly is attached to a drug device, a needle is moved in an extension direction to pierce a subject's skin, and the needle assembly is removed from the drug device.

As shown in FIG. 2A, the drug delivery device includes a needle assembly 100 and a drug device 500. In this illustrative embodiment, the needle assembly 100 is initially contained within a container 200 having a body 210 and a cover 220. The drug device may include a first portion 502 and a second portion 504. In some embodiments, the first portion 502 includes a coupling end 550 that is configured to be coupled with the needle assembly 100. In some embodiments, the first portion 502 of the drug device 500 may house a medicament container. In some embodiments, the second portion 504 of the drug device 500 may include a device actuator. In some embodiments, activation of the device actuator serves to expel medicament from the medicament container.

As a first step, the cover 220 is removed from the container body 210 to expose the needle assembly 100 that is located within the container 200. Next, the needle assembly 100 is coupled to the drug device 500. In some embodiments, with the needle assembly 100 positioned within the container body 210, a user couples the carrier 20 of the needle assembly 100 to the drug device 500 by holding the container body 210 and moving the container body toward the coupling end 550 of the drug device 500 until the needle assembly 100 contacts and couples to the drug device 500. As shown in FIG. 2B, the needle assembly 100 may remain within the container body 210 during coupling of the needle assembly 100 to the coupling end 550 of the drug device 500.

Afterwards, as shown in FIG. 2C, with the carrier 20 of the needle assembly coupled to the drug device 500, the container body 210 may be removed from the needle assembly 100 and the drug device 500.

In the next step, shown in FIG. 2D, the drug delivery device may be prepared to deliver a dose of medicament by pulling back on an actuator 590. It should be appreciated, however, that the drug delivery device may utilize other types of actuators and delivery mechanisms that do not require the actuator to be pulled back for dose delivery.

Next, as seen in FIG. 2E, the drug delivery device is placed against a subject's skin 5. In some embodiments, the needle assembly may include a trigger 30 that is placed flush against the skin. The trigger structure may also be a shield around the needle 10 to visually hide the needle from the subject. In some embodiments, the trigger does not actually trigger the needle extension, but is a biased retractable shield and the trigger of the needle extension is performed by another actuation button or movement by the subject.

Figures 2F, 2G, 2H, 2I, 2J:
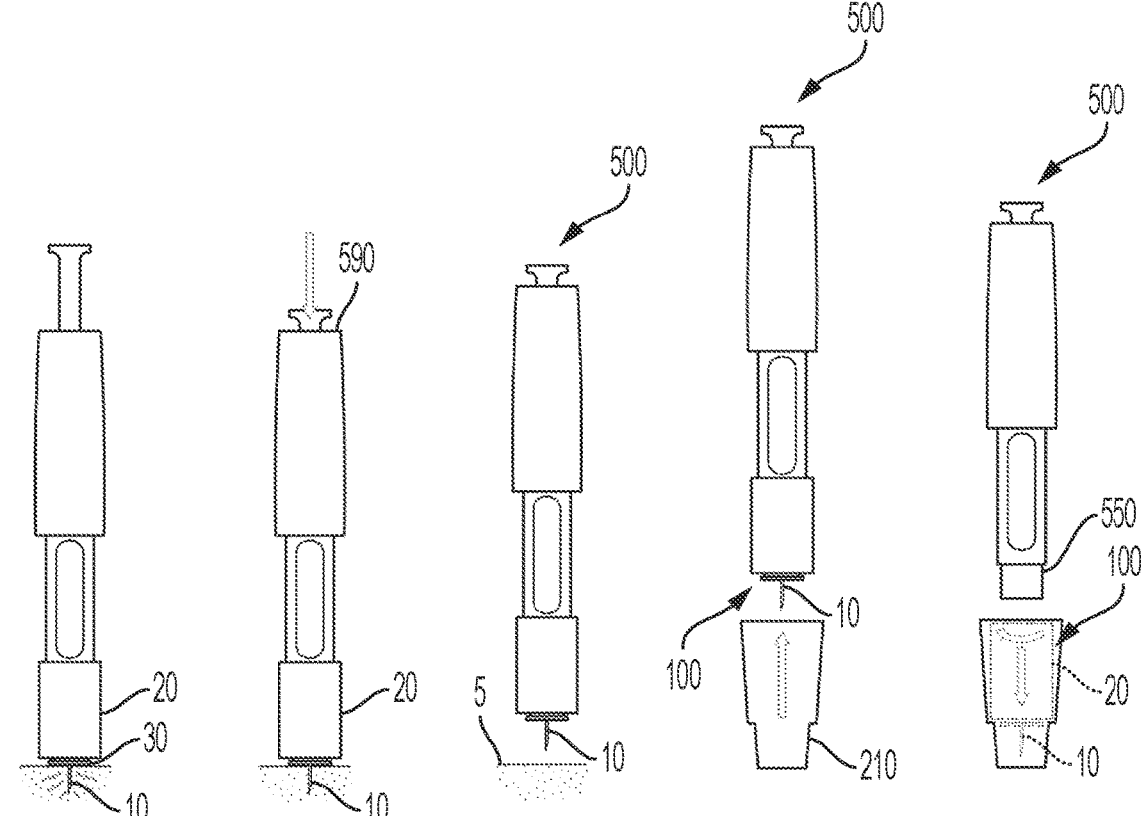

As shown in FIG. 2F, to initiate piercing of the subject's skin, a user may push the drug delivery device down on the user's skin and thus cause the trigger 30 to be pushed into the carrier 20 of the needle assembly, which may actuate extension of needle 10 out of the carrier 20 and into subject's skin 5. Next, as shown in FIG. 2G, a user may push down on the actuator 590 to cause medicament to be expelled from a medicament container within the drug device and out through the needle 10 to inject the medicament into the subject.

As shown in FIG. 2H, after delivery of medicament to the subject, the drug delivery device is removed from the skin 5. As can be appreciated by a review of the sequence of schematics, the trigger 30 may remain retracted within the carrier; however, in other embodiments (not shown), the trigger 30 may return to its extended position by a biasing action once the device is removed from the subject's skin. A user may then begin the process of removing the needle assembly from the drug device 500. In FIG. 2I, the user may push the container body 210 back onto the needle assembly to couple the needle assembly 100 to the container body 210.

As shown in FIG. 2J, to remove the needle assembly from the drug device, the user may turn the container body 210 relative to the drug device to unlock the needle assembly from the coupling end 550 of the drug device, and then pull the container body 210 away from the drug device to remove the needle assembly from the drug device. As shown in FIGS. 2I and 2J, in some embodiments, the needle 10 remains in an extended position during removal of the needle assembly from the drug device. In other embodiments, however, the drug delivery device may include an ability to retract the needle prior to removal of the needle assembly.

Figure 3:
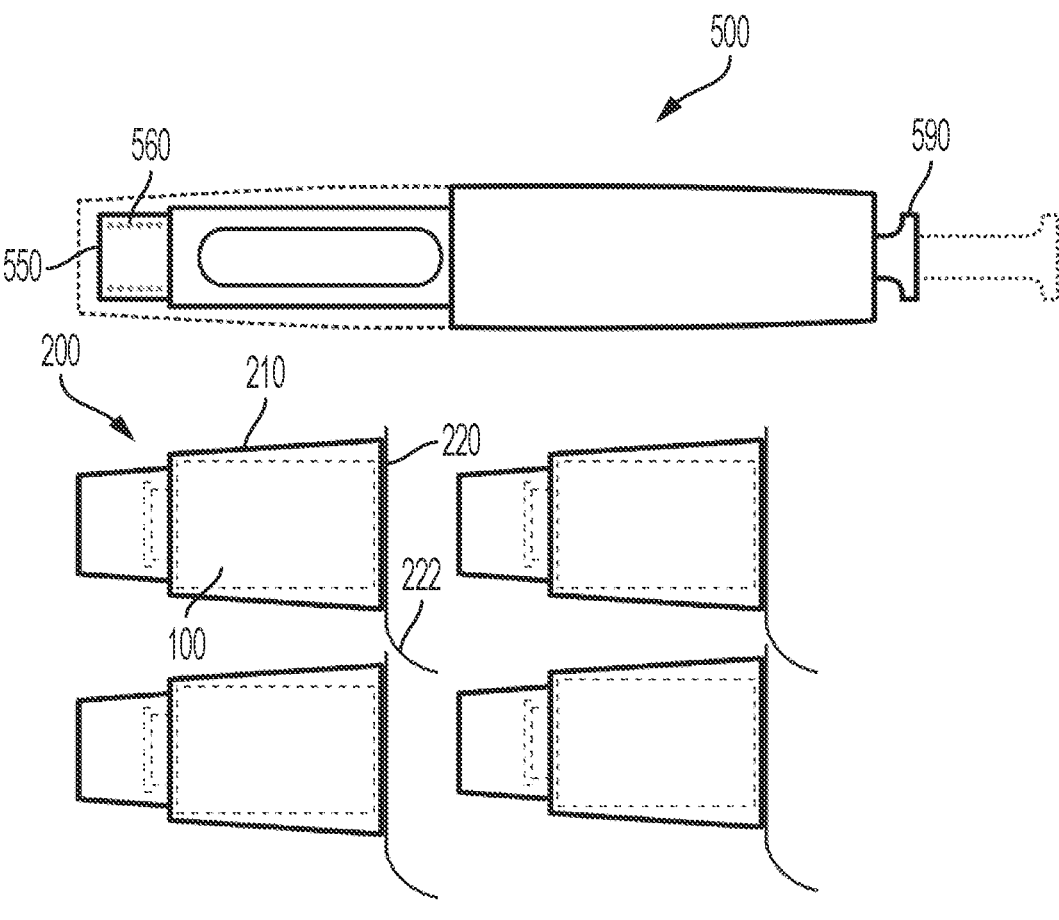
FIG. 3 depicts a schematic of a drug device and a plurality of needle assemblies each contained within individual containers.

In some embodiments, a drug delivery device may be packaged as a kit with a drug device and a plurality of needle assemblies each packaged in their own individual containers. As seen in FIG. 3, a kit may include a drug device 500 having a coupling end 550, an actuator 590, and a needle drive in the form of a drive spring 560. In some embodiments, the spring is a coil spring. In some embodiments, the spring is a torsion spring. In some embodiments, the spring is a leaf spring. In some embodiments, the soring is a bellville washer. In some embodiments, the spring is a wave spring. In some embodiments, the actuator 590 may initiate release of medicament from a medicament container housed within the drug device 500. In some embodiments, the drive spring 560 may play a role in moving a needle of a needle assembly from a retraction position to an extension position, as will be discussed in more detail below. The plurality of needle assemblies 100 may each be contained within individually sealed containers 200 having a container body 210 and a cover 220. In some embodiments, the cover 220 is a peelable seal that may be removably affixed to the container body, e.g. via adhesive. The cover may have a pull tab 222 to facilitate removal. However, other types of covers may be used, such as a cap that engages with the container body, e.g. via threads or other mechanical interlock, or an interference fit. It should also be appreciated that a spring need not be employed and instead a motor, a magnet an elastomeric compound or any other device suitable as a carrier drive element that can impart a motion may be employed, as the present disclosure is not limited in this regard.

Figure 4A:
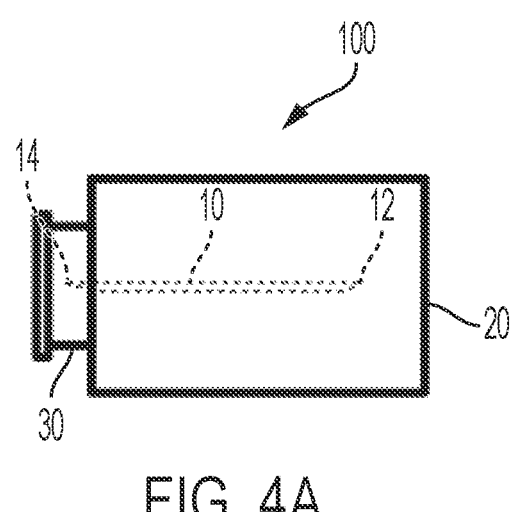
FIGS. 4A-4C depict a series of needle assembly states undergoing a sequence of steps in which a needle begins in a retracted position, is moved to an extended position, and is coupled to a container for removal from a drug device.
Figure 4B:
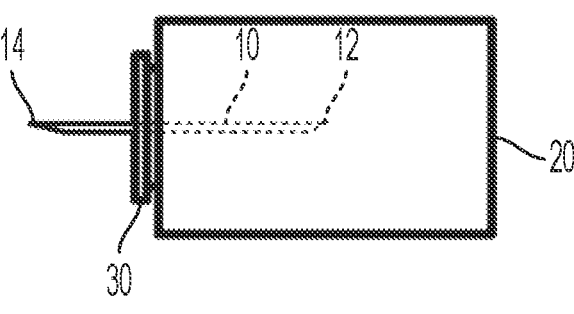
Figure 4C:
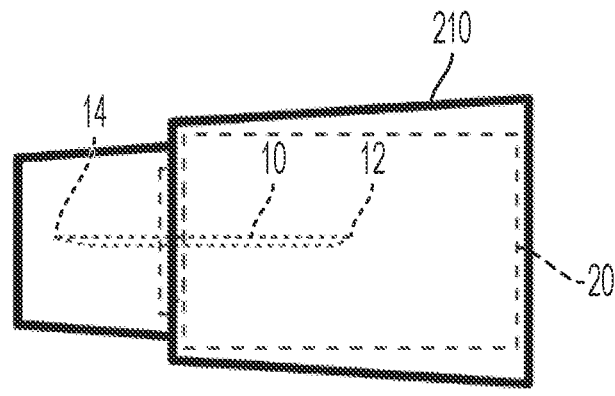

FIGS. 4A-4C depict a series of needle assembly states as the drug delivery device undergoes a sequence of steps. FIG. 4A shows the needle assembly 100 prior to actuation of the needle 10. The trigger 30 is in a protruding position, and the needle 10 is in a retracted position. In some embodiments, the needle assembly is arranged as shown in FIG. 4A when held within a container prior to being coupled to a drug device.

FIG. 4B shows the needle assembly when the needle 10 has been moved to an extended position. As also shown in FIG. 4B, the trigger 30 has been pressed into the carrier 20 in a retracted position.

Finally, FIG. 4C shows the needle assembly moved back into a container body 210 for removal of the needle assembly from the drug device.

Figure 5:
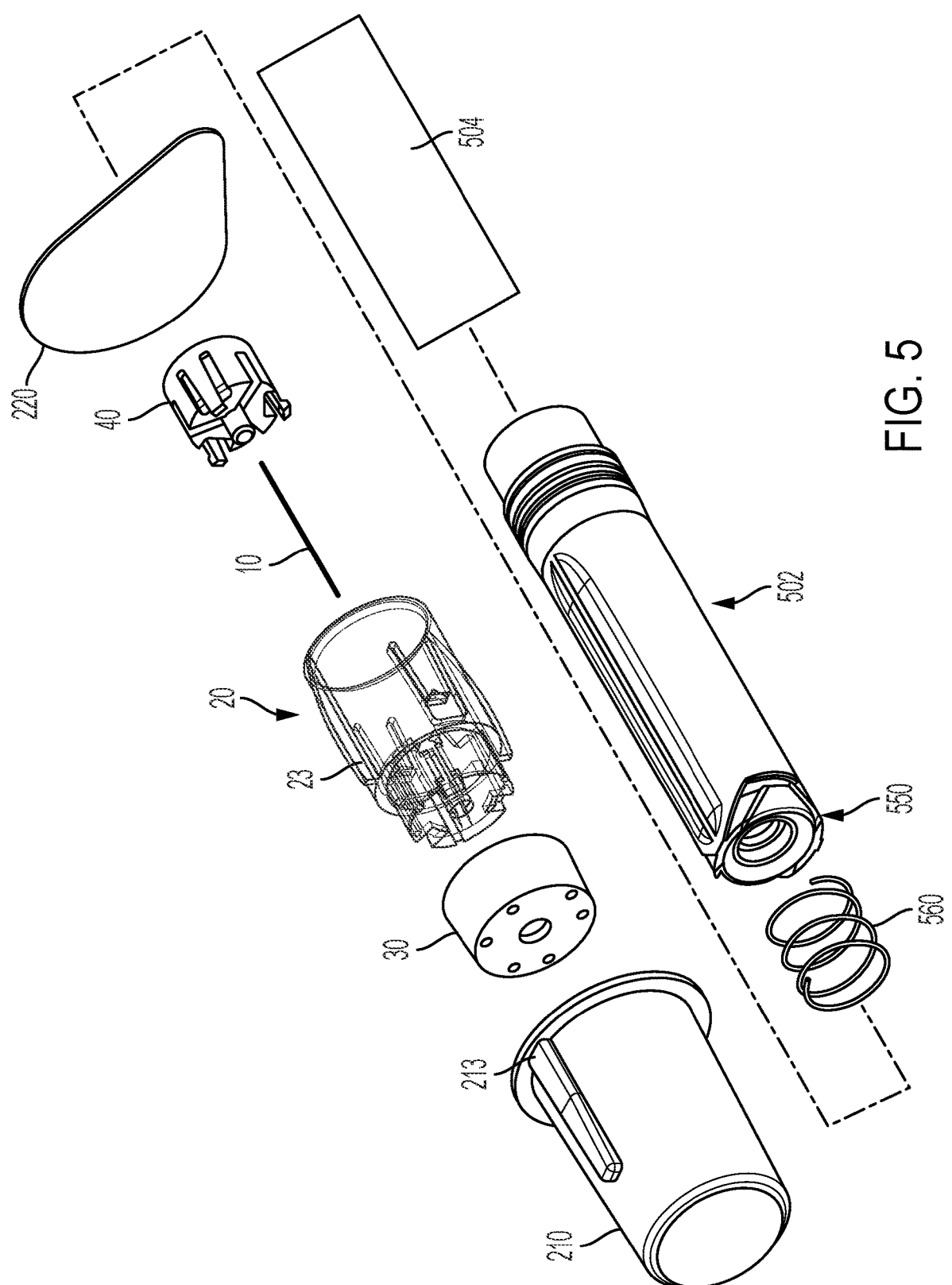
FIG. 5 is an exploded view of a drug delivery device according to one embodiment.

An exploded view of an illustrative embodiment of a drug delivery device is shown in FIG. 5. The drug delivery device includes a needle assembly, including a needle 10, a carrier 20, a trigger 30, and a needle hub 40. The needle assembly is initially housed within a container having a container body 210 and a cover 220. The container body 210 may include a recess 213 formed in the inner wall of the body 210 for receiving a fin 23 on the carrier 20 to enable the needle assembly to couple to the container body 210 when housed within the container body 210. Of course it should be appreciated that a fin may be formed in the inner wall of the body 210 and a corresponding recess may be formed in the carrier 20, as the present disclosure is not limited in this respect. Detailed views of the carrier are provided at FIGS. 11A-11F. Detailed views of the container body 210 are provided at FIGS. 15A-15E.

The drug delivery device also includes a drug device, including a first portion 502 and a second portion 504, which is represented schematically in FIG. 5. In some embodiments, the first portion 502 of the drug device houses a medicament container. In some embodiments, the second portion 504 of the drug devices includes an actuator that, when activated, causes medicament to be expelled from the medicament container.

As will be discussed in detail, in some embodiments, the needle assembly couples to the drug device via the carrier 20 of the needle assembly physically interlocking with a coupling end 550 of the drug device. A drive spring 560 may be disposed in the coupling end 550.

Figure 6A:
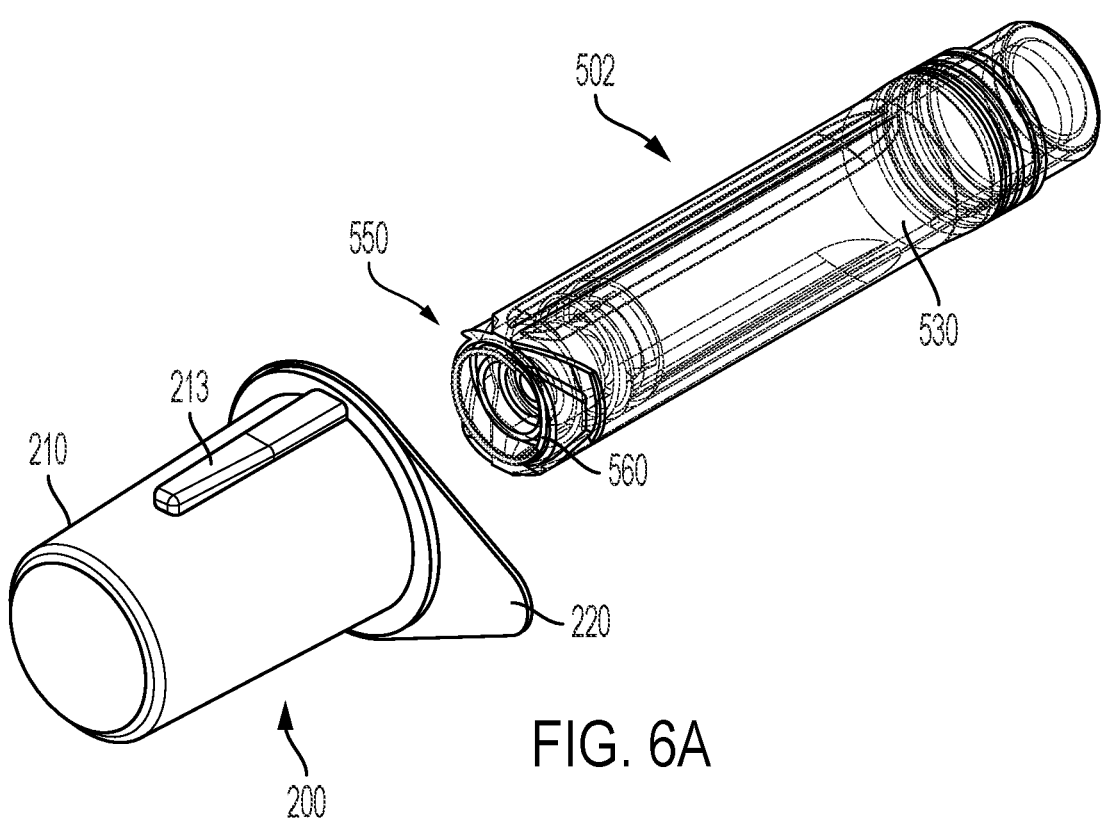
FIG. 6A is a perspective view of a needle assembly being prepared for use with a drug device, the needle assembly being held within a container and a peel tab sealing the needle assembly within the container.
Figure 6B:
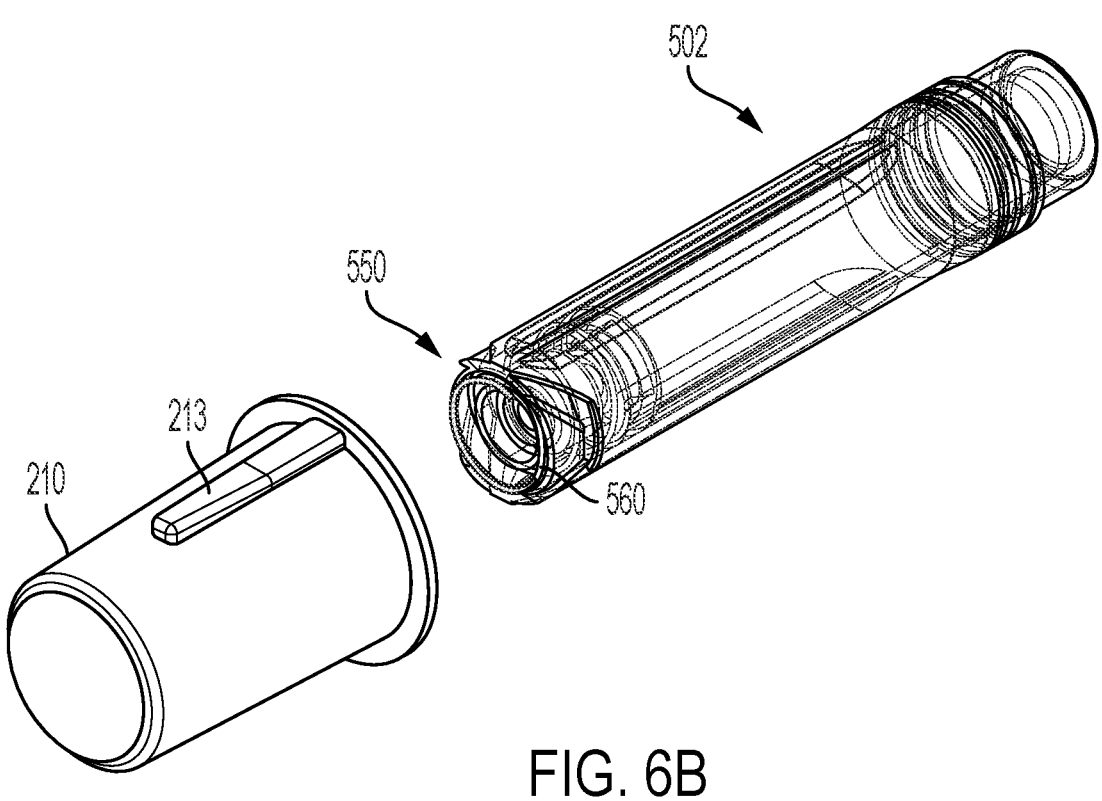
FIG. 6B is a perspective view of the container of FIG. 6B, with the p eel tab removed from the container.

FIGS. 6A-6F depict a sequence of steps illustrating coupling of a needle assembly to a drug device, and extension of a needle. Starting with FIG. 6A, a needle assembly is initially held within a sealed container 200, which includes a container body 210 and a cover 220. Next, as shown in FIG. 6B, the cover 220 is removed from the container body 210, exposing the needle assembly such that the needle assembly can be coupled to a coupling end 550 of a first portion 502 of a drug device. In the illustrative embodiment of FIGS. 6A-6F, the first portion 502 of the drug device includes a medicament container 530 and a drive spring 560 that is also shown in FIG. 5.

Figure 6C:
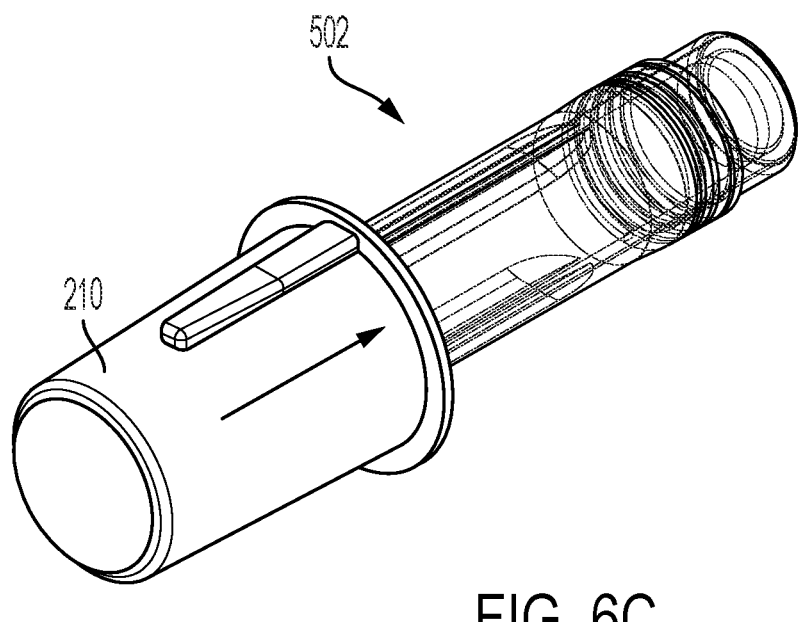
FIG. 6C depicts the container of FIG. 6B being coupled to the drug device.

Next, as shown in FIG. 6C, with the needle assembly held inside the container body 210, the container body is mounted over the coupling end 550 of the first portion 502 of the drug device by pushing the container body 210 onto the coupling end 550, which is hidden in view by the body 210. During this process, the needle assembly inside the container body 210 is coupled to the coupling end 550 of the first portion 502 of the drug device.

Figure 6D:
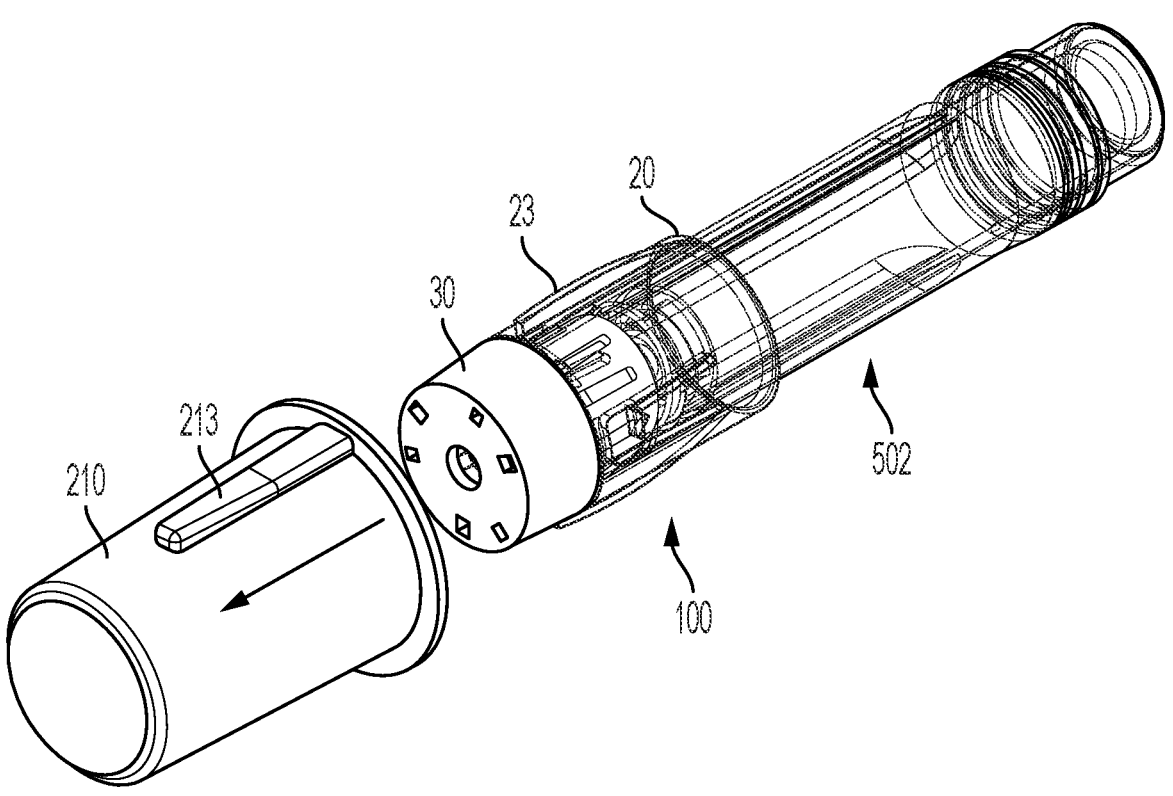
FIG. 6D depicts the container of FIG. 6C removed from the drug device, leaving the needle assembly coupled to the drug device.

As shown in FIG. 6D, the container body 210 is removed from the needle assembly 100, leaving the needle assembly 100 coupled to the first portion 502 of the drug device. In this illustrative embodiment, the container body 210 may be used as a tool to couple the needle assembly to the drug device by pushing the container body 210 straight onto the drug device, as will be discussed further in relation to FIG. 8A. The container body 210 is then removed from the needle assembly 100 by pulling the container body 210 straight off of the drug device and the needle assembly. In some embodiments, no relative twisting between the container body and the needle assembly and/or the drug device is needed for coupling of the needle assembly to the drug device and/or removal of the container body from the needle assembly. In other embodiments, however, a relative twisting motion may be used.

Figures 6E, 6F:
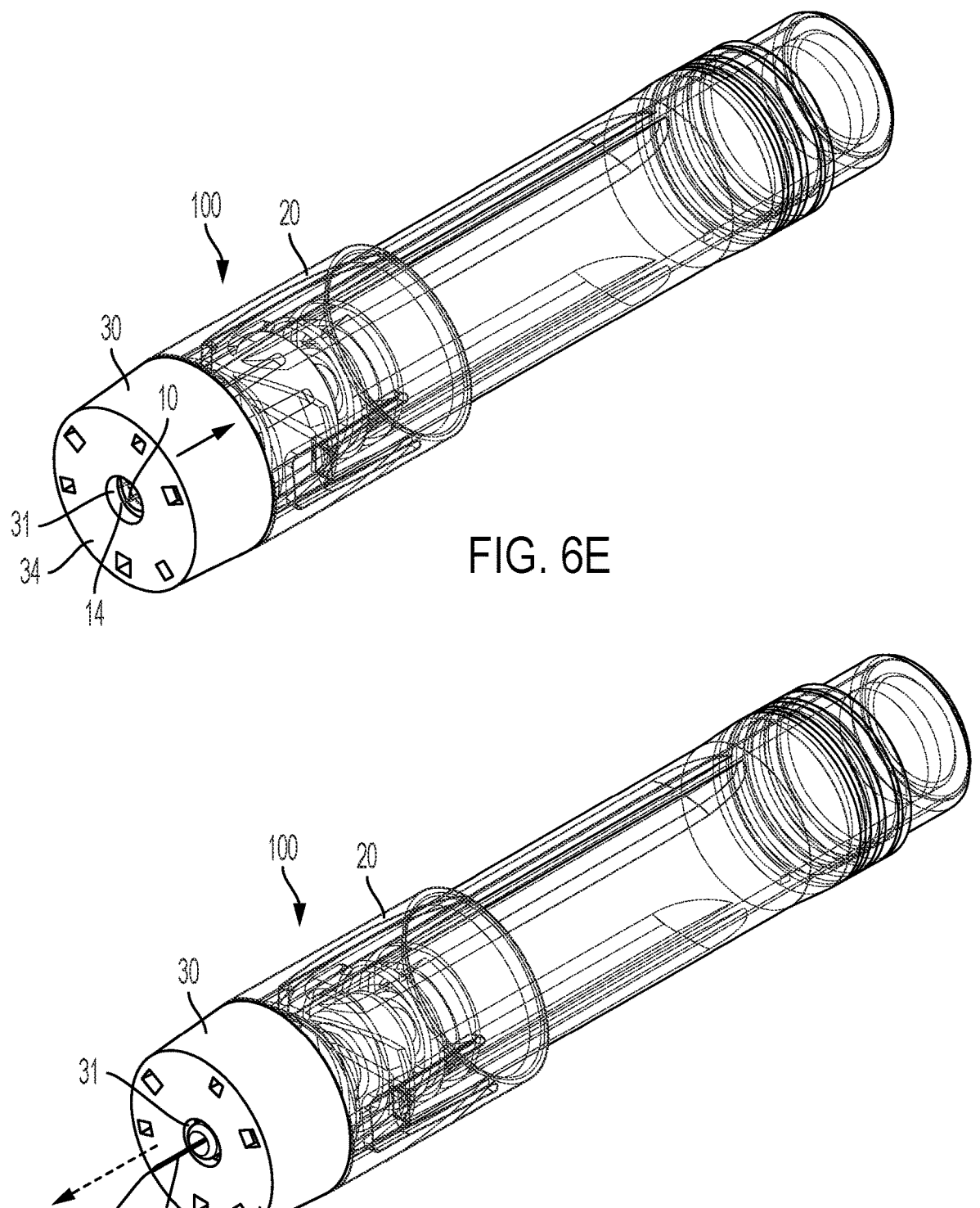
FIG. 6E depicts a trigger of the needle assembly being pushed in a proximal direction to actuate extension of a needle of the needle assembly.
FIG. 6F depicts the needle of FIG. 6E moved to an extended position.

In FIG. 6E, with the container body removed, the needle assembly 100 can be seen. The needle assembly 100 includes a carrier 20 and a trigger 30 mounted to the end of the carrier 20. The needle assembly 100 also includes a needle 10, where at least a portion of the needle is positioned within the carrier 20. At least a portion of the needle may be positioned within a bore 31 of the trigger 30. Initially, the needle is in a retracted position in which a distal end 14 of the needle does not extend beyond a distal end 34 of the trigger 30.

To actuate extension of the needle, a force is exerted upon the trigger 30 in a proximal direction, as represented by the arrow shown in FIG. 6E. This force may be created, for example, by pressing the trigger 30 flush against the skin of a subject. Pushing on this trigger actuates the needle 10 to move distally to an extended position, shown in FIG. 6F. In the extended position, the distal end 14 of the needle 10 has moved out of the bore 31 of the trigger, and instead is positioned distal to the distal end 34 of the trigger 30.

Figure 7A:
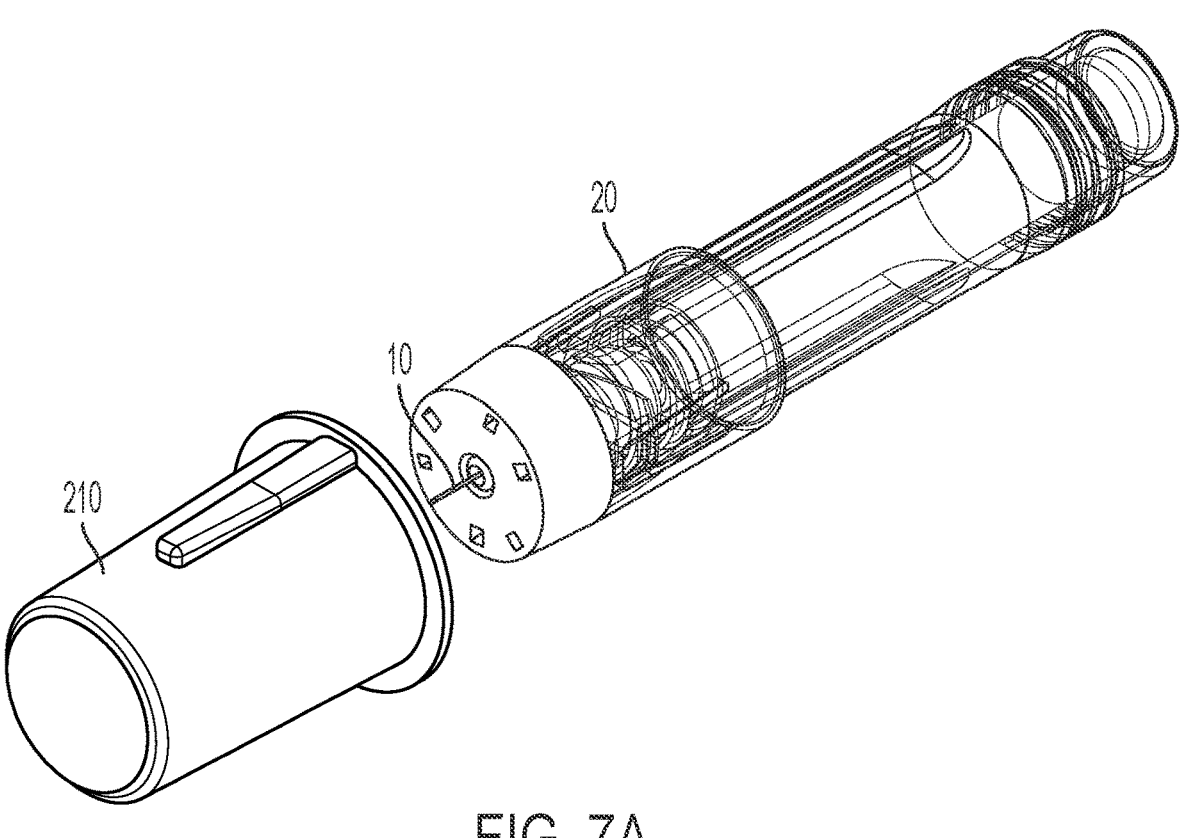
FIG. 7A depicts a container being coupled to the needle assembly for removal of the needle assembly from the drug device.
Figure 7B:
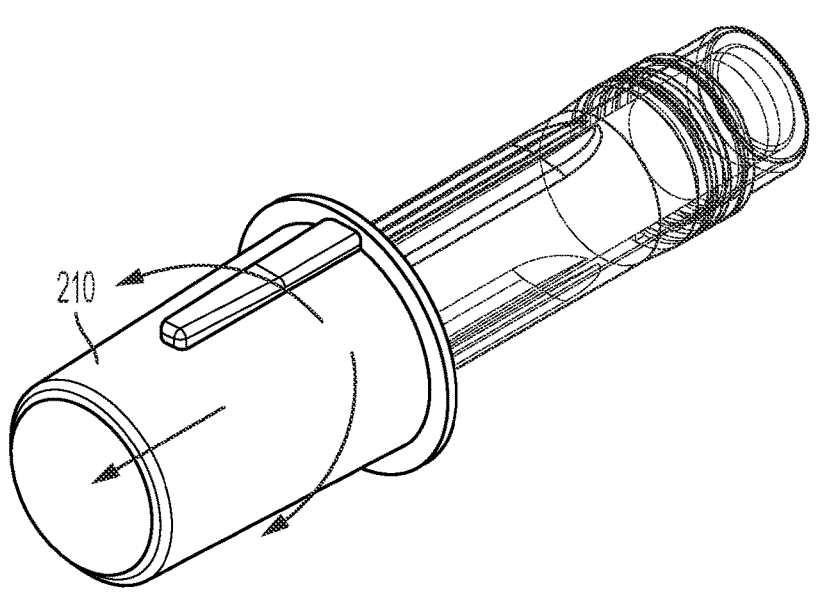
FIG. 7B depicts the container being manipulated to remove the needle assembly from the drug device.

Finally, FIGS. 7A and 7B illustrate removal of the needle assembly from the drug device. As shown in FIG. 7A, with the needle 10 still in the extended position, a user moves the container body 210 toward the needle assembly until the needle assembly is received within the container body 210. To unlock the needle assembly from the drug device, a user twists the container body 210 in either direction relative to the drug device. Then, to remove the needle assembly from the drug device, the user pulls the container body 210 straight off and away from the drug device.

Figure 8A:
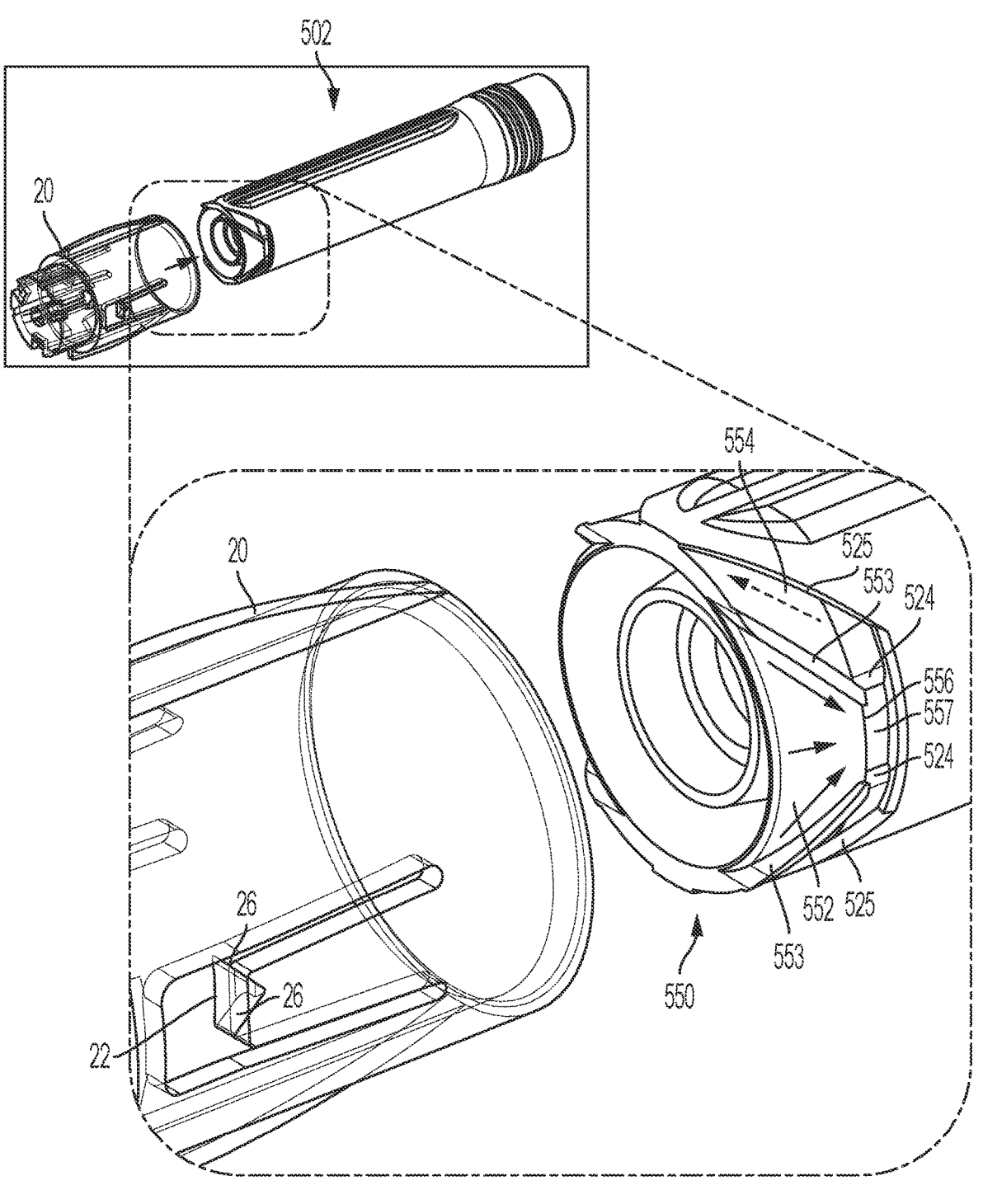
FIG. 8A depicts a detailed view of a carrier of a needle assembly in the process of being coupled to a first portion of a drug device.

A detailed view of the coupling end of the drug device and the carrier of the needle assembly is shown in FIG. 8A, with the carrier shown in phantom. The carrier 20 includes pawls 22 that interact with the coupling end 550 of the drug device. When pushing the carrier 20 axially onto the coupling end 550, the pawl 22 moves into an on-ramp 552 of the coupling end 550 until the pawl 22 snaps over a snap edge 556 and into a recess 557 to lock the carrier 20 onto the drug device. The recess is defined in the sidewall of the device and has a distal boundary defined by the snap edge 556, a proximal boundary defined by the device body, and a pair of circumferential boundaries defined by bumps 524. The wall thickness of the coupling end varies in a manner such that there may be only clearance for pawls 22 to enter the on-ramps and thus into a coupling arrangement at certain angular orientations.

If, during initial placement of the carrier onto the drug device, the carrier is not in the correct rotational orientation relative to the drug device, the pawl 22 may be guided by the protruding sides 553 of the on-ramp 552 to rotate the carrier toward an aligned position relative to the drug device. The sides 553 are shown in a tapering arrangement. Pawl flanks 26 of the pawl 22 may slide against the sides 553 of the on-ramp 552 during mounting of the carrier 20 to the coupling end 550. The sides 553 may act as a funnel that defines a narrowing width of the on-ramp in a direction toward the snap edge 556 and the recess 557.

Figure 8B:
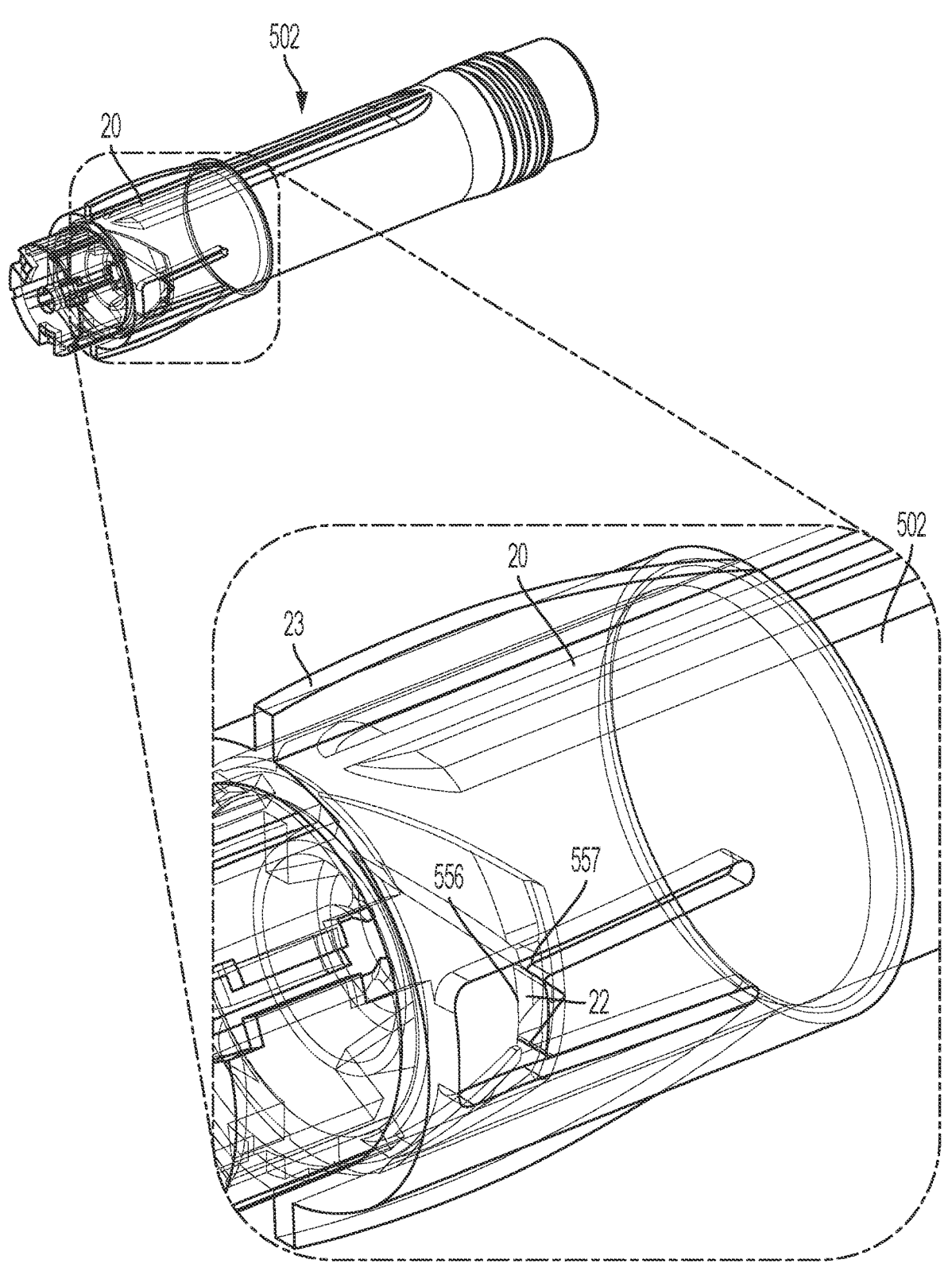
FIG. 8B depicts the carrier of FIG. 8A coupled to a first portion of a drug device.

FIG. 8B depicts the carrier 20 coupled to the drug device. The pawl 22 has snapped over the snap edge 556 and into recess 557 to rotationally and axially lock the carrier 20 to the drug device.

Figures 9A, 9B, 9C:
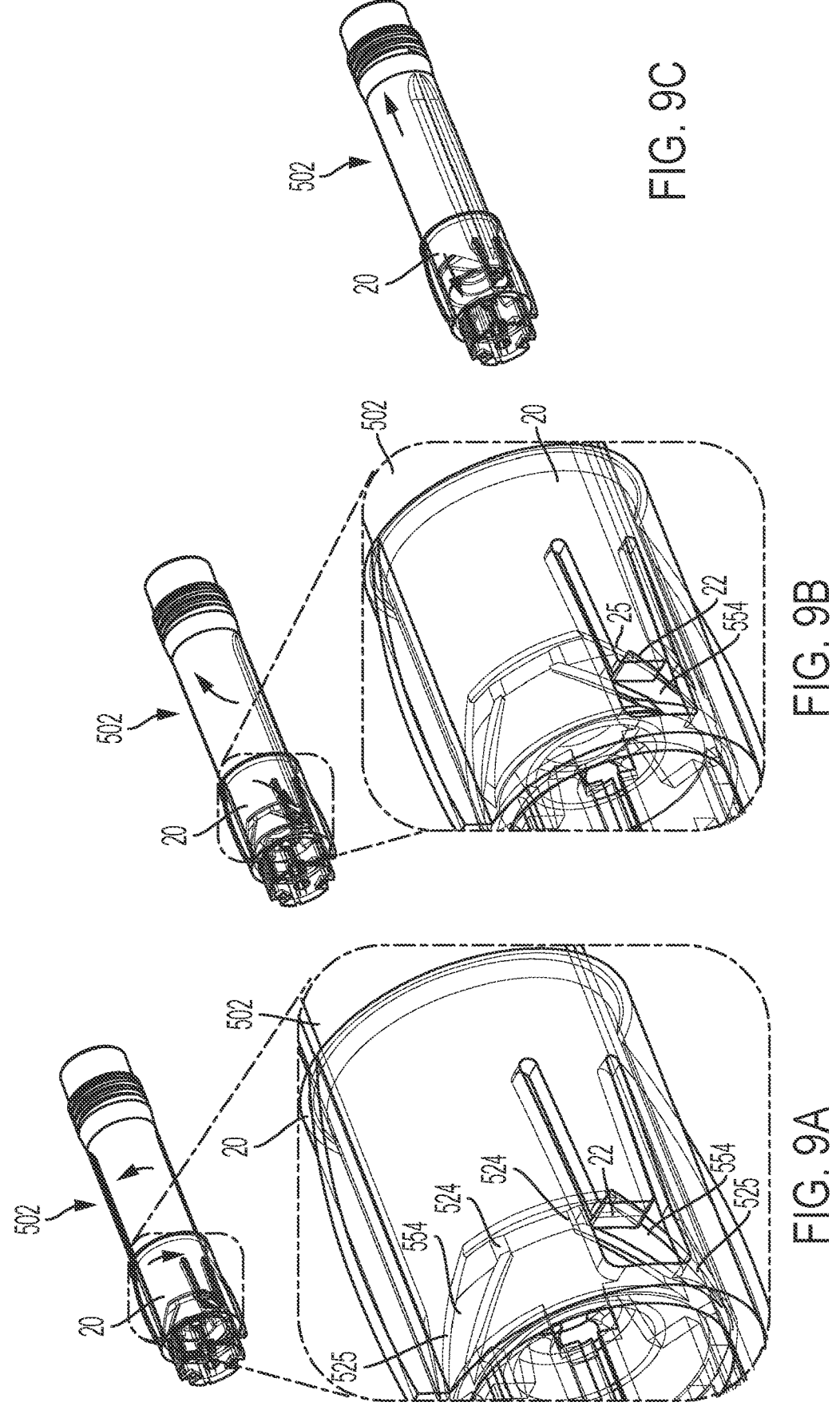
FIGS. 9A-9C depict the carrier of FIG. 8A in the process of being removed from the first portion of the drug device.

FIGS. 9A-9C depict the carrier in the process of being removed from the first portion of the drug device. As shown in FIG. 9A, to remove the carrier 20 from the first portion 502 of the drug device, the parts are twisted relative to one another. The carrier pawls 22 first climb up removal bumps 524 on the drug device. Sliding of the carrier pawls 22 against the removal bumps provides a detent feel. The pawls 22 then encounter and enter off-ramps 554 of the drug device. Continued relative twisting causes the carrier pawls to slide along the helical sides 525 of the off-ramps (FIG. 9B), resulting in separation of the carrier from the drug device (FIG. 9C). The radial elevation of the off-ramps 554 may be greater than the elevation of the on-ramps Detailed views of the carrier are provided at FIGS. 11A-11F. Detailed views of the first portion of the drug device and its coupling end are provided at FIGS. 12A-12E.

Figures 10A, 10B:
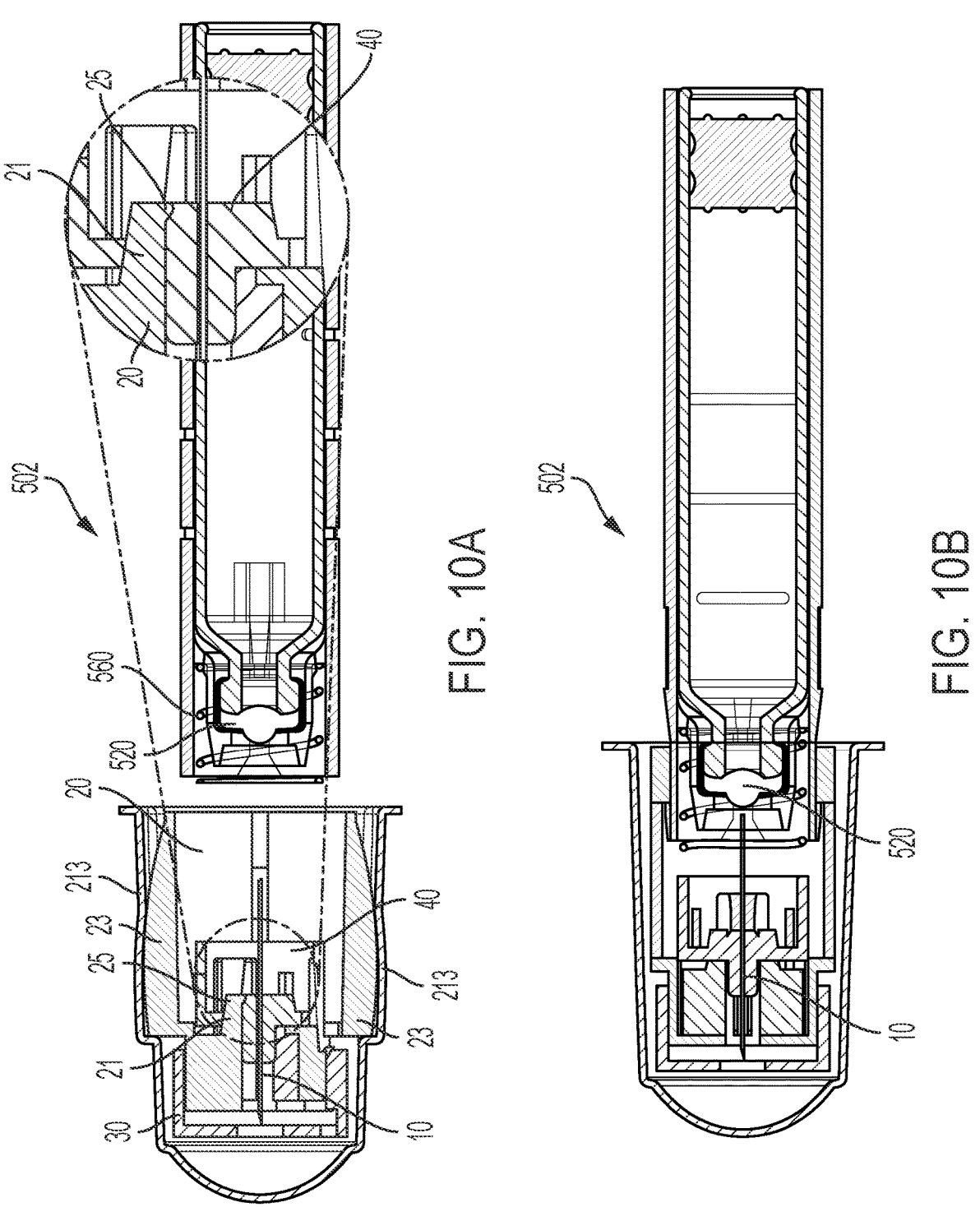
FIGS. 10A-10C depict cross-sectional views of a needle assembly being coupled to a first portion of a drug device.
Figure 10C:
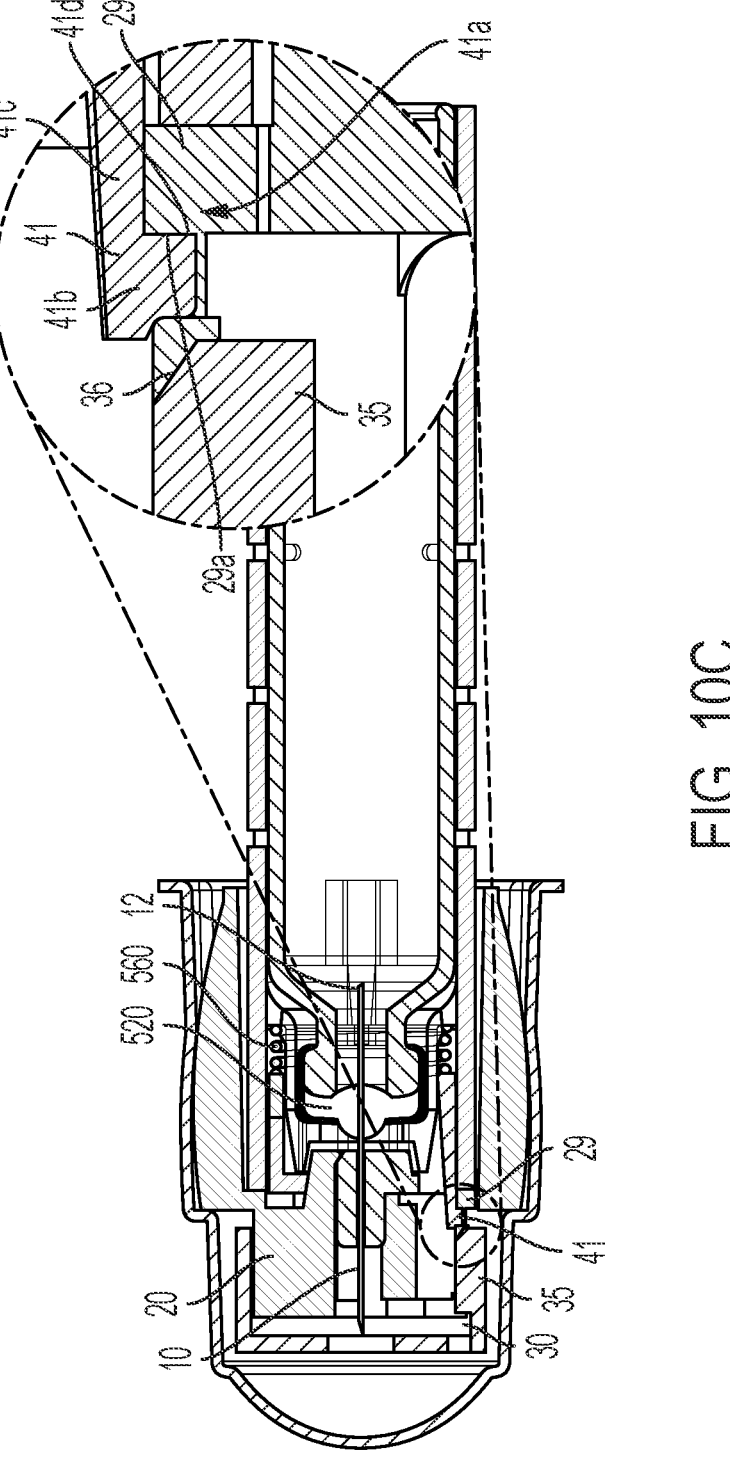

Operation of the drug delivery device will now be described via a sequence of cross-sectional views. FIG. 10A-10C depict cross-sectional views of a needle assembly being coupled to a first portion of a drug device. As shown in FIG. 10A, the needle assembly, which includes a carrier 20, trigger 30, needle hub 40 and needle 10, is initially housed within the container body 210. The carrier 20 includes fins 23 that are received within recesses 213 of the container body 210. The carrier also includes axial guide ribs 21 with radial tips 25 that initially retain the needle hub 40 prior to use.

In FIG. 10B, the carrier 20 has been pushed onto the first portion 502 of the drug device to engage and align the carrier to the first portion 502 of the drug device. At this stage, where the needle carrier 20 has not yet fully engaged the drug device, the needle 10 has not yet entered the septum 520 of the drug device.

As the needle carrier 20 is further pushed onto the drug device into a fully engaged position, as shown in FIG. 10C, the proximal end 12 of the needle 10 pierces through the septum 520 of the drug device. As shown in the enlarged view of FIG. 10C, the trigger 30 includes a rib 35 that interacts with legs 41 of the hub 40, as will be discussed below. Engagement of the carrier 20 to the drug device also axially compresses a drive spring 560 located on the drug device against the trigger 30, also referred to as loading the spring. The spring 560 remains compressed due to engagement of the carrier 20 to the drug device, and due to the needle hub being initially locked to the carrier. As shown in the enlarged view of FIG. 10C, the legs 41 are engaged to ledges 29 of the carrier. More specifically, each of the legs 41 includes a notch region 41a defined by a radial portion 41b extending outward from an axial leg portion 41c. A catch surface 41d is therefore formed that engages exterior surface 29a of a ledge 29. Accordingly, the exterior surface 29a is sized to fit within the not 41a to facilitate a fixed position prior to deployment. It should be appreciated that in some embodiments, engagement of the carrier 20 to the drug device need not load the drive spring 560.

Figure 10D:
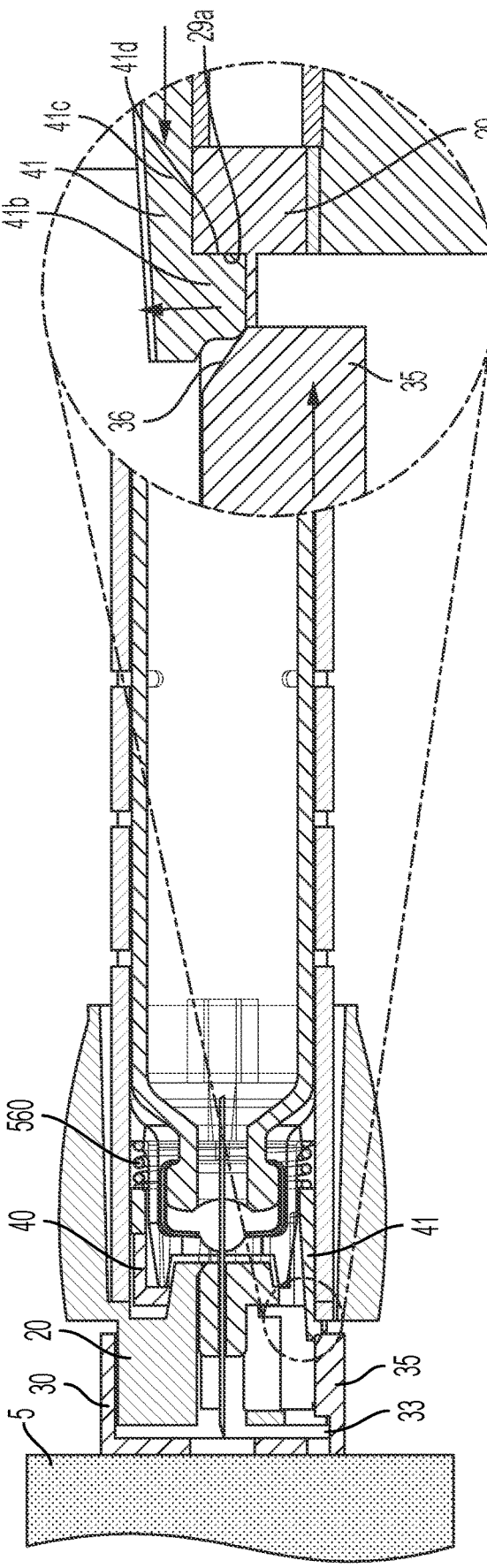
FIG. 10D depicts a trigger of the needle assembly of FIG. 10A being pressed against a subject's skin to actuate extension of a needle.
Figure 10E:
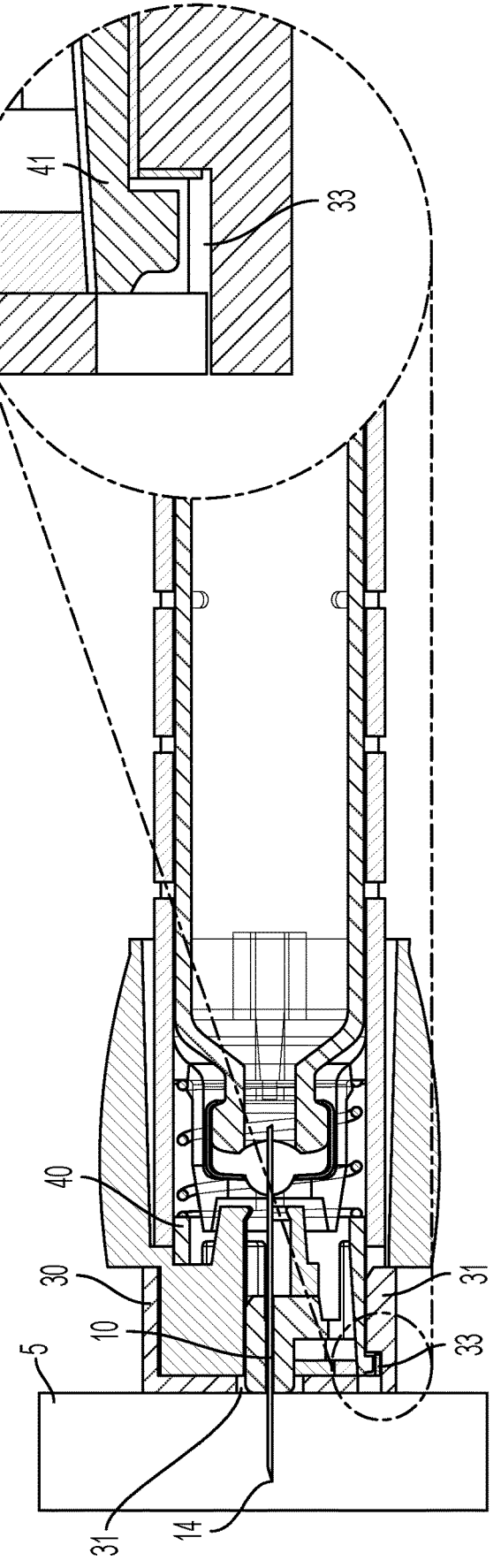
FIG. 10E depicts extension of the needle of FIG. 10D into the subject's skin.

Next, FIG. 10D shows the trigger 30 of the drug delivery device being pushed against skin 5 of a subject. As a result, the trigger 30 moves in a proximal direction toward the needle carrier 20. As shown in the enlarged view in FIG. 10D, movement of the trigger in the proximal direction causes a contact surface 36 of the trigger rib 35 to contact and push against a hub leg 41 of the needle hub 40, thus moving the hub leg 41 radially inward until the hub leg clears the inner surface of the rib 35 and releases from a ledge 29 of the carrier 20, thus freeing the needle hub 40 to be moveable relative to the carrier 20. With the needle hub 40 free to move distally relative to the carrier 20, the spring 560, which had been exerting a force against the needle hub, is free to axially expand and release its stored potential energy, pushing the needle hub 40 to move distally relative to the carrier, as shown in FIG. 10E. The needle 10, which is attached to the needle hub 40, moves distally together with the needle hub into an extension position in which the distal end 14 of the needle 10 moves through the bore 31 of the trigger 30 and pierces into the subject's skin 5.

As shown in the enlarged view of FIG. 10E, in some embodiments, distal movement of the needle hub causes the needle hub legs 41 to move toward and into radial recesses 33 in the interior of trigger 30, locking the hub 40 to the trigger 30. In some embodiments, with the needle hub locked in place, the needle cannot be redeployed.

Detailed views of the needle hub are provided at FIGS. 13A-13E. Detailed views of the trigger are provided at FIGS. 14A-14F.

Figure 10F:
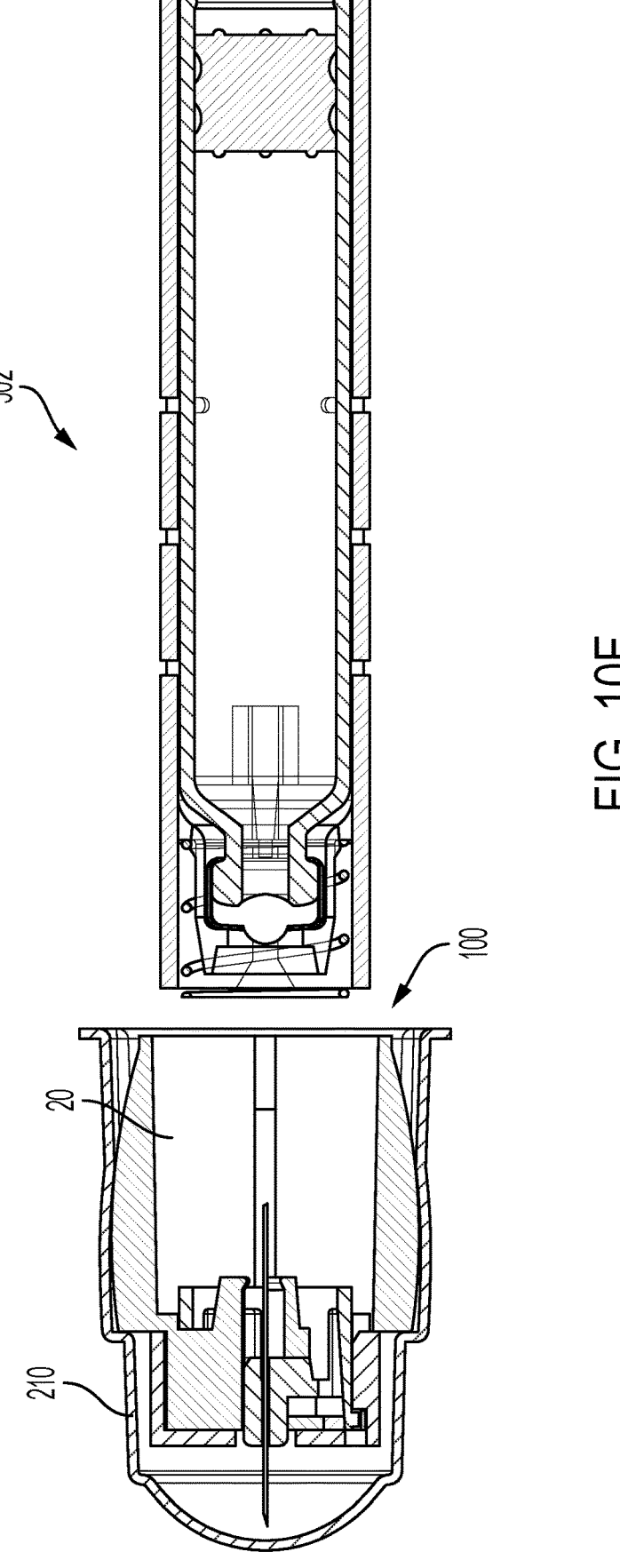
FIG. 10F depicts removal of the needle assembly from the drug device using a container body.
Figures 11A, 11B, 11C, 11D, 11E, 11F:
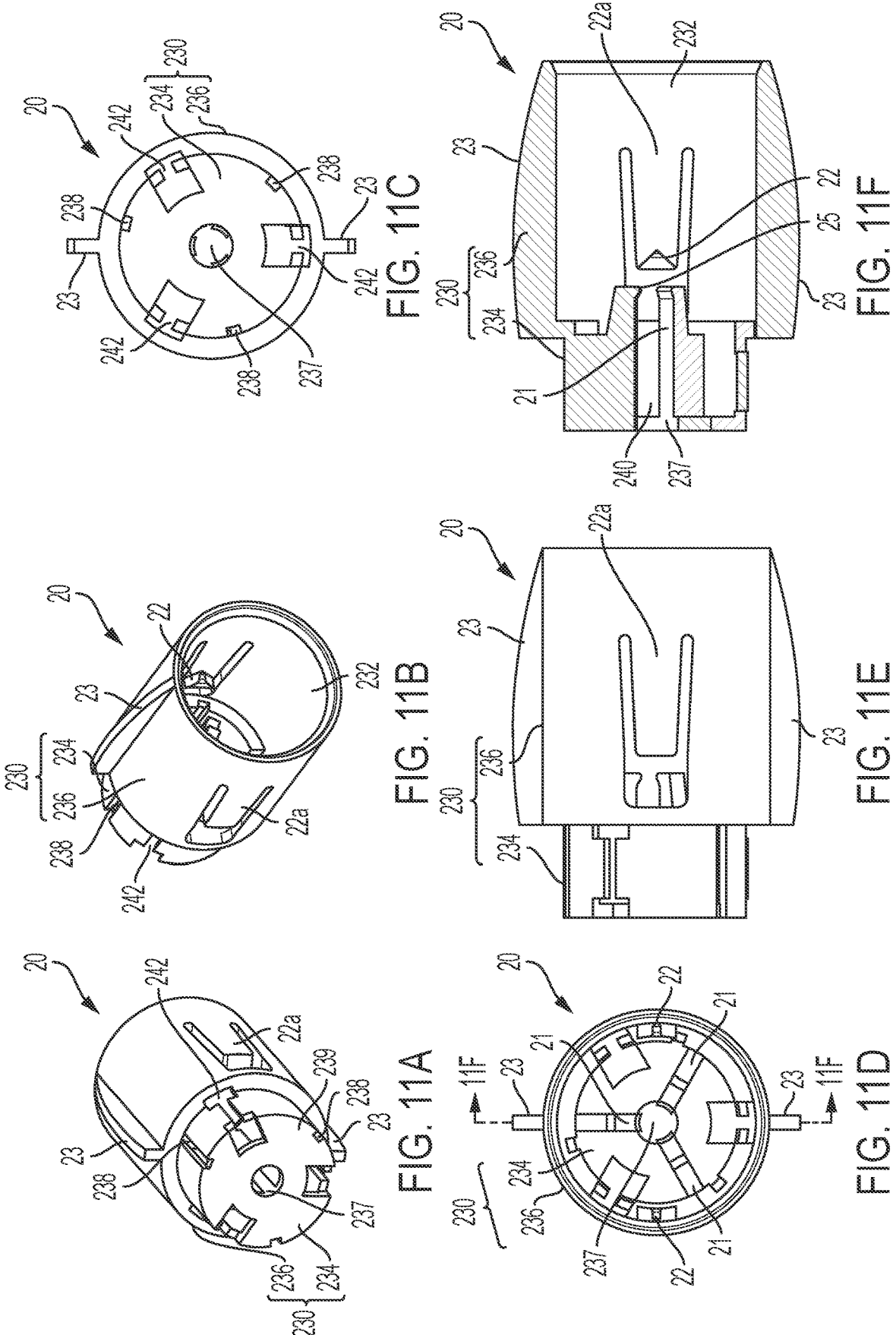
FIGS. 11A-11F depict views of a needle carrier according to one embodiment.
Figures 12A, 12B, 12C, 12D, 12E:
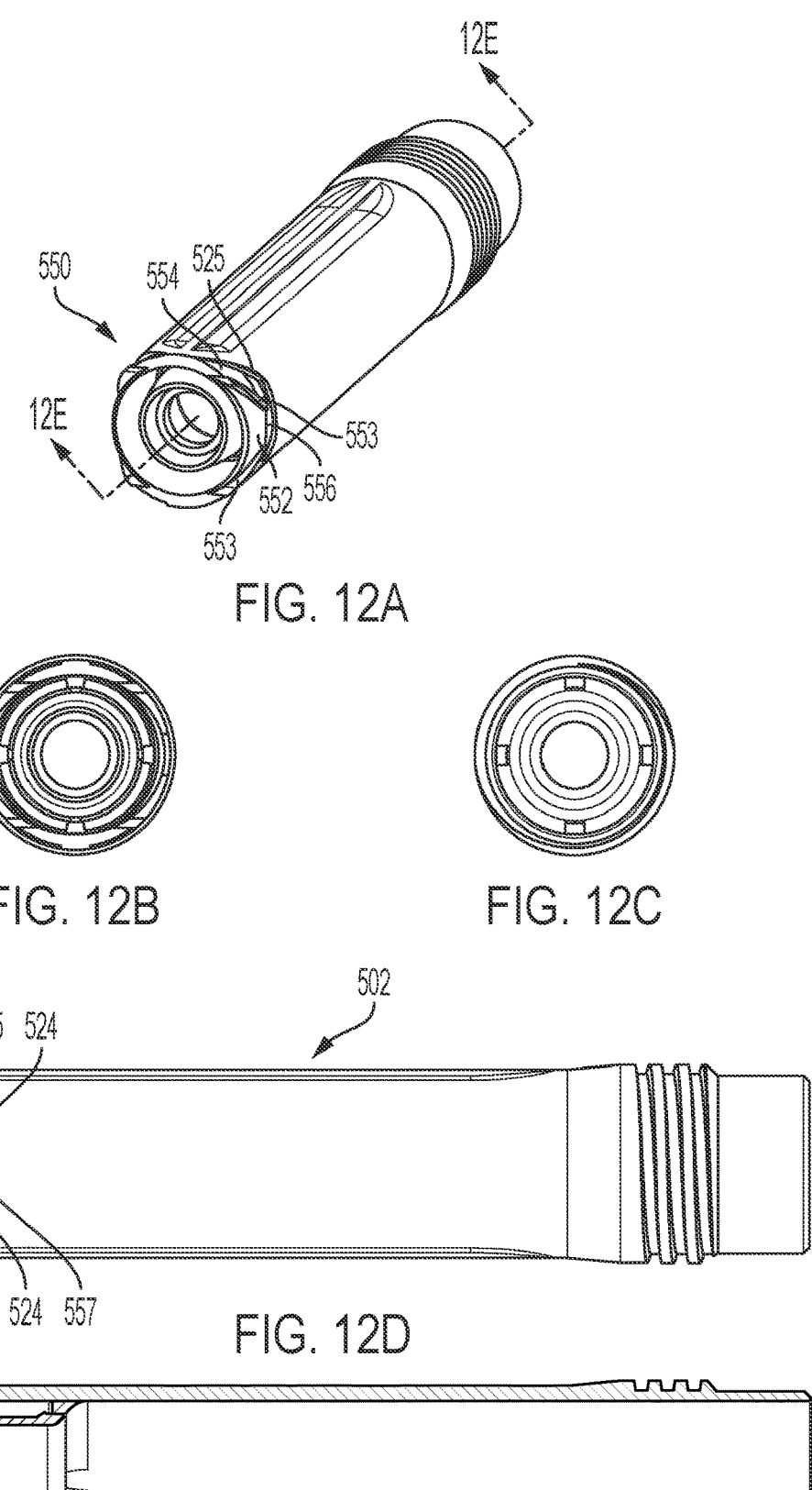
FIGS. 12A-12E depict views of a first portion of a drug device according to one embodiment.
Figure 13A:
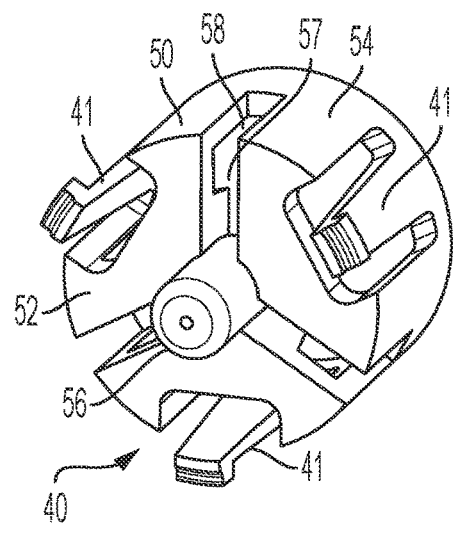
FIGS. 13A-13E depict views of a needle hub according to one embodiment.
Figure 13B:
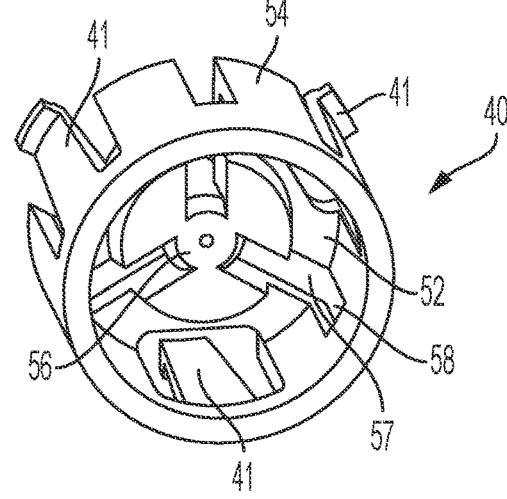
Figure 13C:
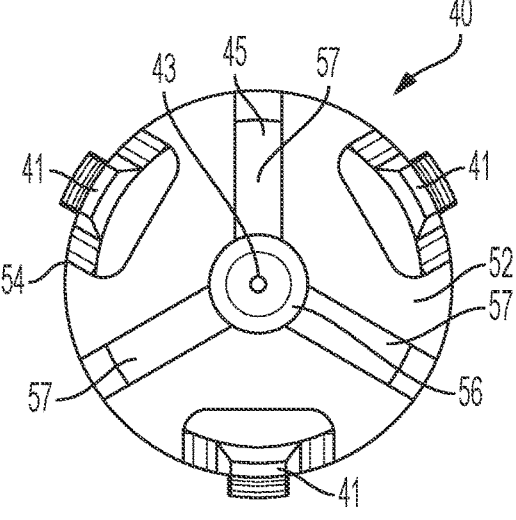
Figure 13D:
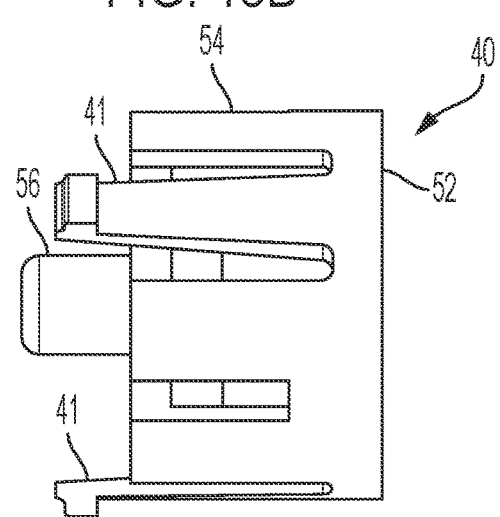
Figure 13E:
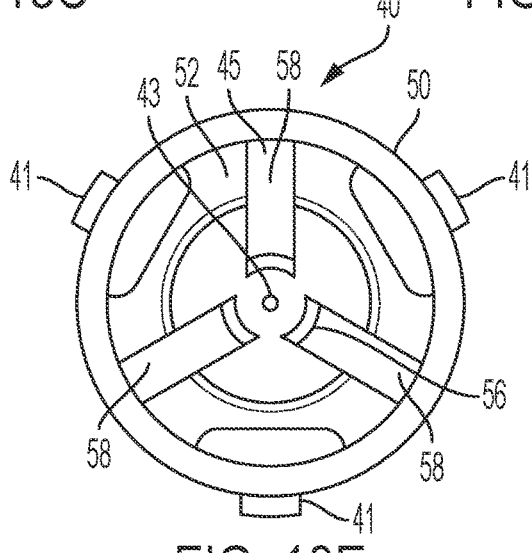
Figures 15A, 15B, 15C, 15D, 15E, 15F:
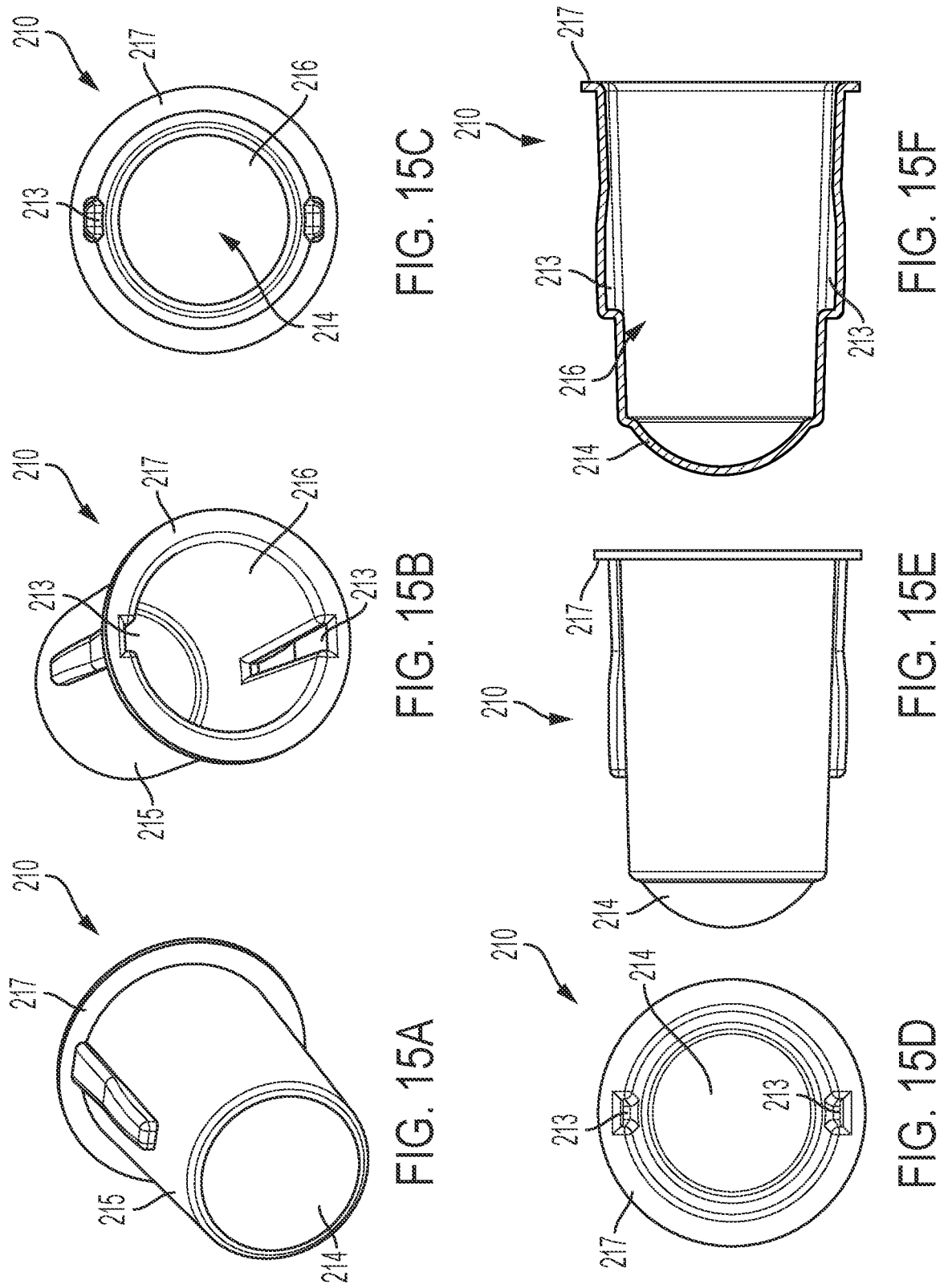
FIGS. 15A-15F depict views of a container according to one embodiment.

Finally, FIG. 10F shows the container body 210 being used to remove the needle assembly 100 from the drug device. The container body 210 may serve as sharps protection to help prevent the needle from being inadvertently contacted.

FIGS. 11A-11F depict various views of the needle carrier 20 according to one illustrative embodiment. The fins 23 that are received by the recesses of the container body can be seen in the perspective views of FIGS. 11A and 11B, as well as in the end views of FIGS. 11C and 11D, and the side view of FIG. 11E. The guide ribs 21 can be seen in the cross-sectional view of FIG. 11F, and the pawls 22 can be seen in FIGS. 11B, 11D, and 11F. As shown in this embodiment, the needle carrier 20 includes a generally cup-shaped cylindrical carrier body 230 defining a cavity 232 therein. The carrier body 230 includes a head portion 234 with a reduced cross-sectional area relative to the body portion 236. The fins 23 are shown extending axially along and radially outward from the body portion 236. The pawls 22 are formed at the end of pawl arms 22a along the body portion 236. The head portion 234 is configured to receive the trigger 30 (not shown) which is shaped to fit over the head portion 234. The head portion 234 includes axial slots to receive guide ribs. A first of the axial slots 242 are configured to receive support ribs 244. A second of the axial slots 238 are configured to receive the trigger guide ribs 35. Head portion defines a longitudinal bore 240 extending therein. The guide ribs 21 may be defined as a continuous surface that defines the bore such the proximal end of the guide ribs 21, with the radial tips 25 protruding within cavity 232 of the body portion. Bore 237 is formed in the end wall 239 of the head portion 234.

FIGS. 12A-12E depict various views of the first portion 502 of the drug device according to one illustrative embodiment. The coupling end 550 can be seen in the perspective view of FIG. 12A and the side view of FIG. 12D. The coupling end 550 includes an on-ramp 552 bounded by protruding sides 553, and off-ramps 554 that each have helical sides 525. The coupling end 550 also includes a snap edge 556 and a recess 557, as well as removal bumps 524.

FIGS. 13A-13E depict various views of the needle hub 40 according to one illustrative embodiment. The needle hub 40 includes a plurality of legs 41 that are able to move in the radially inward and outward direction. The hub also includes slots 45 configured to receive the guide ribs 21 from the carrier 20. The hub 40 also includes a bore 43 through which a needle is positioned. The needle may be fixed to the hub in any suitable manner, for example via an adhesive, insert molding, mechanical interlock, welding, being integrally formed with the needle, UV light activated glue, or any other suitable arrangement. Hub 40 may have a generally cup-shaped body 50 having an axial end wall 52 and a cylindrical sidewall 54 extend from the end wall. Legs 41 are formed along the sidewall. In one embodiment, there are three legs circumferentially spaced apart. Legs 41 may be integrally formed in to the sidewall 54 and cantilevered attached thereto such that the leg 41 can flex. A center axial body 56 is shown extending distally from the end wall 52 and includes the bore 43. Slots 45 are shown having a first portion 57 formed in the end wall 52 and extending radially outward from the center body 56 and a second portion 58 extending axially along the sidewall 54.

FIGS. 14A-14F depict various views of the trigger 30 according to one illustrative embodiment. The trigger includes ribs 35 having a contact surface 36 for pushing the needle hub legs radially inward to release the needle hub for needle extension, as described above. As also described above, a recess 33 distal to the ribs receives the needle hub leg after needle extension to lock the needle hub in place to prevent subsequent needle deployments. Trigger 30 includes a cup-shaped body 60 with an axial end wall 62 and cylindrical sidewall 64 shaped to define a trigger cavity 66 to receive the head portion 234 of the carrier body 230. Ribs 35 are axially disposed along the inner surface of the sidewall and circumferentially spaced apart from one another. Support ribs 244 are axially interdisposed between the ribs 35 along the inner surface and circumferentially spaced apart from one another. Bore 31 is formed in the end wall 62.

FIGS. 15A-15F depict various views of the container body 210 according to one illustrative embodiment. The container body includes recesses 213 that receive the fins 23 of the needle carrier to couple the container body to the needle assembly. The body 210 is generally cup-shaped with an axial end wall 214 and a sidewall 215 extending from the end wall 214 to define a container cavity 216 sized and shaped to receive the carrier 20. A radial flange 217 may extend from the proximal end of the sidewall 215 and sized to provide more contact surface for the cover seal. Recesses 213 are defined along the inner surface of the sidewall. The end wall 214 may be generally hemispherical. According to one aspect, a drug delivery device may be configured such that the needle of the device remains hidden from a subject throughout all operational steps of the device. For example, the needle may remain hidden during attachment of a needle assembly to a drug device and during removal of the needle assembly from the drug device. The drug delivery device may include a deployment mechanism that moves the needle from a retracted position to an extended position to pierce a subject and permit delivery of medicament to the subject, and a retraction mechanism that retracts the needle after injection of the medicament.

Figures 16A, 16B, 16C, 16D, 16E, 16F, 16G, 16H:
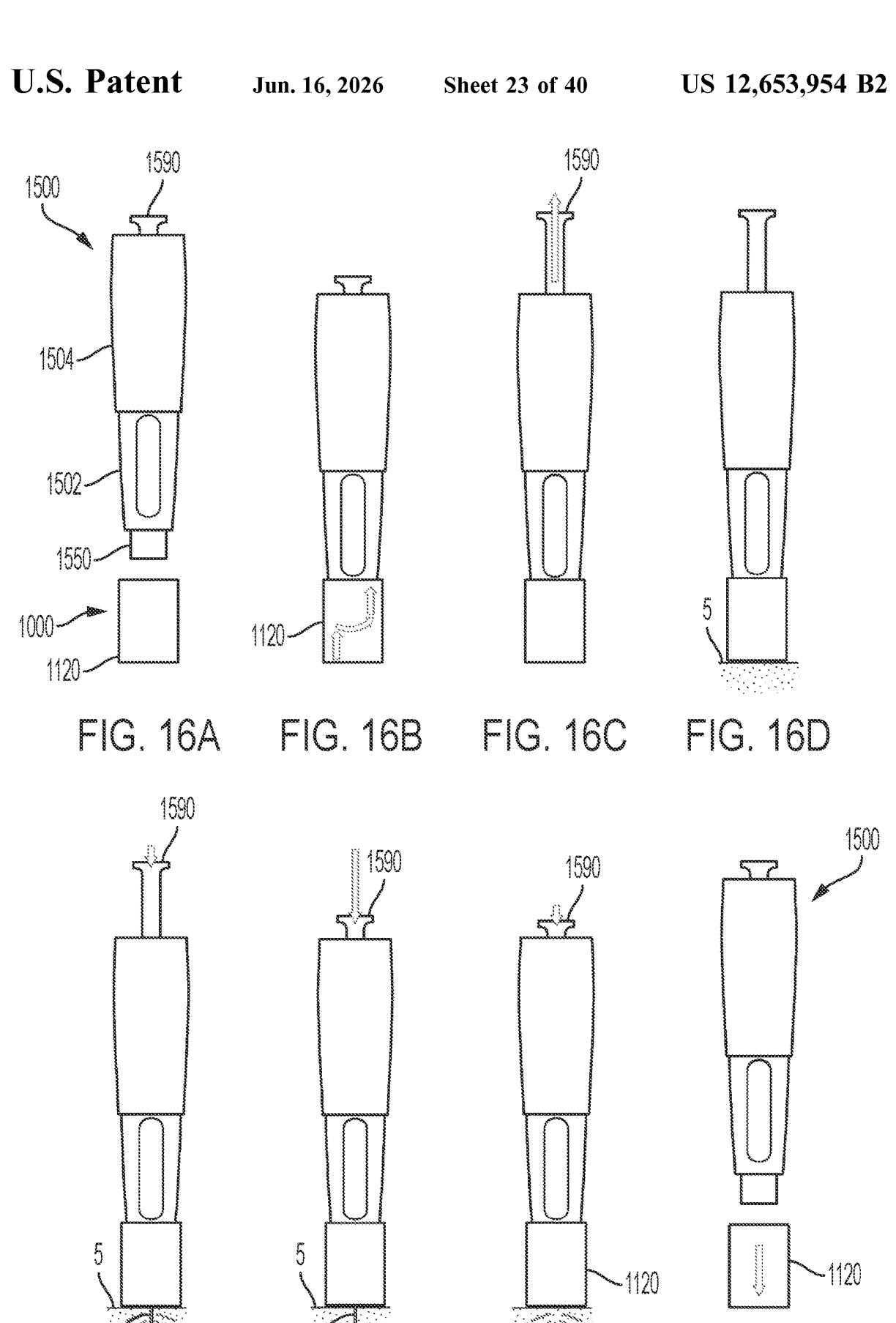
FIGS. 16A-16H depict a series of schematics of a drug delivery device according to one embodiment undergoing a sequence of steps in which a needle assembly is attached to a drug device, a needle is moved in an extension direction to pierce a subject's skin, the needle is moved in a retraction direction, and the needle assembly is removed from the drug device.

FIGS. 16A-16H depict a series of schematics of a drug delivery device according to one embodiment undergoing a sequence of operational steps. As shown in FIG. 16A, a drug delivery device may include a needle assembly 1000 and a drug device 1500. The drug device may include a first portion 1502 that houses a medicament container, and a second portion 1504 that includes an actuator 1590 and an actuation arrangement that serves to expel medicament from the medicament container for injection into a subject.

The first portion 1502 of the drug device may include a coupling end 1550 for coupling to the needle assembly 1000. FIG. 16B illustrates a process of coupling a needle carrier 1120 of the needle assembly 1000 to the drug device. As will be discussed in greater detail below, in some embodiments, to couple the carrier to the drug device, a user pushes the carrier onto the drug device, turns the carrier relative to drug device, and then again pushes the carrier further onto the drug device.

Next, as shown in FIG. 16C, the drug delivery device is set for injection by pulling back on the actuator 1590. It should be appreciated that many different types of actuation mechanisms may be integrated into the drug delivery device, and what is shown in the provided illustrative embodiments are not intended to limit the drug delivery device.

Next, as shown in FIG. 16D, the drug delivery device is placed flush with the subject's skin, with the needle carrier 1120 in contact with the skin 5.

The drug delivery device is now ready to be actuated to inject medicament into the subject. In some embodiments, actuation of the device actuator 1590, e.g. by pushing the actuator in a distal direction, may cause multiple actions to occur. First, as shown in FIG. 16E, pressing down on the actuator 1590 may cause a needle 1010 to extend from the needle carrier 1120 and pierce into the skin 5. Next, the device may permit medicament to be expelled from the medicament container, out through the needle, and into the subject. Finally, as shown in FIG. 16G, the device may retract the needle back into the needle carrier 1120. As a result, with the needle retracted inside the needle carrier, when the drug delivery device is removed from the subject's skin, the needle is no longer external to the device, helping to prevent inadvertent contact with the needle, and allowing a subject to avoid seeing the needle.

Finally, as shown in FIG. 16H, the needle assembly may be removed from the drug device 1500 by pulling the needle carrier 1120 off of the drug device in a distal direction.

Figure 17:
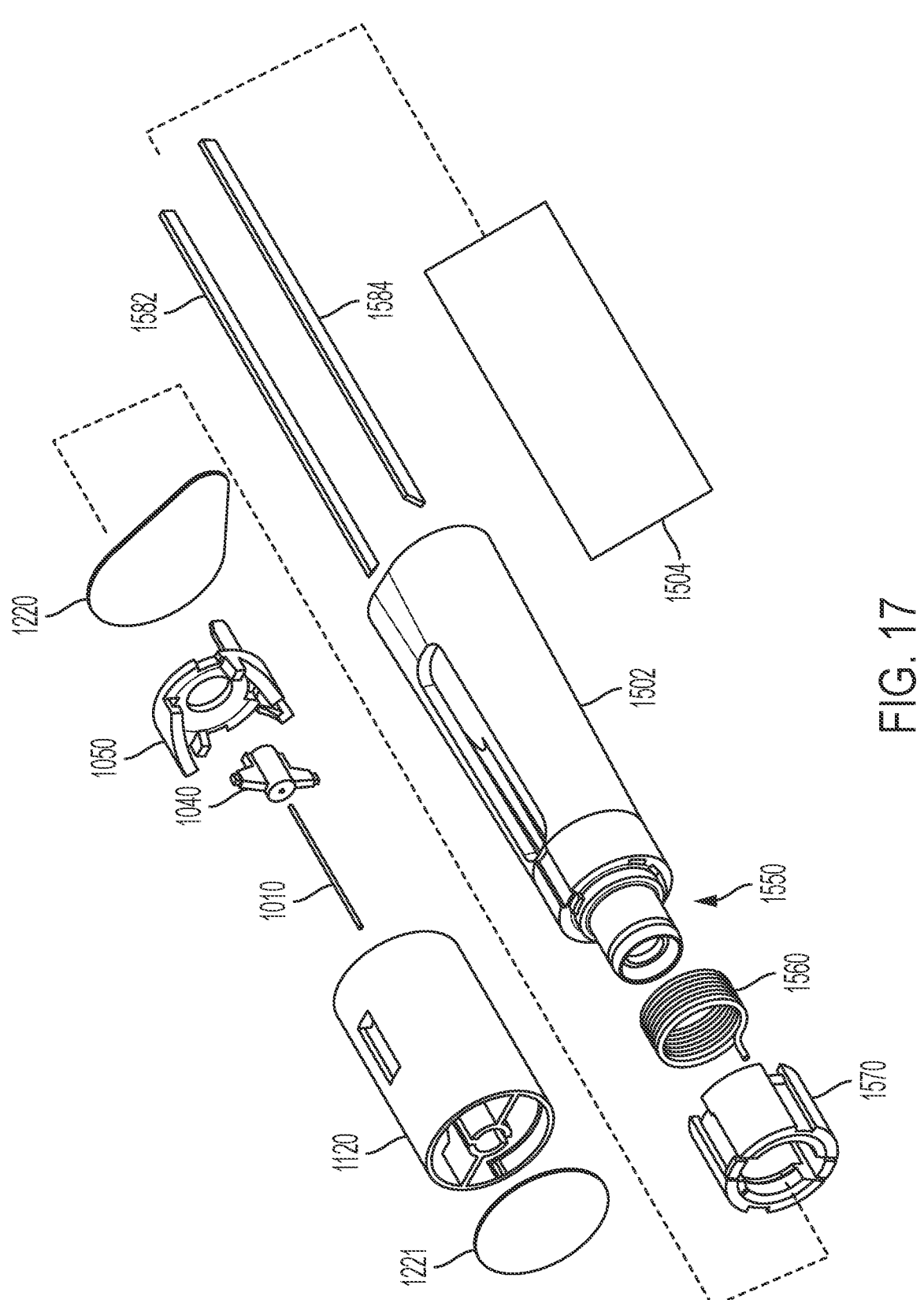
FIG. 17 is an exploded view of a drug delivery device according to one embodiment.

An exploded view of an illustrative embodiment of a drug delivery device is shown in FIG. 17. The drug delivery device includes a needle assembly, including a needle 1010, a carrier 1120, a needle hub 1040, and a cam 1050. In some embodiments, the carrier 1120 may initially house the other components of the needle assembly. In some embodiments, a proximal cover 1220 may be positioned on a proximal end of the carrier 1120, and a distal cover 1221 may be positioned on a distal end of the carrier 1120. In some embodiments, the proximal cover 1220 is removable from the needle carrier 1120 in order to expose the components within the carrier and to permit coupling of the needle carrier to a drug device. In some embodiments, the proximal cover is a peelable seal. In some embodiments, the distal cover 1221 is not configured to be removed, but instead is configured to be pierced through by a needle. In other embodiments, however, the distal cover 1221 is configured to be removed.

The drug device side may include a first portion 1502 and a second portion 1504. The first portion 1502 may house a medicament container. In some embodiments, the second portion 1504 may include a device actuator, and may include an actuation mechanism that serves to trigger release of medicament from a medicament container. As shown in FIG. 17, the drug device also includes a collar 1570, a drive spring 1560, a retraction trigger 1582, and an extension trigger 1584. In some embodiments, the drive spring 1560 is a torsion spring.

As will be discussed in detail, in some embodiments, the needle assembly couples to the drug device via the carrier 1120 physically interlocking with a coupling end 1550 of the drug device.

Figure 18A:
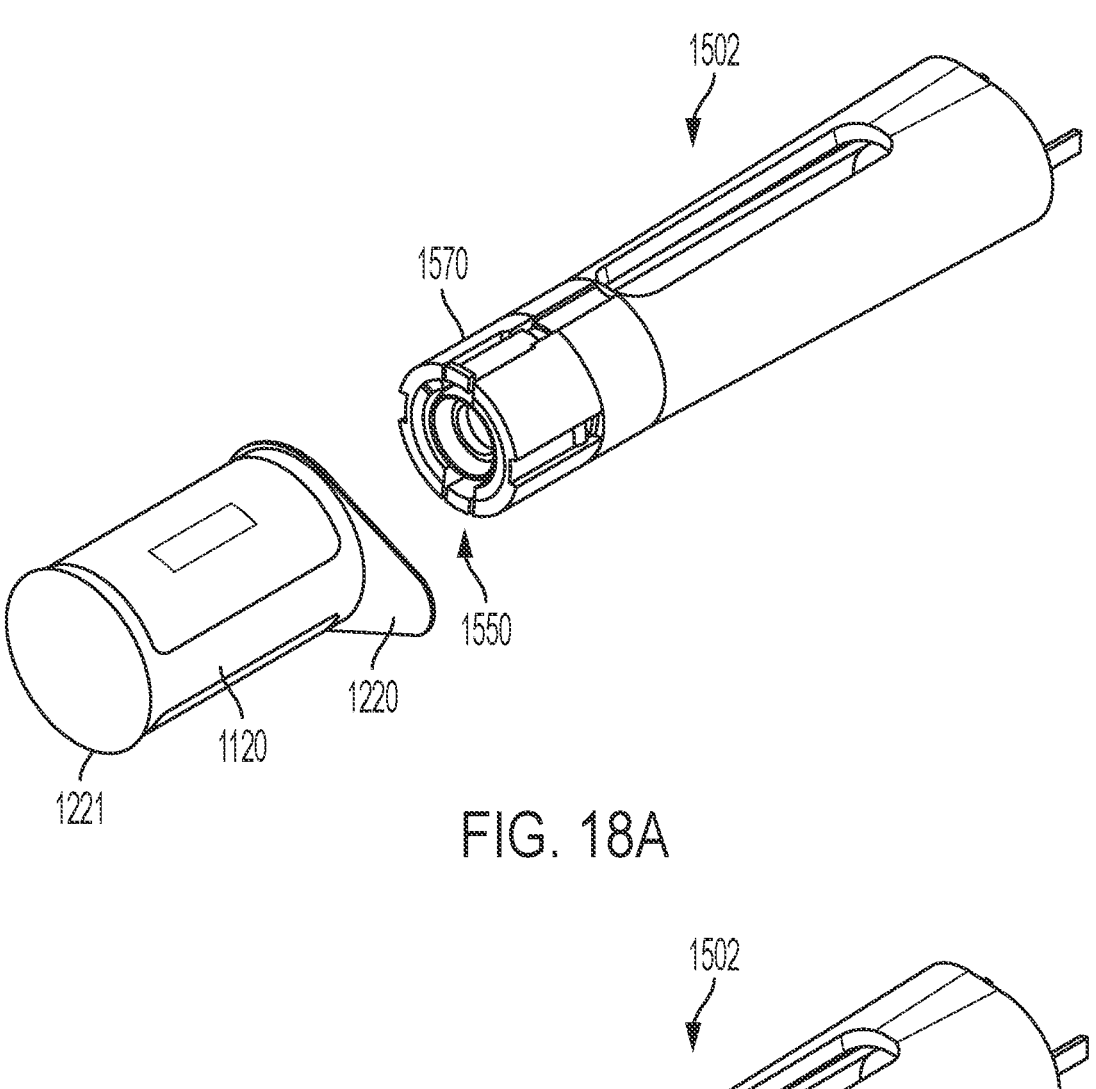
FIG. 18A is a perspective view of a needle assembly and drug device being prepared for use with the drug device.
Figure 18B:
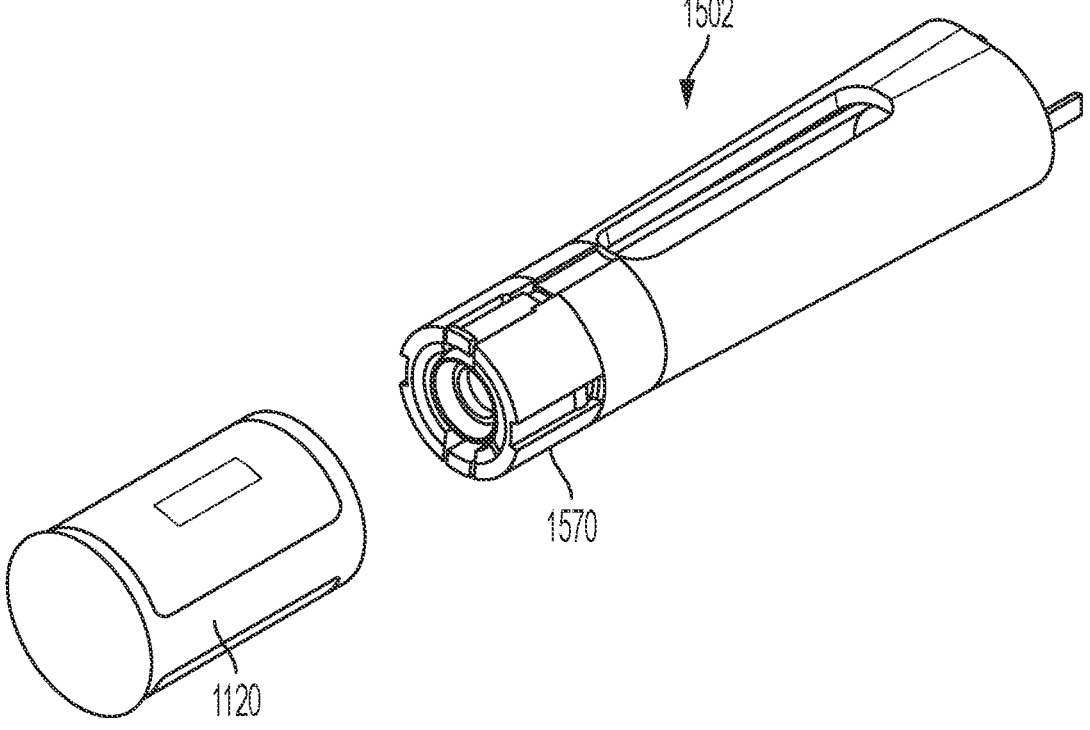
FIG. 18B is a perspective view of the needle assembly and drug device of FIG. 18A, with a peel tab removed.

FIGS. 18A-18G depict the drug delivery device of FIG. 17 undergoing a sequence of steps including coupling of a needle assembly to a drug device, extension of a needle, and retraction of the needle. Starting with FIG. 18A, components of a needle assembly are initially held within the needle carrier 1120, which is sealed via a proximal cover 1220 and a distal cover 1221. Next, as shown in FIG. 18B, the proximal cover 1220 is removed from the carrier 1120, exposing the other components of the needle assembly and preparing the carrier 1120 to be coupled to a coupling end 1550 of a first portion 1502 of a drug device. In the illustrative embodiment of FIGS. 18A-18G, the first portion 502 of the drug device includes a collar 1570 at the coupling end 1550 of the drug device.

In some embodiments, the collar 1570 is rotatable between a deactivated orientation in which the needle carrier cannot be coupled to the collar, and an activated orientation in which the needle carrier can be coupled to the collar. FIG. 18B shows the collar in the deactivated state. In this state, the needle carrier 1120 is physically blocked from sliding onto the collar.

Figure 18C:
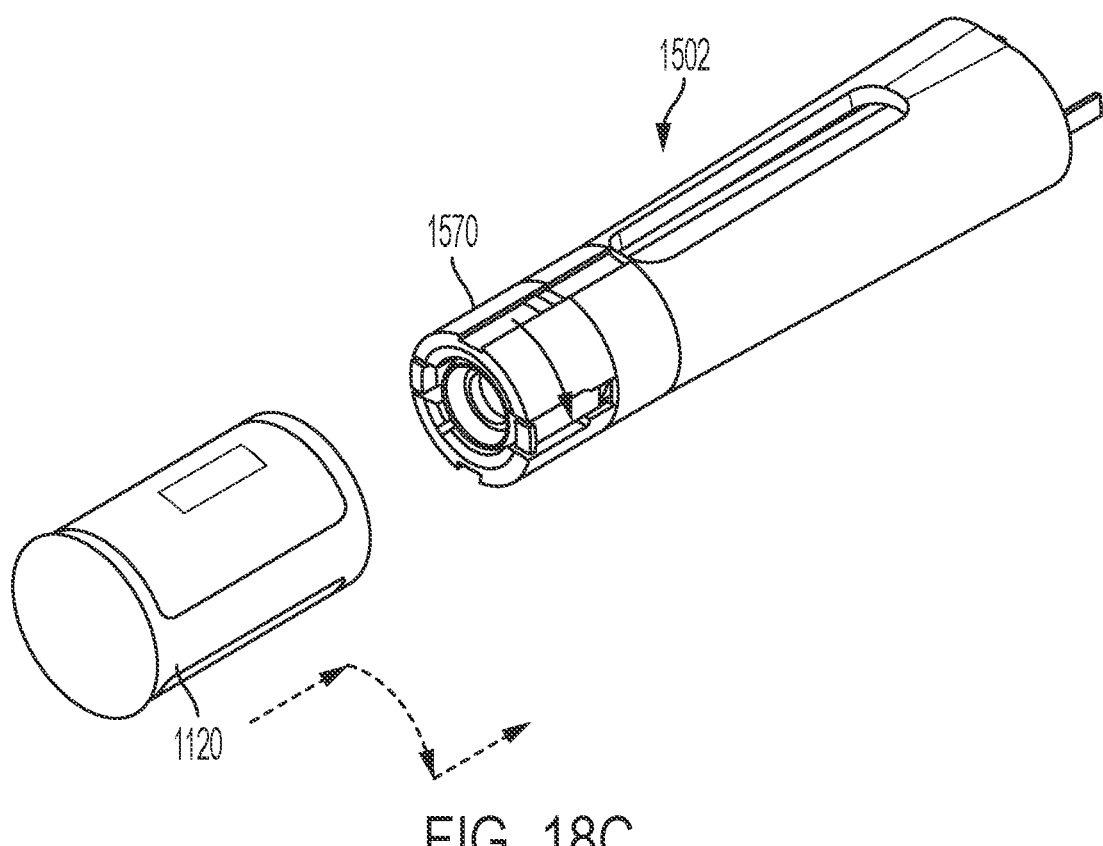
FIG. 18C is a perspective view of the needle assembly and drug device of FIG. 18B with a collar of the drug device being turned to receive the needle assembly.
Figure 18D:
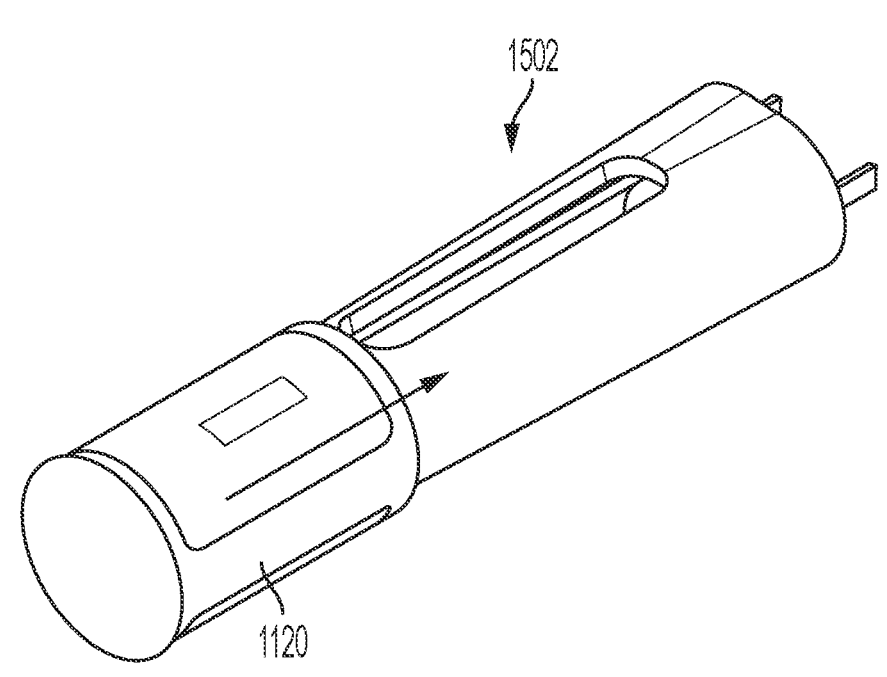
FIG. 18D is a perspective view of the needle assembly and drug device of FIG. 18C with the needle assembly being coupled to the drug device.
Figures 18E, 18F, 18G:
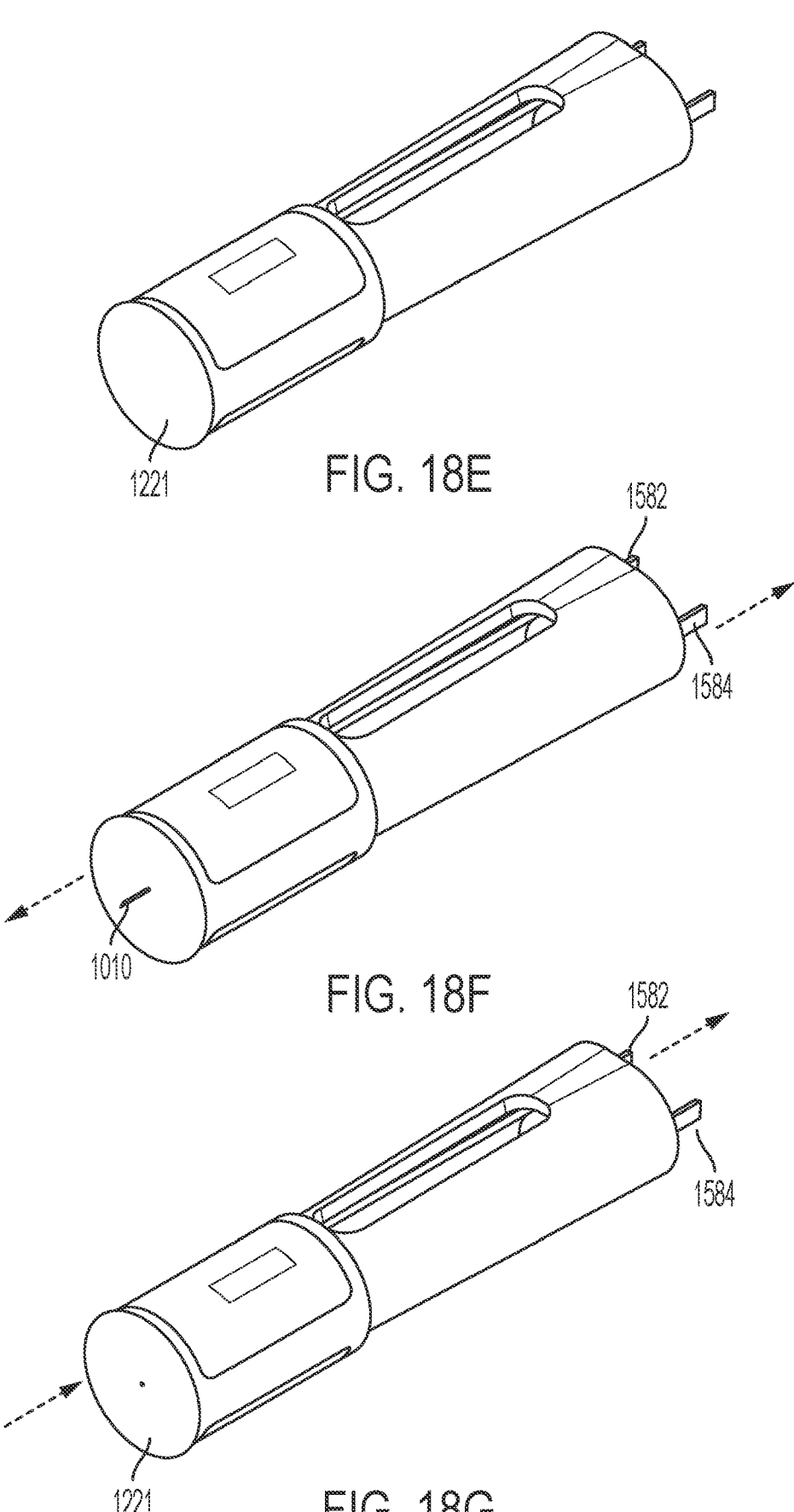
FIG. 18E is a perspective view of the needle assembly and drug device of FIG. 18D with the needle assembly coupled to the drug device.
FIG. 18F is a perspective view of the needle assembly and drug device of FIG. 18E with a needle of the needle assembly in an extended position.
FIG. 18G is a perspective view of the needle assembly and drug device of FIG. 18E with the needle in a retracted position.

In FIG. 18C, the collar 1570 has been rotated to an activated orientation. The needle carrier can now be slid onto the collar 1570. A user first pushes the carrier 1120 onto the collar, then rotates the carrier relative to the collar, and finally pushes the carrier further onto the collar, resulting in the needle assembly being coupled to the drug device as shown in FIGS. 18D and 18E. The needle carrier may be retained to the drug device via a detent, which will be discussed in further detail below.

Next, as shown in FIG. 18F, a user actuates the drug device and causes the extension trigger 1584 to activate, which causes needle 1010 to move from a retracted position to an extended position, piercing through distal cover 1221 in the process. It should be appreciated that in this embodiment, both the extension and retraction triggers are provided; however the present disclosure is not limited in this regard. Thus, in one embodiment, only the extension trigger is provided. In another embodiment, only the retraction trigger is provided.

Following this, a retraction trigger 1582 is activated, which causes the needle 1010 to move back to a retracted position within the carrier 1120.

Figure 19:
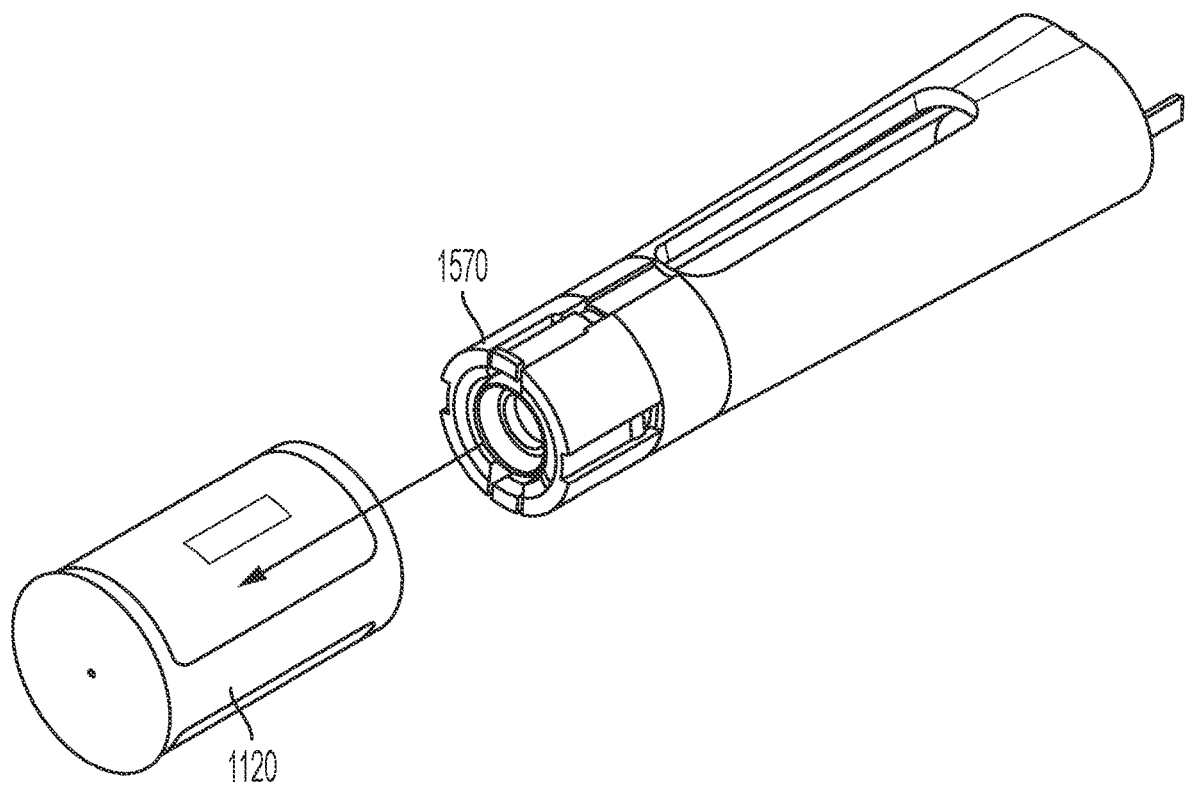
FIG. 19 is a perspective view of the needle assembly and drug device of FIG. 18G with the needle assembly removed from the drug device.

In some embodiments, a user may be able to remove the needle assembly from the drug device. As shown in FIG. 19, the needle carrier 1120 may be pulled straight off of the drug device to remove the needle assembly. In some embodiments, the needle assembly is configured to prevent re-attachment of the used needle assembly back to the drug device, as will be described in further detail below.

A series of cross-sectional views of the drug delivery device of FIG. 17 as the device undergoes a sequence of operational steps is provided at FIGS. 20A-20F.

Figures 20A, 20B:
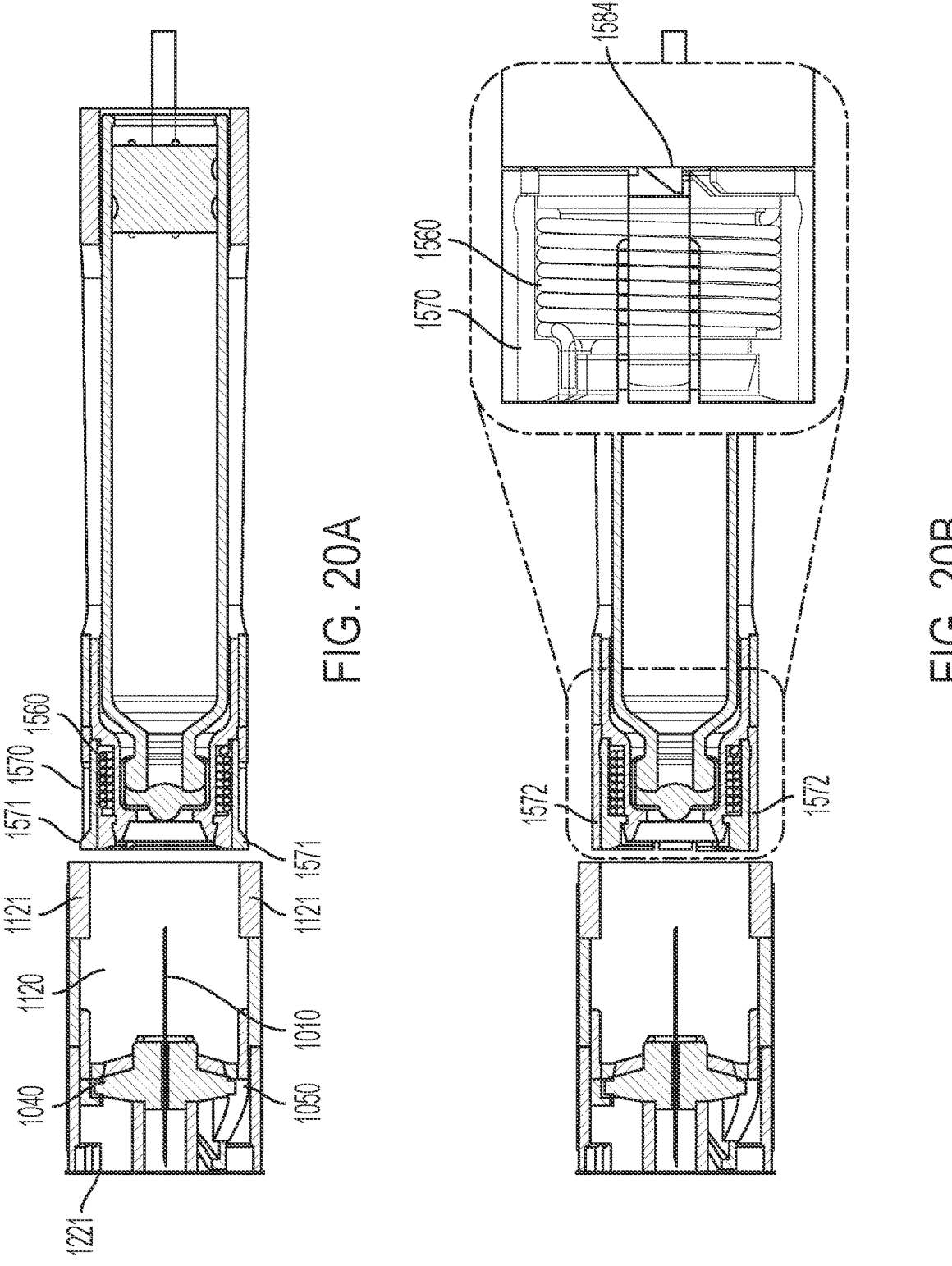
FIGS. 20A-20F depict cross-sectional views of a needle assembly being coupled to a drug device.

FIG. 20A shows the drug delivery device in a state in which the needle assembly is not yet coupled to the drug device. The needle assembly includes a needle carrier 1120, as well as a needle 1010, needle hub 1040 and cam 1050 housed within the needle carrier 1120. A distal cover 1221 is also located at a distal end of the needle carrier 1120. On the drug device side, the drug device includes a collar 1570 and a torsion spring 1560.

In FIG. 20A, the collar 1570 is shown in a deactivated state. In the deactivated state, the collar is in a rotational orientation relative to the needle carrier that prevents the needle carrier from sliding onto the collar. As seen in FIG. 20A, in the deactivated state, collar arms 1571 are aligned with tabs 1121 of the needle carrier. The presence of the collar arms 1571 physically interfere with the tabs 1121 of the needle carrier, thus preventing the needle carrier from being moved onto the collar.

As shown in FIG. 20B, the collar can be rotated to an activated state relative to the needle carrier. In the activated state, slots 1572 on the collar are now rotationally aligned with the carrier tabs 1121, thus giving the carrier clearance to be pushed onto the collar.

The spring 1560 is initially held in a wound state. In other words, prior to actuation of the drug delivery device, the spring 1560 has stored spring potential energy. With the collar in the position shown in FIG. 20B, the spring 1560 is held in its wound state by the presence of extension trigger 1584. As shown in the enlarged view of FIG. 20B, the extension trigger 1584 physically blocks the collar 1570 from rotating, which in turn prevents the spring 1560 from being able to unwind.

Figures 20C, 20D:
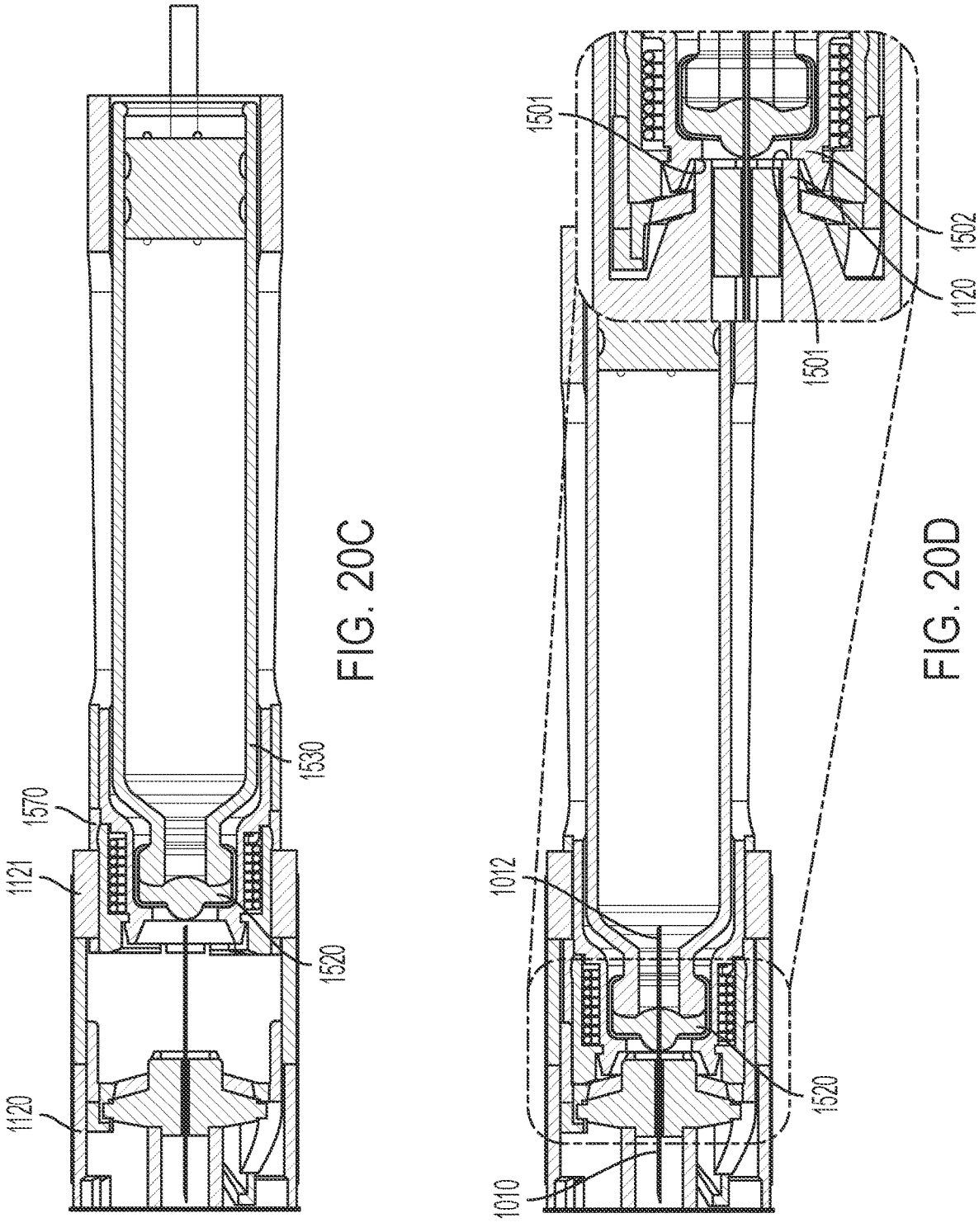

FIG. 20C shows the needle carrier 1120 pushed onto the collar 1570, with the carrier tabs 1121 received within the slots of the collar. At this initial engagement stage, the needle 1010 has not yet entered the septum 1520 of the medicament container 1530.

After this initial engagement with the drug device, the needle carrier is turned relative to the drug device and then further pushed onto the drug device, resulting in full engagement of the needle carrier with the drug device, shown in FIG. 20D. At the full engagement stage, the proximal end 1012 of the needle 1010 has penetrated through the septum 1520 and entered the interior of the medicament container 1530. As shown in the enlarged view of FIG. 20D, at full engagement, the carrier 1120 and the first portion 1502 of the drug device are in an area of contact 1501. As the user pushes the needle carrier against an injection site, axial forces between the needle carrier and the drug device are transferred in the area of contact 1501. Detailed views of the carrier are shown in FIGS. 28A-28F and detailed views of the collar are shown in FIGS. 31A-31E.

Next, in preparation for injection of medicament into a subject, the drug delivery device is held against the skin 5 of the subject, with the distal cover 1221 at the end of the needle carrier being held in contact against the skin.

The user actuates the drug delivery device to pull back on the extension trigger 1584, moving the trigger in the proximal direction, which frees the collar 1570 to rotate due to unwinding of the torsion spring 1560. Rotation of the collar rotates the cam 1050, which, because the radial ends 1052 of the arms 1041 ride on the cam surfaces 1051, causes the needle hub 1040 to extend the needle 1010, moving the needle from a retracted position to an extended position in which the distal end 1014 of the needle 1010 penetrates through the distal cover 1221 and into the subject's skin 5, as shown in FIG. 20E.

Figure 20E:
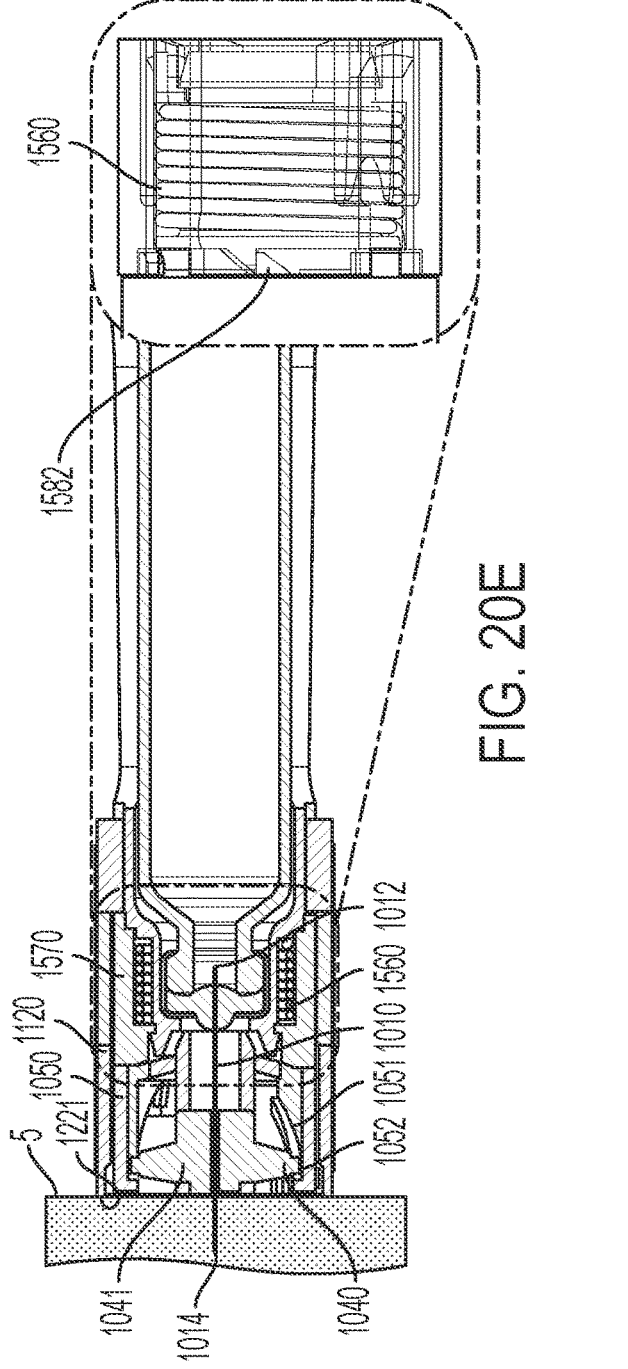
Figure 20F:
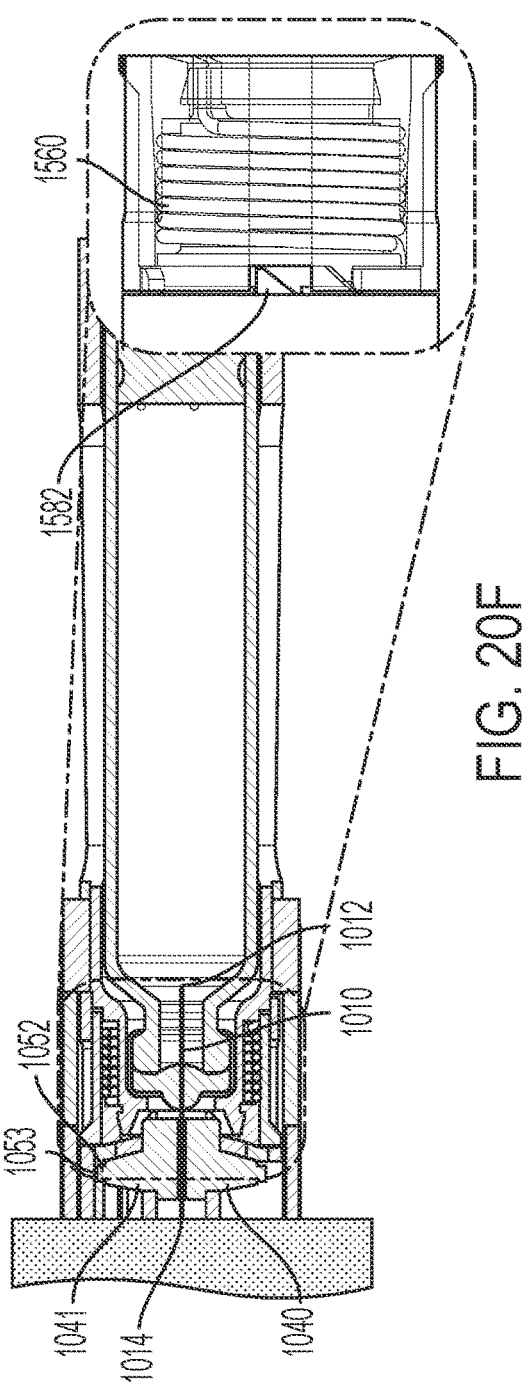

At the needle extension stage shown in FIG. 20E, the torsion spring 1560 is still partially wound. The spring 1560 is prevented from further unwinding due to the presence of the retraction trigger 1582. As shown in the enlarged view of FIG. 20E, the retraction trigger 1582 physically blocks rotation of the collar 1570, which in turn prohibits further unwinding of the spring.

Next, the retraction trigger 1582 is released, pulling the retraction trigger in a proximal direction away from the collar 1570, freeing the collar to rotate due to unwinding of the spring 1560. This further rotation of the collar drives the cam 1050 and needle hub 1040 to retract the needle. Releasing the retraction trigger may be accomplished by any suitable arrangement. For example, pulling the device away from the user's skin could cause the retraction trigger to release. Completing the injection along with needle withdrawal and a short time delay could cause the retraction trigger to release. In one embodiment, the retraction trigger is actuated automatically after completion of injection. For a complete dose, and to avoid excessive "drooling" after the needle is withdrawn, a suitable delay after the injection is completed may be desired. Such a delay could be ~5 seconds before needle is retracted. Such a delay may be automatic or may be an instruction to the user to hold the device against the skin and then the release trigger is moved when the device is removed from the user's skin.

Figure 21A:
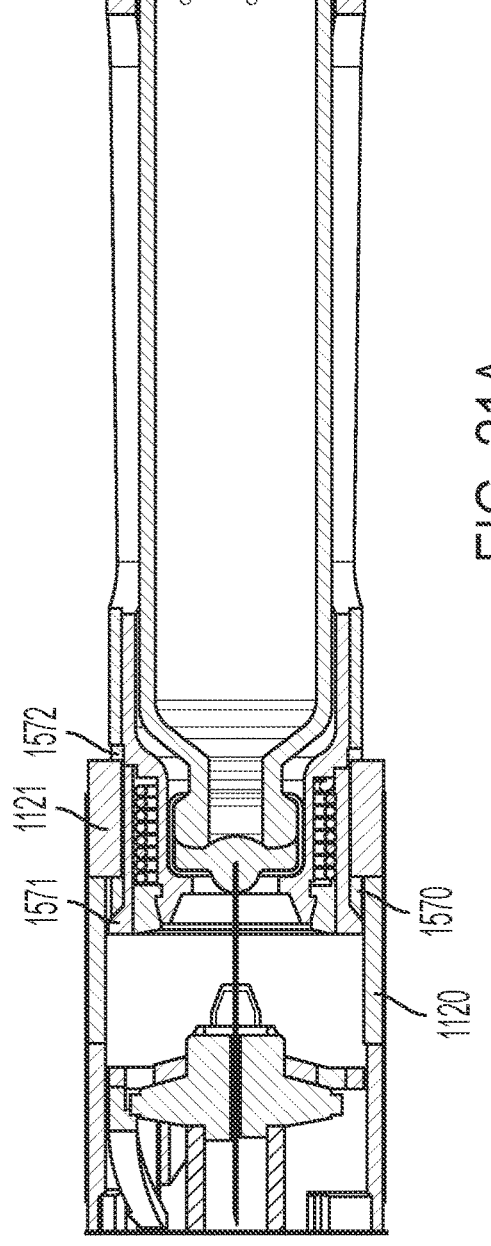
FIGS. 21A-21B depict cross-sectional views of the needle assembly of FIG. 20A being removed from the drug device.
Figure 21B:
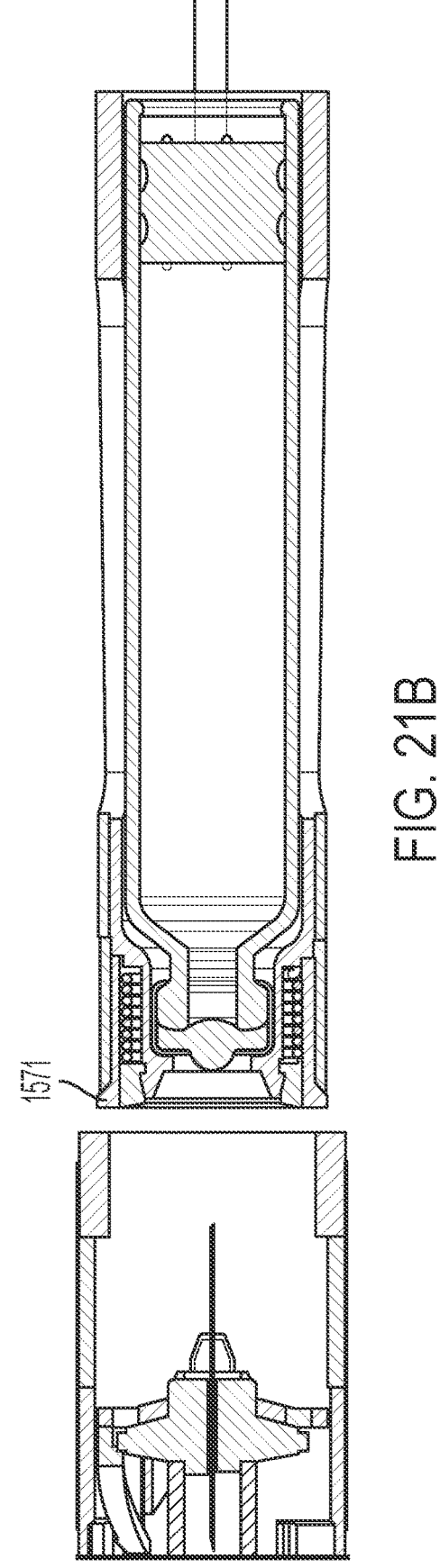

In some embodiments, the needle assembly may be removed from the drug device after injection of medicament. As shown in FIGS. 21A and 21B, the needle carrier 1120 is removed from the collar 1570 by pulling the carrier off of the collar in a distal direction. The tabs 1121 of the carrier slide out of the slots 1572 of the collar, and the arms 1571 flex radially inwardly to permit removal of the carrier from the collar. The carrier is shown fully removed from the drug device in FIG. 21B. Here, the needle carrier 1120 is a multi-function component in that the carrier may be used to mount the needle assembly to the device, may remain with the needle assembly for operation of the device, may be used as a tool to remove the needle assembly from the device, and contains the used needle assembly after use.

FIGS. 22A-25B depict the rotational positions of the collar relative to the drug device of the embodiment of FIG. 17 as the drug delivery device undergoes a sequence of operational steps. For ease of visualizing components, the collar is shown in phantom.

Figures 22A, 22B, 23A, 23B, 24A, 24B, 25A, 25B:
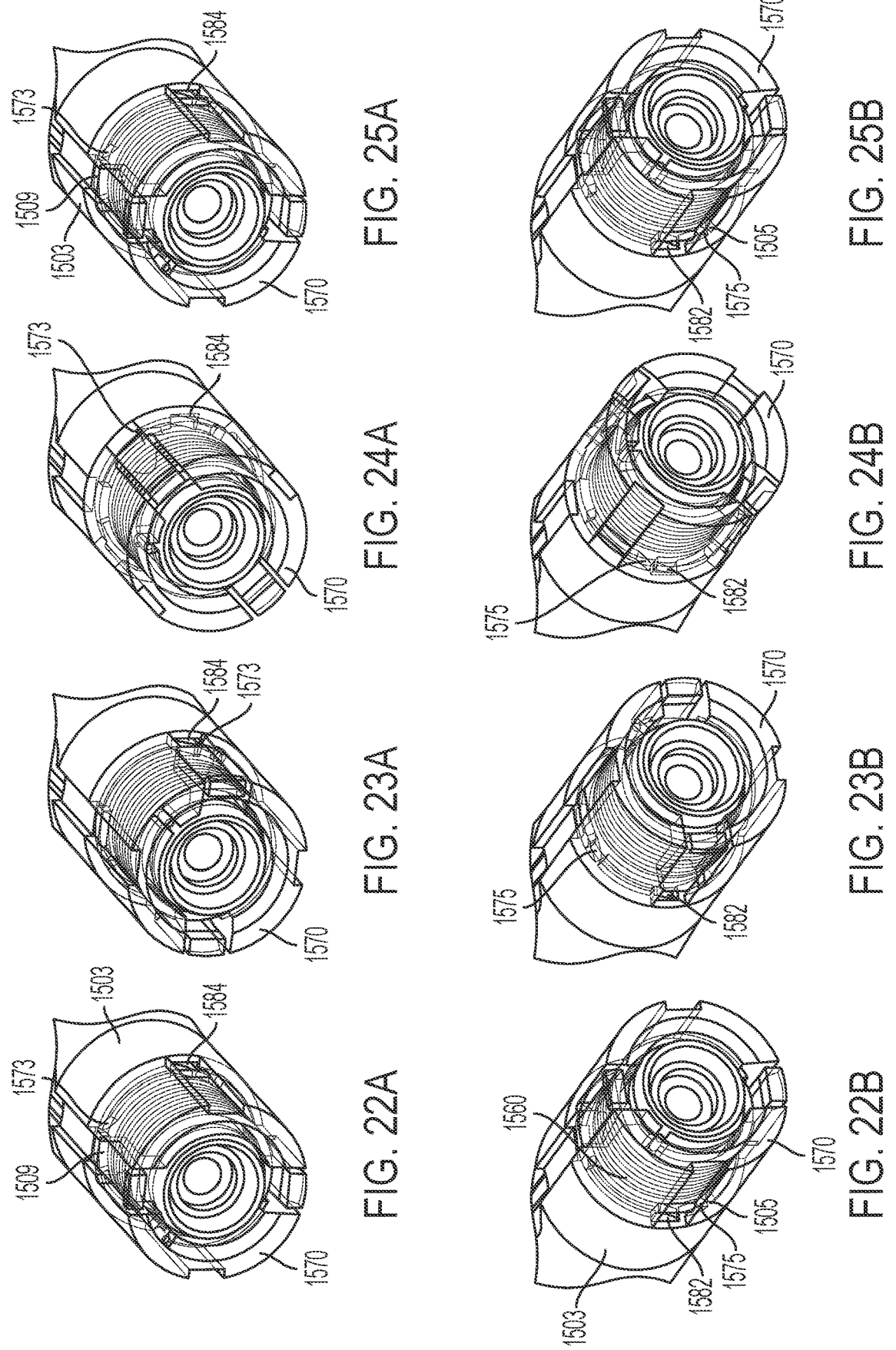
FIGS. 22A and 22B show two perspective views of the collar prior to use in the deactivated state.
FIGS. 23A and 23B show two perspective views of the collar after the collar has been rotated to the activated state.
FIGS. 24A and 24B show two perspective views of the collar after the needle has moved to the extended position.
FIGS. 25A and 25B show two perspective views of the collar after the needle has moved to the retracted position.

First, FIGS. 22A and 22B show two perspective views of the collar prior to use, when the collar is in the deactivated state. The collar is rotationally mounted to a housing 1503 of the first portion of the drug device. The collar includes first and second collar stops 1573 and 1575 that are initially in contact against the housing 1503. As seen in FIG. 22A, the first collar stop 1573 is initially in contact with first housing stop 1509. As seen in FIG. 22B, the second collar stop 1575 is initially in contact with second housing stop 1505. Detailed views of the collar are shown in FIGS. 31A-31E, and detailed views of the housing are shown in FIGS. 32A-32D.

FIGS. 23A and 23B show two perspective views of the collar after it has been rotated and placed in the activated state. In this state, the first collar stop 1573 is in contact with the extension trigger 1584, and the second collar stop 1575 is in the air. Contact between the first collar stop 1573 and the extension trigger 1584 prevents the collar from further rotating and prevents the spring 1560 from unwinding.

Next, when the extension trigger 1584 is released and pulled back in a proximal direction, the collar is permitted to rotate due to unwinding of the spring 1560 until the second collar stop 1575 contacts the retraction trigger 1582, as shown in FIG. 24B. The first collar stop 1573 is in the air, as shown in FIG. 24A.

Next, when the retraction trigger 1582 is released and pulled back in a proximal direction, the collar is permitted to further rotate due to unwinding of the spring 1560 until the first and second collar stops contact the housing 1503 of the first portion of the drug device, as shown in FIGS. 25A and 25B.

Figure 26A:
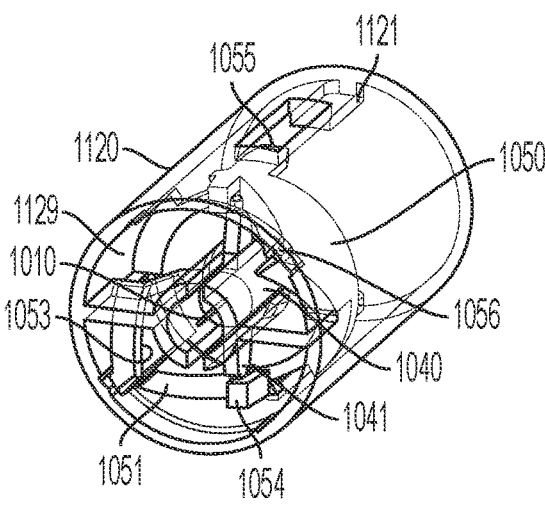
FIGS. 26A-26C depict the arrangements of a cam of the needle assembly as the drug delivery device undergoes a sequence of needle extension steps.
Figure 26B:
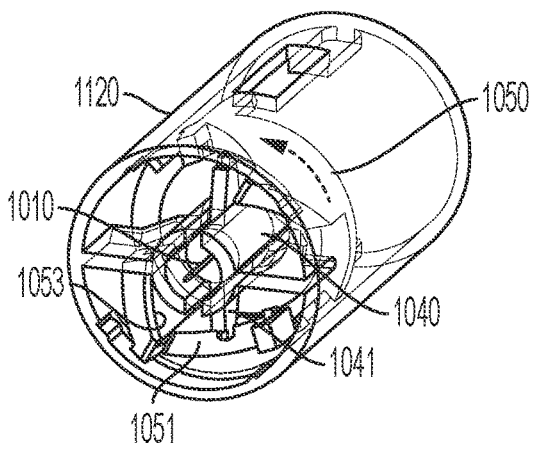
Figure 26C:
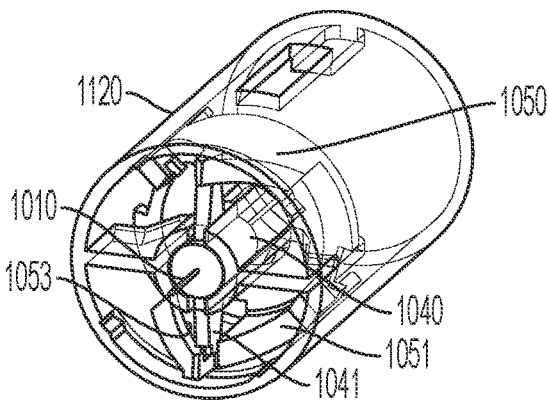

FIGS. 26A-26C depict the arrangements of the cam and needle hub of the needle assembly as the drug delivery device undergoes a sequence of needle extension steps. For ease of visualizing components, the carrier is shown in phantom. FIG. 26A shows the cam 1050 in the initial angular position prior to use of the drug delivery device. The cam may include tabs 1055 that are initially aligned with the carrier tabs 1121 to permit coupling of the carrier 1120 with the collar of the drug device. The cam may include detents 1056 that are received by an inner wall surface 1129 of the carrier 1120 to help maintain the position of the cam within the carrier prior to use. The cam may include teeth 1054 that abut against arms 1041 of the needle hub 1040 to retain the hub in place during piercing of the septum with the proximal end of the needle. The cam may include extension cam surfaces 1051 (also referred to as extension helices 1051) on which rides the radial ends 1052 of the arms 1041. The cam may also include retraction cam surfaces (also referred to as retraction helices 1053) defined by radially inwardly extending lips 1053a that also interacts with a radial end 1052 of an arm 1041 during rotation of the cam. Specifically, a first surface 1057 (see FIG. 30A) of the radial end 1052 rides along the extension cam surface 1051 when the cam is being rotated in one direction and a second surface 1059 (see FIG. 30A) of the radial end 1052 rides along the retraction cam surface 1053 when the cam is being rotated in the opposite direction. Detailed views of the hub are shown in FIGS. 30A-30D and detailed views of the cam are shown in FIGS. 29A-29F.

FIG. 26B shows the state of the cam an intermediate angular position when the extension trigger has been released and the collar rotates, causing the cam to rotate (shown in the counter clockwise direction) as well. Rotation of the cam causes the extension helices 1051 of the cam to push against the arms 1041 of the hub, driving the hub 1040 in the distal direction to move the needle 1010 into an extended position, shown in FIG. 26C, where the cam is at the final angular position for needle extension. In the extended state, the hub 1040 is held between the cam's extension helices 1051 and retraction helices 1053.

Figure 27A:
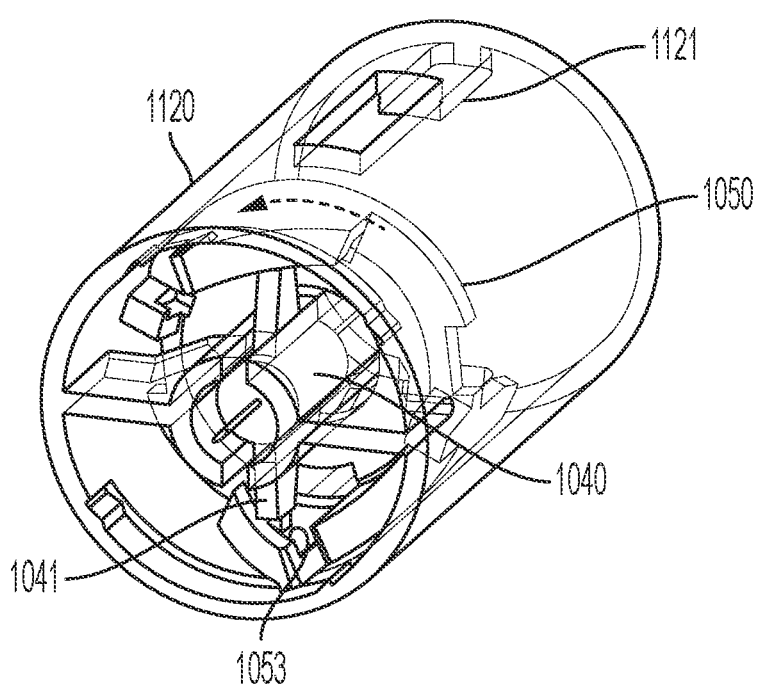
FIGS. 27A-27B depict the arrangements of the needle carrier as the drug delivery device undergoes a sequence of needle retraction steps.
Figure 27B:
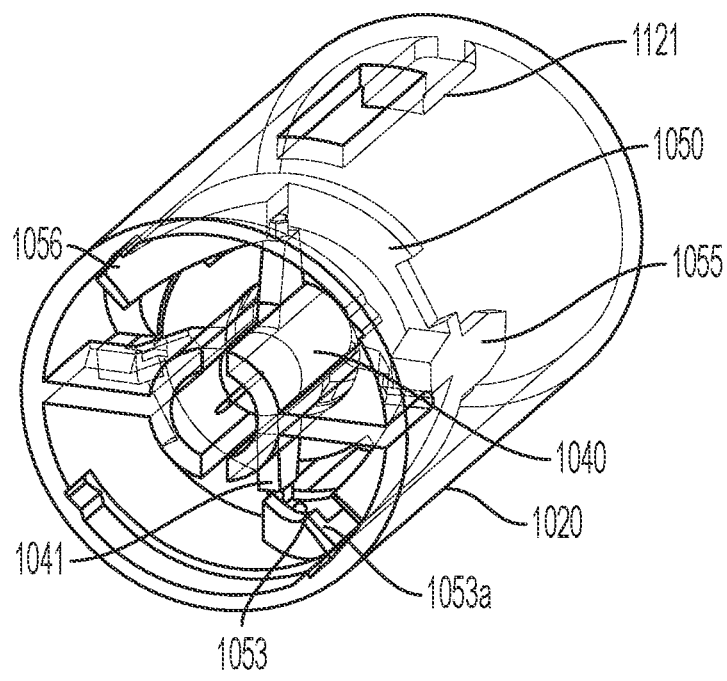
Figures 29A, 29B, 29C, 29D, 29E, 29F:
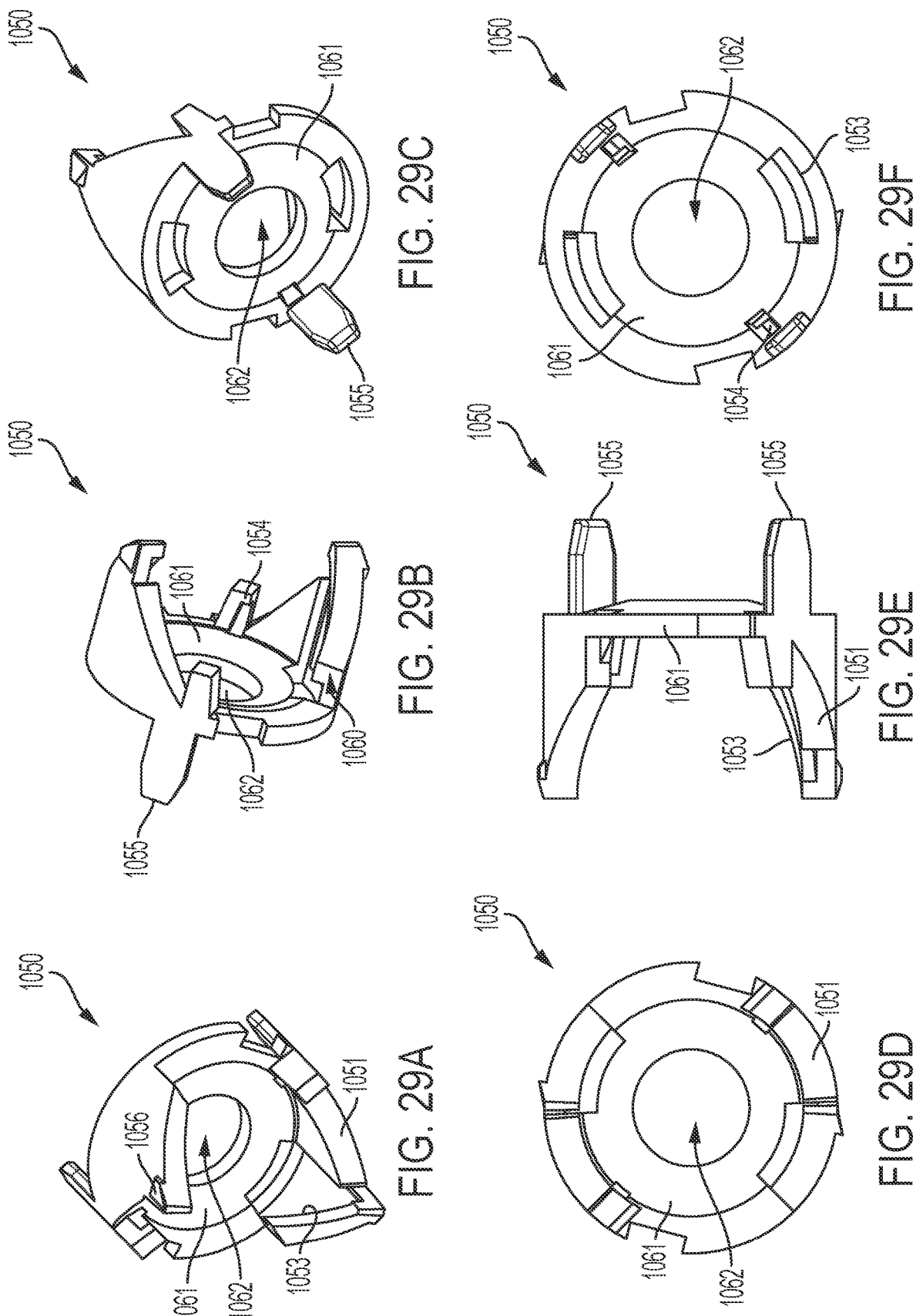
FIGS. 29A-29F depict views of a cam according to one embodiment.
Figures 30A, 30B, 30C, 30D:
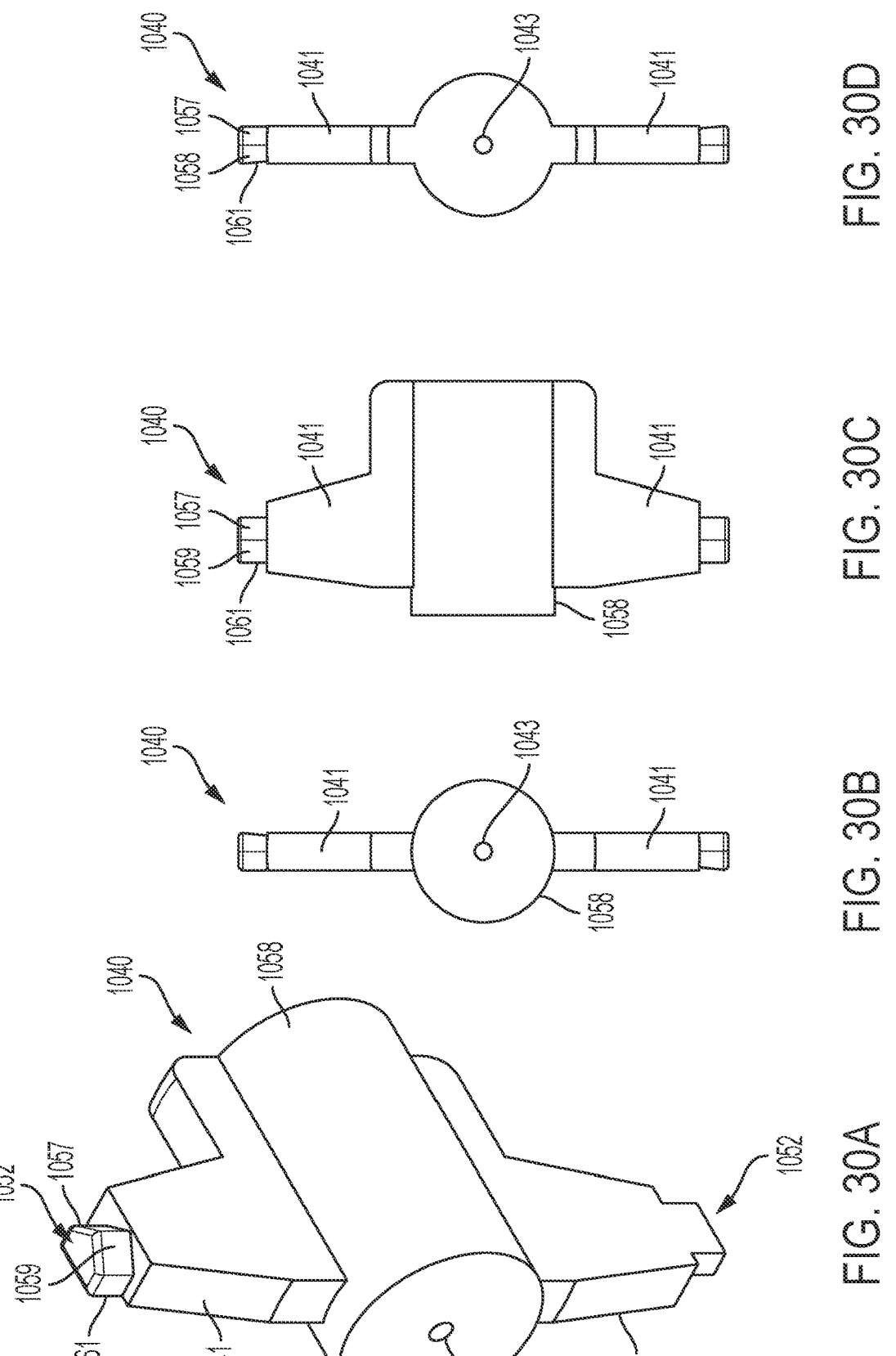
FIGS. 30A-30D depict views of a hub according to one embodiment.
Figures 31A, 31B, 31C, 31D, 31E:
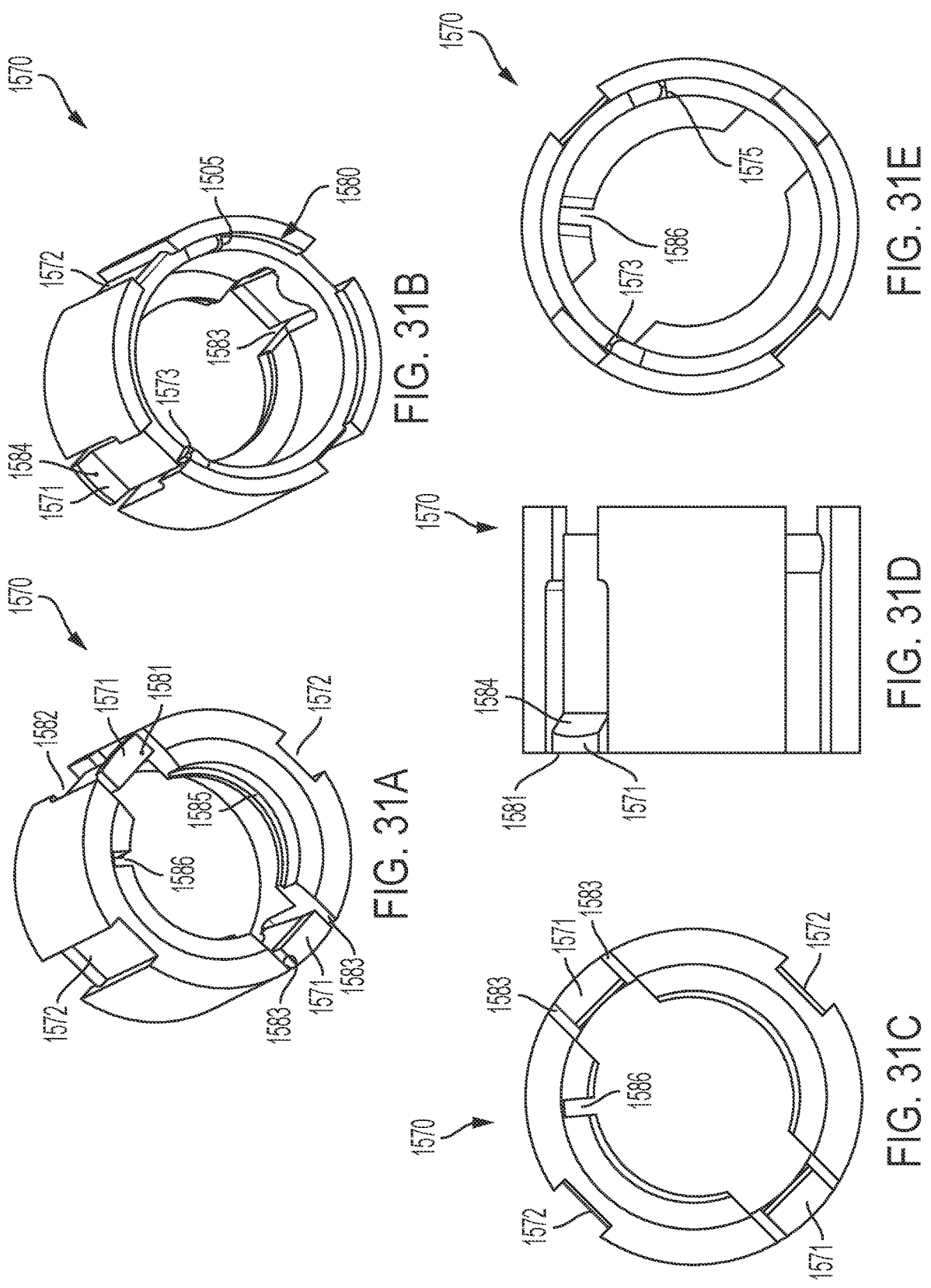
FIGS. 31A-31E depict views of a collar according to one embodiment.

FIGS. 27A and 27B depict the arrangements of the needle carrier as the drug delivery device undergoes a sequence of needle retraction steps. FIG. 27A shows the state of the cam when the retraction trigger has been released and the collar rotates, causing the cam to rotate as well (still in the counter clockwise direction). Rotation of the cam causes the retraction helices 1053 to pull against the arms 1041 of the hub 1040 in the proximal direction, thus moving the needle 1010 into a retracted position, shown in FIG. 27B. The internal radial lip 1053*a* is formed along the retraction helices 1053 that catches the end of the arms of the needle hub during retraction.

In this retracted state, the detents 1056 on the cam engage with the carrier wall, preventing the cam from rotating. In addition, in some embodiments, the cam tabs 1055 are misaligned with the carrier tabs 1121, which prohibits the carrier from being mounted onto the collar of the drug device. Such an arrangement may help to prevent re-use of the needle.

FIGS. 28A-28F depict various views of the needle carrier 1120 according to one illustrative embodiment. The needle carrier 1120 includes a cylindrical body 1123. The tabs 1121 are formed on the inner wall of the body adjacent to an end and extend along a portion of the axial length of the body 1123 and extend radially inwardly. A central bore region 1124 extends along the central axis and acts to guide the hub, specifically the central axle 1058 of the hub 1040 (see FIG. 30A). Radially inwardly extending struts 1125 attach the hub guide to the inner wall of the body. A bearing surface 1126 on each strut supports the central bore 1062 of the cam 1050. Retention snaps hold the cam to the carrier 1120. Cam rotation detents 1128 (start of cam rotation) and cam rotation snaps 1129 (end of cam rotation) limit the extent of rotational displacement of the cam.

FIGS. 29A-29F depict various views of the cam 1050 according to one illustrative embodiment. The cam 1050 includes a generally cylindrical body 1060 on which the extension cam surfaces 1051 and retraction cam surfaces 1053 are formed. Also formed on the body is are the tabs 1055. The body further includes a bearing wall 1061 through which extends the central bore 1062. As discussed above, the cam may include teeth 1054 (which in this embodiment extends axially on the cylindrical body in the same direction as the cam surfaces), detents 1056 (which are provided on the outer cylindrical body at an apex of the retraction cam surface), extension helices 1051 and retraction helices 1053.

FIGS. 30A-30D depict various views of the needle hub 1040 according to one illustrative embodiment. The hub may include arms 1041 that interact with the cam of the needle assembly during extension and retraction of a needle. As described above, the hub includes a central axle 1058. The axle 1058 may also include a bore 1043 through which the needle extends. The radially extending arms 1041 is sized to fit within the space 1127 formed in the central bore region 1124 of the needle carrier 1120. Each arm 1041 includes a radial end 1052 having first surface 1057 and second surface 1059. The first surface is configured to ride along the extension cam surface 1051 when the cam is being rotated in one direction and the second surface 1059 is configured to ride along the retraction cam surface 1053 when the cam is being rotated in the opposite direction. A forward face 1061 is configured to aid in allowing the needle to pierce the septum. In this respect, face 1061 acts as a bearing surface to transmit the force applied to the carrier as the carrier is being inserted onto the first portion 1502 of the drug device.

FIGS. 31A-31E depict various views of the collar 1570 according to one illustrative embodiment. As seen in the figures, the collar has a generally cylindrical body 1580 formed with arms 1571 and slots 1572. The arms include an abutment surface 1581 that precludes the insertion of the needle carrier 1120 along the slot 1582 defined by the arm 1571. The arms also include a ramp 1584 that causes the arm to flex radially inward (due to the gap 1583 between the arms and the body) to permit removal of the needle carrier. The slots 1572 may be configured to receive tabs of the needle carrier upon insertion, as discussed above. The collar may include a first collar stop 1573 and a second collar stop 1575 that interact with the housing of the drug device and with the retraction and extension triggers that demark the end of travel. The collar may further include a split rib 1585 that engages a collar retention groove 1587 to holds the collar onto the first portion 1502. A notch 1586 may be formed along the inner surface to anchor an end of the torsion spring.

FIGS. 32A-32D depict various views of the housing 1503 of the first portion 1502 of the drug device according to one illustrative embodiment. As discussed above, the housing 1503 may include a first housing stop 1509 and a second housing stop 1505 that interact with the collar during operation of the device. As seen in FIG. 32B, the housing may include a retraction trigger slot 1512 through which a retraction trigger can move, as well as an extension trigger slot 1514 through which an extension trigger can move. The housing may also include alignment slots 1506 configured to receive tabs of the needle carrier during coupling of the needle carrier to the housing. A trigger slot 1590 may be formed on an inner wall of the housing. The distal end of the housing includes the collar retention groove 1587.

It should be understood that the drug devices shown are illustrative, as the needle assemblies described herein can be adapted for use with variously configured drug devices, including differently constructed pen-shaped medication injection devices, differently shaped injection devices, and infusion pump devices. The medication may be any of a type that may be delivered by such a drug device. The devices shown are intended to be illustrative and not limiting as the needle assemblies described may be used in other differently configured devices.

To clarify the use of and to hereby provide notice to the public, the phrases "at least one of <A>, <B>, . . . and <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed.

While various embodiments have been described, it will be apparent to those of ordinary skill in the art that many more embodiments and implementations are possible. Accordingly, the embodiments described herein are examples, not the only possible embodiments and implementations. Furthermore, the advantages described above are not necessarily the only advantages, and it is not necessarily expected that all of the described advantages will be achieved with every embodiment.

Various aspects are described in this disclosure, which include, but are not limited to, the following aspects:

1. A drug delivery device, including a needle assembly including a needle carrier, a needle hub moveable relative to the needle carrier, and a needle coupled to the needle hub; a drug device having a container with a septum disposed at a container end opening and a carrier drive element, the needle carrier coupleable to the drug device; and a deployment trigger configured to activate the carrier drive element to move the needle hub distally from a retracted needle hub position to an extended needle hub position and to move the needle distally relative to a septum from a retracted needle position to an extended needle position.

2. The drug delivery device of aspect 1, further including a cup body configured to contain the needle carrier, the needle hub, and the needle, the cup body being removably coupled to the needle carrier.

3. The drug delivery device of aspect 2, wherein the cup body further includes a cover that is sealed to the cup body to contain the needle carrier, the needle hub, and the needle in a sealed space prior to the needle carrier being coupled to the drug device.

4. The drug delivery device of aspect 2, wherein one of the cup body and the needle carrier includes a fin and the other includes a recess shaped to receive the fin during mating of the cup body to the needle carrier.

5. The drug delivery device of any one of aspects 1-4, wherein the carrier drive element includes an axially compressible spring, wherein the needle carrier is removably coupleable to the drug device to load the spring, wherein the deployment trigger is coupled to a distal end of the needle carrier, and the deployment trigger is actuated by force applied in a proximal direction against the deployment trigger to unload the spring.

6. The drug delivery device of aspect 5, wherein the spring is disposed between the needle hub and the drug device, the needle hub includes a leg portion positioned to set the deployment trigger in a pre-actuation configuration relative to the needle carrier where the spring is loaded in an axially compressed configuration, and, in response to actuation of the deployment trigger, the deployment trigger deflects the leg portion of the needle hub radially inward such that the needle hub distally moves as the spring unloads to its axially expanded configuration.

7. The drug delivery device of aspect 5, wherein the deployment trigger is disposed coaxially relative to the needle carrier, the deployment trigger being axially moveable relative to the needle carrier between a covered position and a trigger position, wherein in the trigger position, a distal end of the needle does not extend beyond a distal end of the deployment trigger, and during movement to the trigger position, the deployment trigger engages a portion of the needle hub to unlock the needle hub from the retracted needle hub position by which the needle hub advances distally to the extended needle hub position by unloading the spring such that the distal end of the needle extends distally beyond an opening of the deployment trigger.

8. The drug delivery device of any one of aspects 1-7, further including a cam disposed radially between the needle hub and the needle carrier in a coaxial relationship, the cam configured to rotate to drive the needle hub to at least one of move the needle in an extension direction and move the needle in a retraction direction.

9. The drug delivery device of aspect 8, wherein the drug device includes a collar rotatable under a biasing force of the spring, wherein in response to the needle carrier being coupled to the collar, the cam is rotationally locked with the collar.

10. The drug delivery device of aspect 9, wherein in response to rotation of the cam by a first amount the cam slidably engages the needle hub to advance the needle in the extension direction, and wherein in response to rotation of the cam by another amount the cam slidably engages the needle hub to retract the needle in the retraction direction.

11. The drug delivery device of aspect 10, wherein the deployment trigger selectively engages the collar, and disengagement of the deployment trigger from the collar facilitates the rotation of the collar by the first amount.

12. The drug delivery device of aspect 11, further including a retraction trigger selectively engaging the collar, and disengagement of the retraction trigger from the collar subsequent to the disengagement of the deployment trigger facilitates the rotation of the collar by the another amount.

13. The drug delivery device of any one of the preceding aspects, wherein movement of the needle distally from the retracted needle position to the extended needle position includes movement of the needle through the septum.

14. The drug delivery device of aspect 13, wherein the drug device includes an outer housing, and the septum remains stationary relative to the outer housing during movement of the needle through the septum.

15. The drug delivery device of aspect 13, wherein the septum remains stationary relative to the needle carrier during coupling of the needle carrier to the drug device where the needle pierces the septum and during movement of the needle through the septum to the extended needle position.

16. The drug delivery device of any one of the preceding aspects, wherein the drug device further includes a medicament container containing a piston, the piston being moveable relative to the medicament container to expel medicament from the medicament container.

17. A method, including: providing a drug device having a container with a septum disposed at a container end opening and a carrier drive element; providing a needle assembly including a needle carrier, a needle hub movable relative to the needle carrier, and a needle coupled to the needle hub; when the needle carrier is coupled to the drug device, activating a deployment trigger to activate the carrier drive element to move the needle hub distally from a retracted needle hub position to an extended needle hub position and to move the needle relative to the septum from a retracted needle position to an extended needle position.

18. The method of aspect 17, further including: providing a cup body containing the needle assembly, the needle assembly including the deployment trigger, the carrier drive element including a spring, the needle assembly being removable from the cup body; mounting the cup body to the drug device to couple the needle carrier to the drug device, the cup body containing the needle assembly; removing the cup body from the needle assembly and from the drug device, the needle being in the retracted needle position after the piercing of the septum; after activating the deployment trigger, mounting the cup body over the needle assembly while the needle assembly is coupled to the drug device; coupling the cup body to the needle assembly; and with the needle assembly coupled to the cup body, moving the cup body away from the drug device to remove the needle assembly from the drug device.

19. The method of aspect 18, wherein the step of mounting the cup body over the needle assembly occurs while the needle is in the extended needle position.

20. The method of aspect 18, further including a step of rotating the cup body relative to the drug device when the needle assembly is coupled to the cup body to unlock the needle assembly from the drug device prior to the step of moving the cup body away from the drug device.

21. The method of any one of aspects 17-20, wherein the deployment trigger is mounted to the needle carrier and is movable relative to the needle carrier.

22. The method of aspect 21, wherein, in the retracted needle position, a distal end of the needle is flush with or proximal to a distal end of the deployment trigger.

23. The method of aspect 21, wherein, in the extended needle position, a distal end of the needle is distal to a distal end of the deployment trigger.

24. The method of aspect 21, wherein the step of pressing the deployment trigger includes pressing the deployment trigger against skin of a subject.

25. The method of any one of aspects 17-24, further including a step of moving the needle in a retraction direction after the needle is moved from the retracted needle position to the extended needle position.

26. The method of any one of aspects 17-25, wherein the drug device holds a medicament container; and further including a step of moving a piston relative to the medicament container to expel medicament from the medicament container.

27. The method of aspect 21, wherein pressing the deployment trigger to unload the spring causes the deployment trigger to move axially relative to the needle carrier from a covered position to a trigger position, wherein in the trigger position, a distal end of the needle does not extend beyond a distal end of the deployment trigger, and during movement to the trigger position, the deployment trigger engages a portion of the needle hub to unlock the needle hub from the retracted needle hub position, causing the needle hub to move distally to the extended needle hub position by unloading of the spring such that the distal end of the needle extends distally beyond an opening of the deployment trigger.

28. The method of any one of aspects 17-27, further including coupling the needle carrier to the drug device to load the spring.

29. The method of aspect 28, wherein the step of coupling the needle carrier to the drug device includes piercing a proximal end of the needle through a septum of a medicament container in the drug device.

30. The method of aspect 29, wherein movement of the needle from the retracted needle position to the extended needle position includes movement of the needle through and relative to the septum.

31. The method of any one of aspects 17-30, further including activating a retraction trigger to move the needle from the extended needle position in a retraction direction.

32. A needle assembly for coupling to a drug device having a spring and a container with a septum that includes a fluid, the needle assembly including: a needle carrier being removably coupleable to the drug device to load the spring; a needle hub movable relative to the needle carrier; a needle coupled to the needle hub; and wherein a coupling of the needle carrier to the drug device facilitates a piercing of said septum of the drug device with the needle, wherein the needle hub is movable in the distal direction relative to the needle carrier to position a distal end of the needle to extend beyond the needle carrier and a proximal end of the needle to remain within the septum in fluid communication with the fluid of the container.

33. The needle assembly of aspect 32, further including a cup housing that contains the needle carrier, the deployment trigger, the needle hub, and the needle.

34. The needle assembly of any one of aspects 32-33, wherein the needle hub is disposed within the needle carrier and is coaxial relative to the needle carrier.

35. The needle assembly of any one of aspects 32-34, wherein the deployment trigger is mounted to the needle carrier and is movable relative to the needle carrier.

36. The needle assembly of any one of aspects 32-35, wherein the deployment trigger is disposed coaxially relative to the needle carrier, the deployment trigger being axially moveable relative to the needle carrier between a covered position and a trigger position, wherein in the trigger position, a distal end of the needle does not extend beyond a distal end of the deployment trigger, and during movement to the trigger position, the deployment trigger engages a portion of the needle hub to unlock the needle hub from the retracted needle hub position, causing the needle hub to advance distally to the extended needle hub position by unloading of the spring such that the distal end of said needle extends distally beyond an opening of the deployment trigger.

37. The needle assembly of any one of aspects 32-36, further including a rotatable cam mounted radially between the needle hub and the needle carrier in a coaxial relationship, wherein in the response to rotation of the cam by unloading of the spring the needle hub advances distally to an extended needle hub position such that the distal end of said needle extends distally beyond an opening of the needle carrier.

38. The needle assembly of aspect 37, wherein in the response to rotation of the cam by further unloading of the spring the needle hub advances proximally to a retracted needle hub position such that the distal end of said needle is within the needle carrier.

39. The needle assembly of any one of aspects 32-38, further including a deployment trigger configured to unload the spring to move the needle hub distally from a retracted needle hub position to an extended needle hub position and to move the needle distally from a retracted needle position to an extended needle position.

What is claimed is:

1. A drug delivery device, comprising:
a needle assembly including a needle carrier, a needle hub moveable relative to the needle carrier, the carrier drive element comprising an axially compressible spring, and a needle coupled to the needle hub;
a drug device having a container with a septum disposed at a container end opening and a carrier drive element, the needle carrier removably coupleable to the drug device; and
a deployment trigger coupled to a distal end of the needle carrier, wherein the deployment trigger is configured to activate the carrier drive element to move the needle hub distally from a retracted needle hub position to an extended needle hub position and to move the needle distally relative to the septum from a retracted needle position to an extended needle position,
wherein in response to coupling of the needle assembly to the drug device said spring is loaded, and
wherein the deployment trigger is actuated by force applied in a proximal direction against the deployment trigger to unload said spring and to move the needle to the extended needle position.

2. The drug delivery device of claim 1, further comprising a cup body configured to contain the needle carrier, the needle hub, and the needle, the cup body being removably coupled to the needle carrier.

3. The drug delivery device of claim 2, wherein the cup body further comprises a cover that is sealed to the cup body to contain the needle carrier, the needle hub, and the needle in a sealed space prior to the needle carrier being coupled to the drug device.

4. The drug delivery device of claim 2, wherein one of the cup body and the needle carrier includes a fin and the other includes a recess shaped to receive the fin during mating of the cup body to the needle carrier.

5. The drug delivery device of claim 1, wherein the spring is disposed between the needle hub and the drug device, the needle hub includes a leg portion positioned to set the deployment trigger in a pre-actuation configuration relative to the needle carrier where the spring is loaded in an axially compressed configuration, and, in response to actuation of the deployment trigger, the deployment trigger deflects the leg portion of the needle hub radially inward such that the needle hub distally moves as the spring unloads to its axially expanded configuration.

6. The drug delivery device of claim 1, wherein the deployment trigger is disposed coaxially relative to the needle carrier, the deployment trigger being axially moveable relative to the needle carrier between a covered position and a trigger position, wherein in the trigger position, a distal end of the needle does not extend beyond a distal end of the deployment trigger, and during movement to the trigger position, the deployment trigger engages a portion of the needle hub to unlock the needle hub from the retracted needle hub position by which the needle hub advances distally to the extended needle hub position by unloading the spring such that the distal end of the needle extends distally beyond an opening of the deployment trigger.

7. The drug delivery device of claim 1, further comprising a cam disposed radially between the needle hub and the needle carrier in a coaxial relationship, the cam configured to rotate to drive the needle hub to at least one of move the needle in an extension direction and move the needle in a retraction direction.

8. The drug delivery device of claim 7, wherein the drug device includes a collar rotatable under a biasing force of the spring, wherein in response to the needle carrier being coupled to the collar, the cam is rotationally locked with the collar.

9. The drug delivery device of claim 8, wherein in response to rotation of the cam by a first amount the cam slidably engages the needle hub to advance the needle in the extension direction, and wherein in response to rotation of the cam by another amount the cam slidably engages the needle hub to retract the needle in the retraction direction.

10. The drug delivery device of claim 9, wherein the deployment trigger selectively engages the collar, and disengagement of the deployment trigger from the collar facilitates the rotation of the collar by the first amount.

11. The drug delivery device of claim 10, further comprising a retraction trigger selectively engaging the collar, and disengagement of the retraction trigger from the collar subsequent to the disengagement of the deployment trigger facilitates the rotation of the collar by the another amount.

12. The drug delivery device of any one of claim 1, 5, and 6, wherein movement of the needle distally from the retracted needle position to the extended needle position comprises movement of the needle through the septum.

13. The drug delivery device of claim 12, wherein the drug device includes an outer housing, and the septum remains stationary relative to the outer housing during movement of the needle through the septum.

14. The drug delivery device of claim 12, wherein the septum remains stationary relative to the needle carrier during coupling of the needle carrier to the drug device where the needle pierces the septum and during movement of the needle through the septum to the extended needle position.

15. The drug delivery device of claim 1, wherein the drug device further comprises a medicament within the container, and a piston being moveable relative to the container to expel medicament from the container.

16. A drug delivery device, comprising:

a drug device having a container with a septum disposed at a container end opening and a needle drive comprising a spring disposed at a coupling end of the drug device;

a needle assembly including a needle carrier, a needle hub moveable relative to the needle carrier, and a needle coupled to the needle hub, wherein the needle assembly is removably coupled to the coupling end of the drug device to load said spring, wherein the needle drive of the drug device is configured to move the needle hub distally; and a deployment trigger configured to facilitate unloading of said spring and to activate the needle drive, wherein in response to activation of the deployment trigger, the needle hub is moved distally from a retracted needle hub position to an extended needle hub position and the needle is moved distally relative to the septum from a retracted needle position to an extended needle position.

17. The drug delivery device of claim 16, wherein the spring comprises an axially compressible spring, wherein the needle assembly is removably coupleable to the drug device to load the axially compressible spring.

18. The drug delivery device of claim 17, wherein the deployment trigger is coupled to a distal end of the needle carrier, and the deployment trigger is actuated by force applied in a proximal direction against the deployment trigger to unload the spring.

19. The drug delivery device of claim 16, wherein the spring is disposed between the needle hub and the drug device, the needle hub includes a leg portion positioned to set the deployment trigger in a pre-actuation configuration relative to the needle carrier where the spring is loaded in an axially compressed configuration, and, in response to actuation of the deployment trigger, the deployment trigger deflects the leg portion of the needle hub radially inward such that the needle hub distally moves as the spring unloads to its axially expanded configuration.

* * * * *